(12) United States Patent
Hibri

(10) Patent No.: US 11,737,885 B1
(45) Date of Patent: *Aug. 29, 2023

(54) INFLATABLE SPINAL IMPLANTS AND RELATED SYSTEMS AND METHODS

(71) Applicant: Spica Medical Technologies, LLC, San Antonio, TX (US)

(72) Inventor: Nadi S. Hibri, San Antonio, TX (US)

(73) Assignee: Spica Medical Technologies, LLC, San Antonio, TX (US)

( * ) Notice: Subject to any disclaimer, the term of this patent is extended or adjusted under 35 U.S.C. 154(b) by 410 days.

This patent is subject to a terminal disclaimer.

(21) Appl. No.: 17/079,189

(22) Filed: Oct. 23, 2020

Related U.S. Application Data

(63) Continuation of application No. 16/709,807, filed on Dec. 10, 2019, now Pat. No. 10,821,002.

(51) Int. Cl.
| | |
|---|---|
| *A61F 2/44* | (2006.01) |
| *A61B 17/88* | (2006.01) |
| *A61F 2/46* | (2006.01) |
| A61F 2/30 | (2006.01) |
| A61M 25/10 | (2013.01) |

(52) U.S. Cl.
CPC ............ *A61F 2/441* (2013.01); *A61F 2/4611* (2013.01); *A61F 2002/3008* (2013.01); *A61F 2002/30583* (2013.01); *A61F 2002/4687* (2013.01); *A61M 25/1011* (2013.01)

(58) Field of Classification Search
CPC ................... A61F 2/441; A61F 2/4611; A61F 2002/3008; A61F 2002/30583; A61F 2002/4687; A61M 25/1011
USPC ...... 623/17.12; 606/279, 246, 92, 93, 94, 99, 606/105.86 A
See application file for complete search history.

(56) References Cited

U.S. PATENT DOCUMENTS

| | | |
|---|---|---|
| 5,571,189 A | 11/1996 | Kuslich |
| 6,127,597 A | 10/2000 | Beyar et al. |
| 6,899,719 B2 | 5/2005 | Reiley et al. |
| 7,758,644 B2 | 7/2010 | Trieu |
| 8,784,491 B2 | 7/2014 | Biedermann et al. |
| 2002/0099384 A1 | 7/2002 | Scribner et al. |
| 2003/0074075 A1 | 4/2003 | Thomas et al. |

(Continued)

*Primary Examiner* — Eduardo C Robert
*Assistant Examiner* — David C Comstock
(74) *Attorney, Agent, or Firm* — Pizarro Allen PC

(57) ABSTRACT

Inflatable spinal implants are disclosed for intra-vertebral or inter-vertebral reduction and fixation of osteoporotic fractures in a spine. An inflatable implant may include an inflatable member having an interior for receiving a hardenable fluid and an expandable jacket to cause differential and directional expansion of the inflatable member. A one-way valve may be configured to prevent hardenable fluid from escaping out of the inflatable member. An inflatable implant may include a connection fixation device having a fluid coupling configured for releasable engagement with an inflation cannula and an anchoring portion configured for holding the implant in place within a vertebra. The fluid coupling may also be configured for releasable engagement with an anti-rotation device, which may be used to hold the implant stationary to facilitate engagement and disengagement of the inflation cannula with the fluid coupling. Related systems and methods are also described.

22 Claims, 56 Drawing Sheets

(56) References Cited

U.S. PATENT DOCUMENTS

| | | | |
|---|---|---|---|
| 2005/0209602 A1* | 9/2005 | Bowman | A61B 17/8836 606/90 |
| 2007/0293866 A1 | 12/2007 | Stoeckel et al. | |
| 2010/0286782 A1 | 11/2010 | Schaller et al. | |
| 2011/0046737 A1 | 2/2011 | Teisen | |
| 2012/0136448 A1* | 5/2012 | Seifert | A61B 17/1671 623/17.16 |
| 2014/0277465 A1* | 9/2014 | Teisen | A61B 17/7097 623/17.12 |
| 2016/0022427 A1* | 1/2016 | Nakagawa | A61F 2/4405 623/23.47 |
| 2017/0246005 A1* | 8/2017 | Hibri | A61F 2/442 |
| 2020/0113705 A1* | 4/2020 | Francis | A61F 2/4601 |

\* cited by examiner

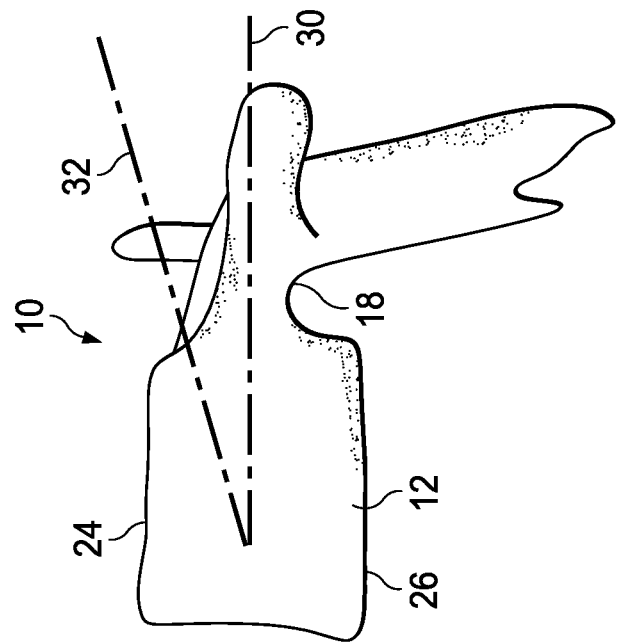
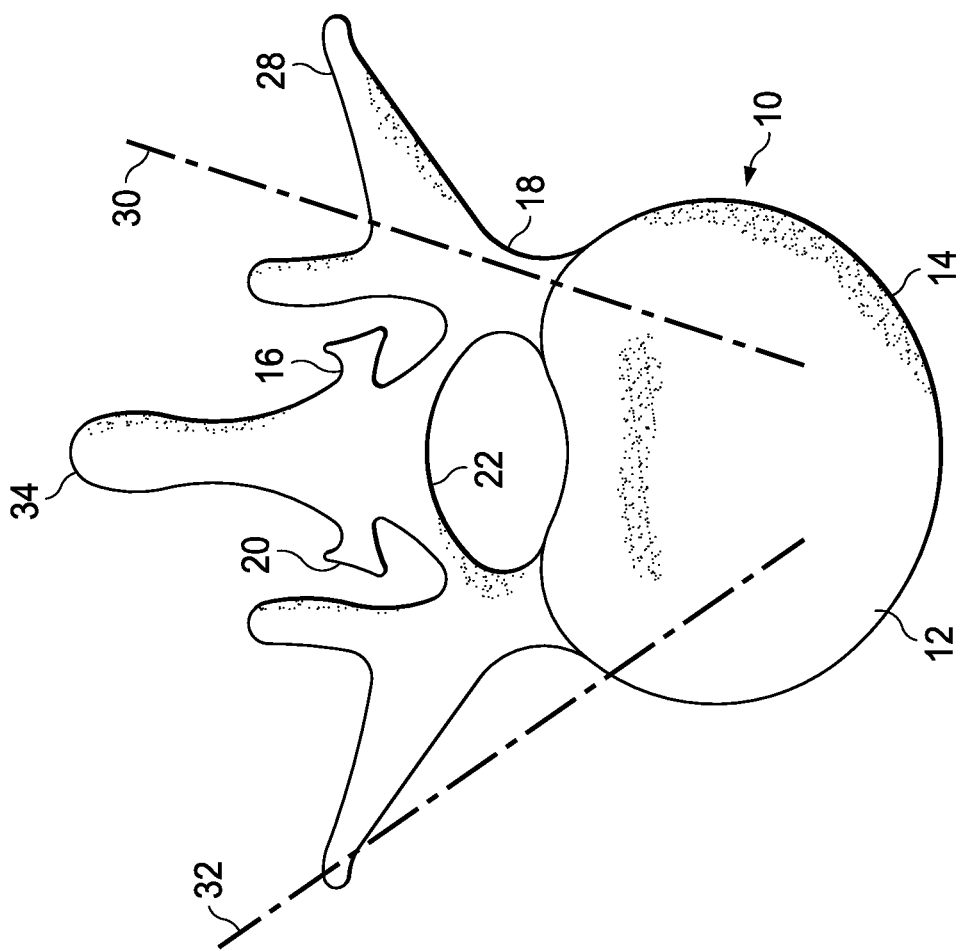
FIG. 37B
FIG. 37A

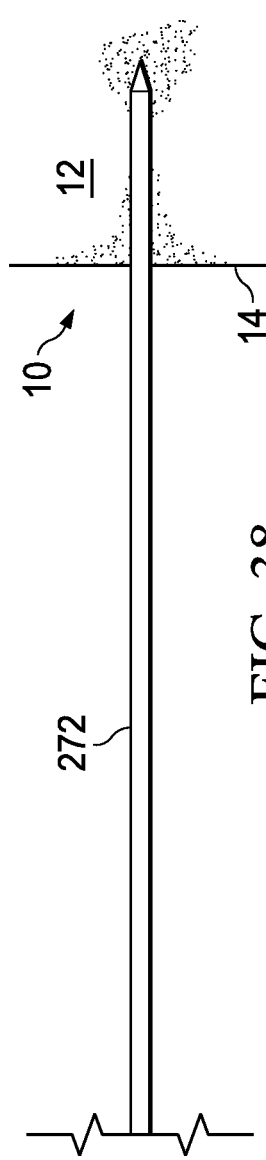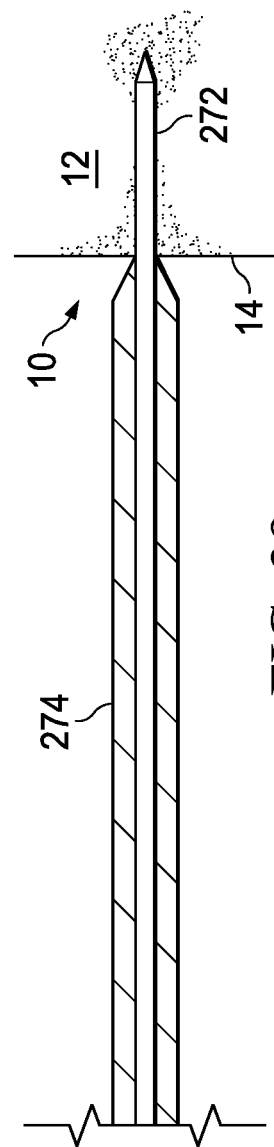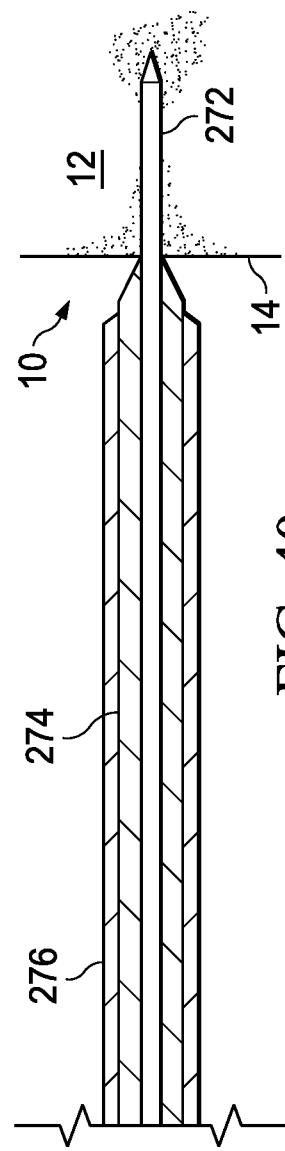

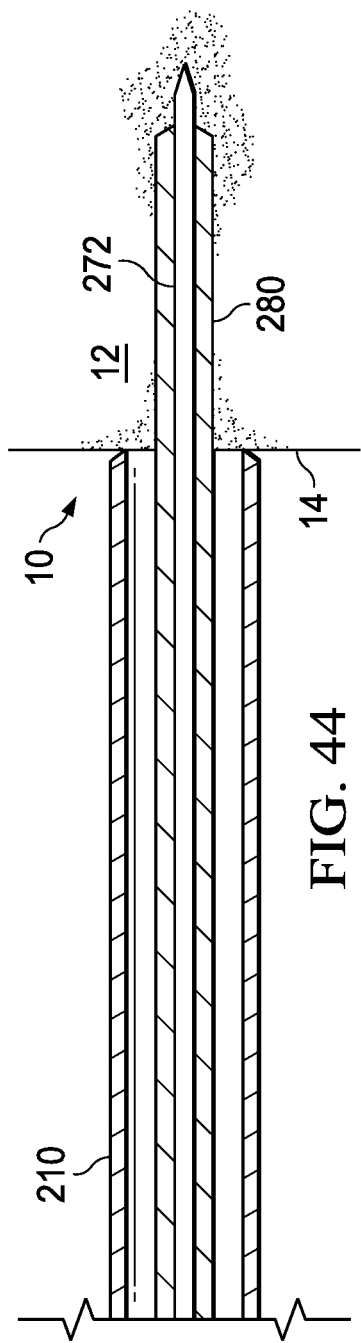
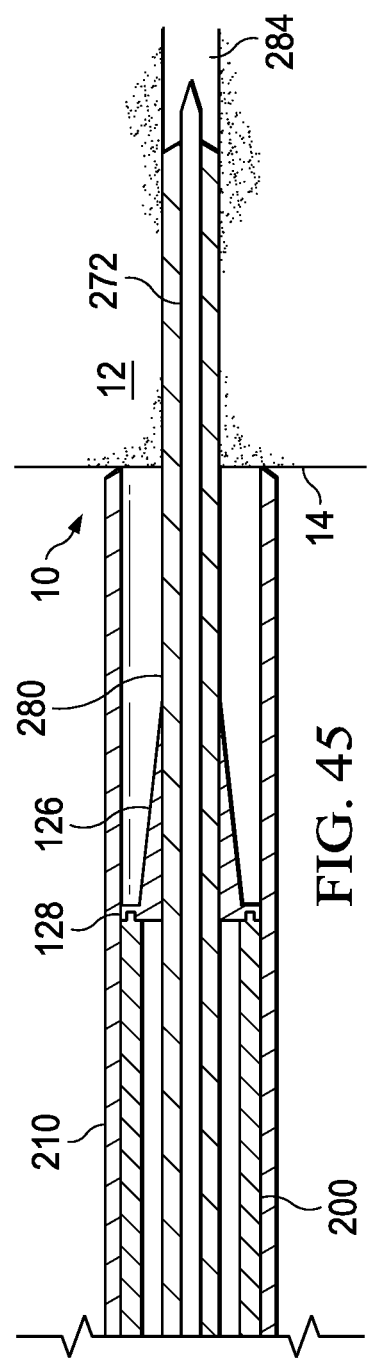

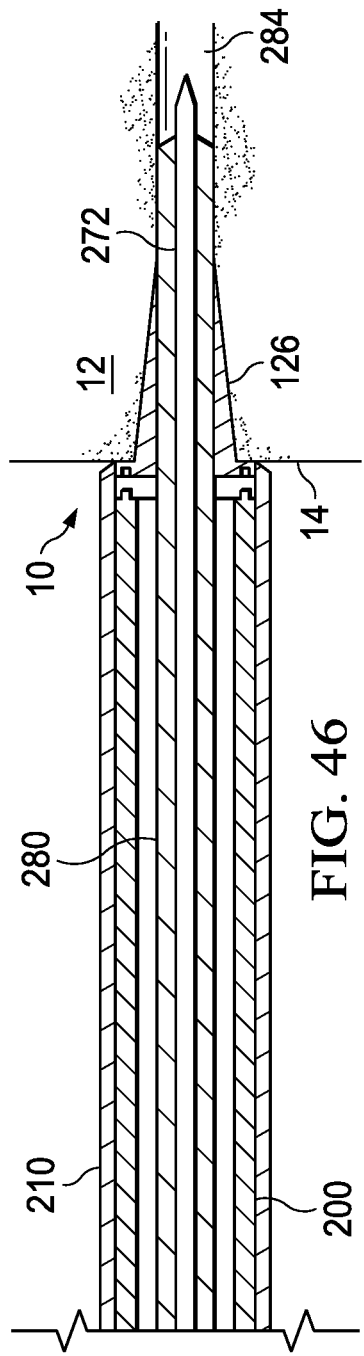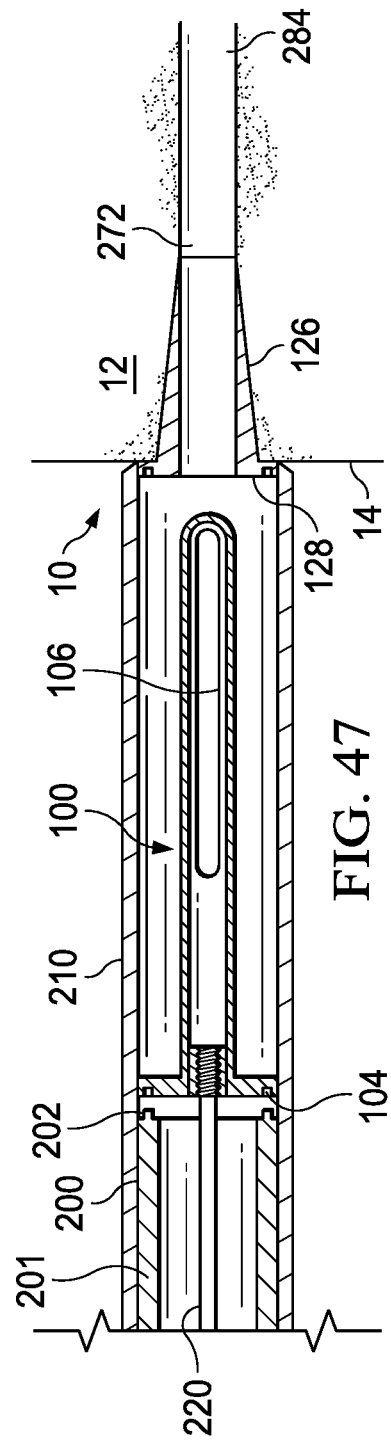

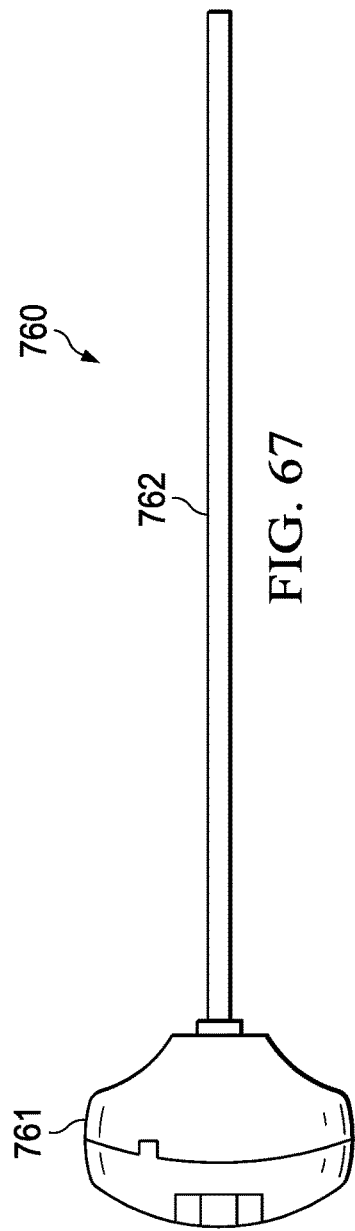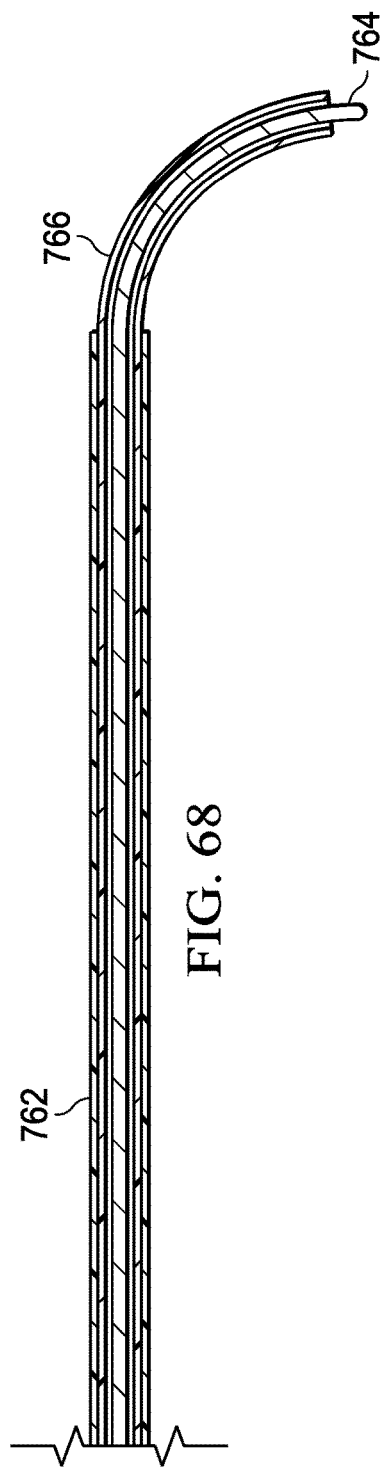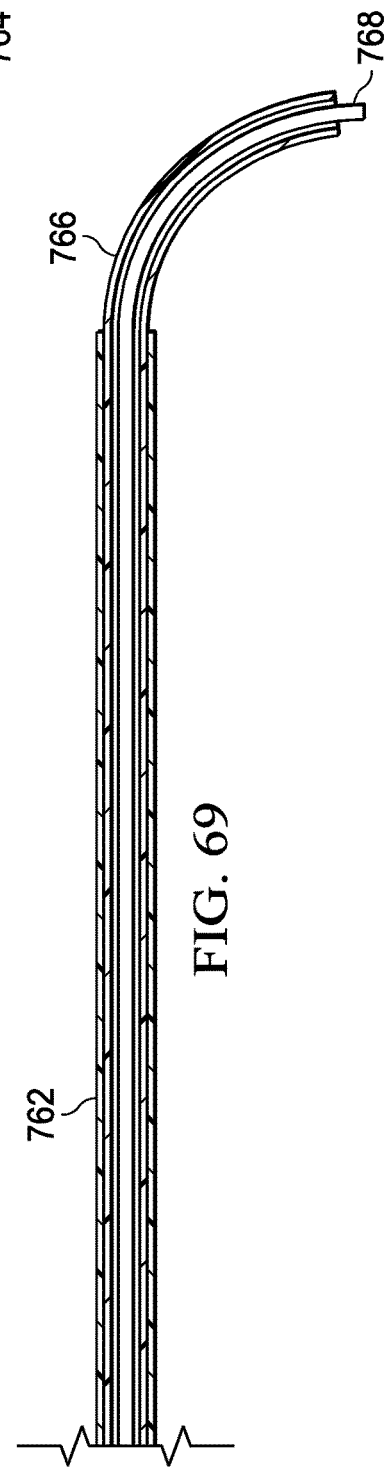

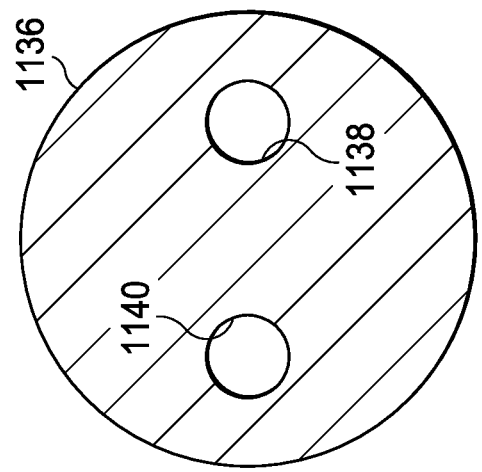
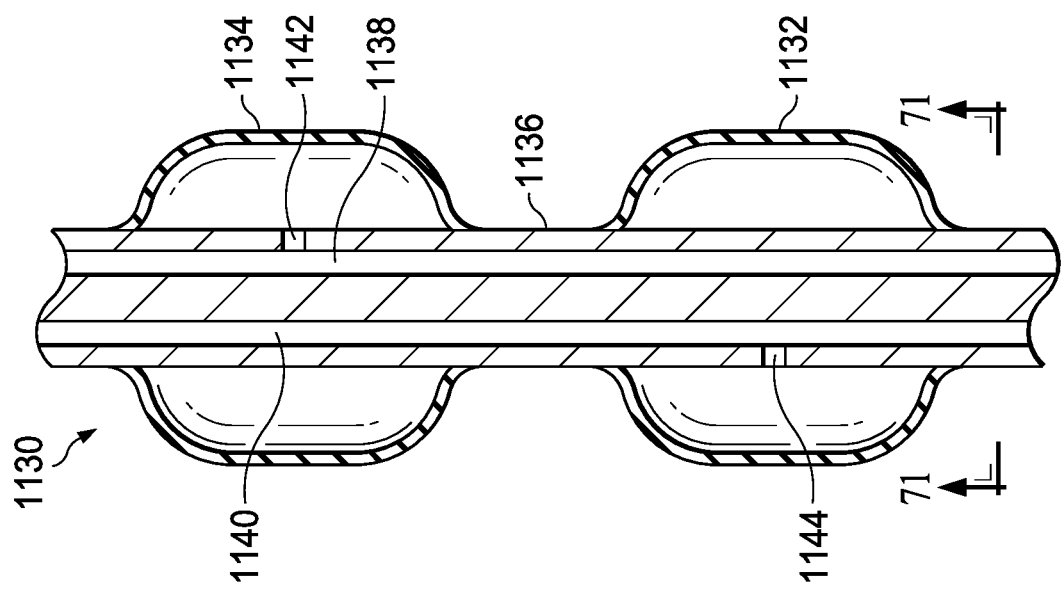

INFLATABLE SPINAL IMPLANTS AND RELATED SYSTEMS AND METHODS

CROSS-REFERENCE TO RELATED APPLICATIONS

This application is a continuation of U.S. patent application Ser. No. 16/709,807 filed Dec. 10, 2019, the disclosure of which is incorporated herein by reference.

FIELD

The present disclosure relates to medical devices and, more particularly, to systems and methods for forming spinal reduction, fixation, or stabilization implants in place within the body.

BACKGROUND

This section is intended to provide a background or context to the invention that is recited in the claims. The description herein may include concepts that could be pursued, but are not necessarily ones that have been previously conceived or pursued. Therefore, unless otherwise indicated herein, what is described in this section is not prior art to the description and claims in this application and is not admitted to be prior art by inclusion in this section.

In spinal osteoporosis, vertebral bone loss is faster from trabeculae than from the cortex. Trabeculae tend to be denser in the posterior aspect of the vertebral body and in the pedicles compared with the anterior aspect of the vertebral body. Likewise, trabeculae generally are denser in the inferior half of the vertebral body compared with the superior half, possibly because they are reinforced by trabecular arcades from the pedicles. The typical osteoporotic vertebral fracture leads to a height loss in the anterior portion of the vertebral body, often leaving the posterior vertebral wall intact. This wedge-shaped deformity of a single fractured vertebra often leads to a local increase in kyphosis.

Other vertebrae adjacent a fractured vertebra have been shown to have a fivefold increased fracture risk compared to normal vertebrae, leading to multiple vertebral fractures or "vertebral fracture cascade." Multiple adjacent vertebral fractures lead to a progressive kyphotic deformity with sagittal imbalance and postural disfigurement. A single anterior wedge fracture can increase thoracic kyphosis by ten degrees or more, and thoracic curvatures exceeding 70 degrees are common in elderly subjects with multi-level compression fractures.

Open surgical procedures for reduction of osteoporotic vertebral fractures are generally considered too invasive and impractical for this fragile population age group. The current management of osteoporotic vertebral body compression fractures therefore includes conservative measures. However, because of the problems associated with prolonged bed rest and use of analgesics, vertebroplasty and kyphoplasty procedures have been introduced.

Kyphoplasty procedures compress the cancellous bone within a vertebral body using an inflatable balloon, creating a cavity within the bone that can be filled with a cement or any number of synthetic bone substitutes. However, when the balloon is deflated and removed to accommodate placement of filler material in the created cavity, vertebral fracture reduction can be lost, with recurrence of height reduction and kyphosis. Furthermore, it is difficult to control and target the filler material into the desired areas within the vertebral body. Intravertebral reduction with balloons generally involves the bone filler being injected under high pressures, increasing the difficulty in controlling and targeting the filler material within the vertebral body. Also, there is always the danger of inadvertent leakage of the filler material. Another inherent challenge of kyphoplasty is that tamponade of cancellous bone can provide inconsistent results since the bone material can influence the direction and degree of expansion.

One issue associated with vertebroplasty and kyphoplasty is containment of the cement within the margins of the osteoporotic cortical bone or created cavity. For instance, when osteoporotic demineralization is severe, the bone trabeculae are very thin and weak, compromising the mechanical strengthening advantage of interdigitation of the cement among the trabeculae. In other instances, horizontal fissure or pseudarthrosis is present rendering the cementation process problematic. Cement leakage can occur into the adjacent disc through end plate fractures or defects. Paravertebral leak is most ominous if it happens into the spinal canal or neural foramina. Leakage into the venous system is common, with potentially disastrous consequences including embolism to the lungs.

Post procedural difficulties to existing forms of kyphoplasty may include incomplete fracture reduction or a significant loss of reduction after balloon tamp deflation, prior to cement injection. Other difficulties may include formation of a "barrier layer" following cancellous bone compaction that counteracts the beneficial effects of cement interdigitation. Poor cement-bone interface strength occasionally leads to loosening of the cement bolus, pseudarthrosis, instability, and postoperative dislodgement of the cement bolus.

More recently, vertebral body stenting (VBS) procedures and cement-directing vertebral implants have been advocated. Flexible mesh bags or balloons are inserted into the void that has been formed in the bone and filled with hardenable materials, bone chips, or cement. Bags with regions of differential cement permeability have also been advocated to foster beneficial interdigitation of bone cement with the surrounding cancellous bone.

Recently a VBS procedure was tested in vitro and compared to kyphoplasty. VBS uses a specially designed catheter-mounted stent which can be implanted and expanded inside the vertebral body. The height loss after balloon deflation was significantly decreased by using VBS compared to kyphoplasty, thus offering another option for vertebral augmentation.

One type of expandable device is shown in U.S. Pat. No. 7,758,644 B2, which is directed to expandable devices that include a body defining a hollow interior for receiving a distal portion of a delivery instrument. The expandable devices are collapsed on the distal portion of the delivery instrument for delivery to the operative site within a vertebral body. Upon delivery of the collapsed expandable devices to the operative site, the distal portion of the delivery instrument is enlargeable to expand the expandable devices in situ for implantation at the operative site.

However, these approaches may be limited in their use because most available devices cannot provide the desired reduction and stabilization functions to a severely osteoporotic fractured vertebra demonstrating significant loss of height and abnormal angulation. Furthermore, the danger of cement leakage has not been adequately obviated.

Accordingly, it would be a significant advancement in the art to provide a new and improved vertebral reduction and stabilization device that can achieve vertebral restoration of height and angle and can substantially prevent leakage of cement out of the vertebral body.

SUMMARY

In one aspect, an expandable prosthesis is configured to controllably differentially expand in different planes of a fractured vertebral body upon implantation and fluid pressurization. Secure fixation may be achieved by distractive forces directed primarily at the superior and inferior end plates, thus maximizing the implant-cortical bone area of the surface purchase. Creation of a large void that compacts and destroys the patient's otherwise weakened but intact remaining trabeculae may be avoided. Additionally, a smaller volume of cement is needed to achieve optimal reduction and augmentation.

In some embodiments, an expandable prosthesis may include an inflatable member (sometimes referred to herein as a balloon) that assumes a bellow-like configuration following expansion that may improve tissue purchase and interdigitation thus reducing the possibility of pseudarthrosis formation. Furthermore, micro movements and migration of the implant or fractured bone fragments may be reduced and thus pain may be relieved.

In some embodiments, an expandable prosthesis may provide liquid cement containment, thus substantially eliminating the possibility of cement leakage into the venous system, spinal canal, neural foramen, or intervertebral disc. Unlike some existing technologies that call for creating a void within cancellous bone by compacting the cancellous bone prior to injecting cement, or the use of more viscous cement to reduce excessive cement flow, the use of a contained inflatable member in some embodiments as described in the present disclosure may allow the use of smaller filling cannulas, fastening elements, and connecting assemblies. This latter feature of the present disclosure will become evident particularly in instances of small pedicles, especially in the middle to upper thoracic spine as will be explained in more detail below.

In one aspect, a cartridge assembly may include a housing and a loading chamber for containing an inflatable member in contracted form within the housing. The housing may include a proximal portion having an inlet for introducing hardenable fluid into the prosthesis and a distal elongated portion having at least one housing slot disposed along the longitudinal axis of the housing.

In some embodiments, a cartridge assembly may be coaxially arranged within a fastening element passageway and adapted for extension through a cartridge slot into a fractured vertebral body.

In some embodiments, a cartridge assembly and an inflatable member may be coupled to provide controlled directional expansion and stabilization of a fractured vertebral body.

In some embodiments, an inflatable member may include a proximal end fitting having a first engaging member that is reversibly engagable to a second engaging member at a distal end of an inflation cannula and a one-way, self-sealing valve in fluid communication with the lumen of the inflatable member.

One aspect of the present disclosure may include an access assembly for percutaneously creating a path to the vertebral implantation site and for placing a cartridge assembly therein.

One aspect of the present disclosure may include a delivery assembly for placing a kyphoplasty cartridge assembly inside a patient's fractured vertebra. The delivery assembly may include a delivery cannula dimensioned to receive the cartridge assembly coupled to an inflation cannula. The delivery cannula may be slidable within an access cannula. The inflation cannula may include a first engaging member, and the cartridge assembly may include a second engaging member. The first and second engaging members may be configured for reversibly engaging the inflation cannula and the cartridge assembly within the delivery cannula to temporarily lock the position of the inflation cannula with respect to the cartridge assembly, pressurizing the inflatable member in-situ without risk of inadvertent disengagement or leak of hardenable fluid, and safely disengaging the first and second engaging members at the end of the procedure.

In some embodiments, an implantable cartridge assembly may eliminate unwanted relative motion between an inflatable member and a vertebral pedicle or posterior vertebral cortex, thus maintaining the patient's spine in a corrected orientation during the period of curing of the hardenable media.

In some embodiments, the apparatus may generally include a connection fixation device (CFD) that is operably coupled to a kyphoplasty implant at its distal end and to an engaging portion at its proximal end. The combination of a CFD and kyphoplasty implant is sometimes referred to herein as a CFD-KI.

One aspect of the disclosure provides a CFD having a tubular body that includes a threaded connection portion disposed on a first end thereof. The tubular body may have an outside diameter selected such that the tubular body fits into the lumen of a delivery cannula. An anti-rotation device and an inflation cannula may be coaxially disposed within the delivery cannula proximal to the CFD. A threaded female connector portion of the CFD may be adapted to mate with a threaded male portion of the inflation cannula.

Another aspect of the disclosure may provide a CFD that includes an implant attachment section disposed on a second end thereof.

Another aspect of the disclosure is a CFD that provides fixation means by an intermediate section thereof that anchors the CFD to the implantation path in the spine. The anchoring mechanism may provide barbs or anchors which extend outward from the device and penetrate the bone tissues along the implantation path. During loading of the spinal implant with the CFD into the delivery cannula, the anchors can be compressed and retracted into the anchoring section to provide a small profile to fit inside the delivery cannula.

In accordance with some embodiments of the present invention, a percutaneous spinal implant system may include a delivery cannula and a spinal implant including a CFD, which is removably connected to an anti-rotation device and to an inflation cannula. The delivery cannula may include a proximal end, a distal end, and a lumen extending therebetween. The CFD may be configured to deliver curable fluid media from the lumen of the inflation cannula to the lumen of the inflatable member of the spinal implant. The engaging portion of the inflation cannula may operably couple the inflation cannula to the CFD, insuring a secure connection that is leak-proof (preventing leakage of the curable fluid media), can resist inadvertent disengagement at high inflation pressures, and provides quick and easy disengagement at the end of the procedure.

Another embodiment of the present invention is directed to a percutaneous spinal implant system. The delivery cannula may have a lumen in which an anti-rotation device is coaxially disposed. The anti-rotation device may include an engaging portion at its tip that is configured to hold the CFD stationary during engagement and disengagement of the inflation cannula with the CFD.

According to still another embodiment of the present invention, the CFD may include an expandable anchoring portion which, when expanded, engages firm biological tissue along the implantation path to anchor the CFD and immobilize the implant. The anchoring portion may be compressible to a minimal profile to fit snugly within the lumen of the delivery cannula.

Yet another illustrative embodiment of the present invention may include a spinal implant having an inflatable member that is expandable with fluid hardenable media. Various implant designs of various sizes and configurations are disclosed.

In another illustrative embodiment of the present invention, a method is provided for percutaneously treating an osteoporotic vertebral body fracture using an apparatus as described herein.

In one aspect, a kypho-prosthesis for multilevel vertebral implantation comprises an inflatable member that may include a balloon and an overlying supporting structure such as a stent, a mesh, a braid, or the like. The supporting structure may allow the balloon to controllably expand differentially and directionally and assume predetermined configurations, spanning both vertebral levels, crossing an intervertebral disc.

In another aspect, an implant deployment apparatus may include a straight guide cannula, a pre-curved guide pin with an overlying pre-curved access cannula, and a pre-curved delivery cannula, slidable within the pre-curved access cannula, the delivery cannula carrying the kyphoplasty prosthesis in a contracted state together with an inflation cannula.

In yet another aspect, a method is provided for performing an access, delivery, and deployment procedure that includes introducing the prosthesis into the patient's vertebrae by a transpedicular or parapedicular interventional approach in a contracted condition; positioning the kyphoplasty prosthesis within adjacent vertebral bodies and across an intervertebral disc; and expanding the inflatable member directionally and differentially within both vertebrae under fluoroscopic guidance, thereby correcting the spinal deformity, and stabilizing the vertebral segment.

In one illustrative embodiment, the present invention is directed to providing a multi-level kyphoplasty prosthesis formed from an inflatable member that may include an overlying support structure and which may be implanted using a bilateral transpedicular or parapedicular percutaneous interventional technique.

One variation of the multi-level kyphoplasty prosthesis described herein has a segmented, elongated body with a strong expansion force when desired. To provide expansion when hydraulic pressure is applied, the prosthesis has a strong directional, longitudinal biasing system to provide this expansion force.

Another variation of the multi-level kyphoplasty prosthesis described herein is a segmented, elongated inflatable body with manually or selectively steerable segments. The selectively steerable portion can be flexed in any direction by a plurality of balloon members that are independently radially expandable and adjustable in inflation size. The plurality of balloon members may be tailored to bias the prosthesis by deforming, expanding, extending, twisting, bending or straightening the prosthesis as desired for a particular clinical application. The inflatable member may be divided into a plurality of segments. The actuators may deform or reshape themselves with respect to the adjacent trabeculae in order to augment the osteoporotic bone and correct spinal deformity.

In some embodiments of the present invention, a kyphoplasty implant for insertion into two adjacent vertebral bodies having an intervertebral disc therebetween is provided. The kyphoplasty implant comprises an inflatable member having adjustable expansion capability, the implant comprising an elongated elastomeric shaft having a shaft distal end, a shaft proximal end, a shaft distal section, a shaft proximal section, and a plurality of lumens between the shaft distal end and the shaft proximal end. A portion of the shaft between the ends may comprise collapsible bellows, the bellows including an inflatable chamber and a constraining sleeve of fabric. The inflatable chamber may be configured to expand in response to an increase in fluid pressure within the chamber. The sleeve of fabric may constrain the fabric of the chamber; however, the sleeve of fabric may include corrugations that facilitate some expansion of the sleeve.

An aspect of some embodiments of the invention is controlled, directional expansion of an implantable multi-level kyphoplasty prosthesis such that during expansion the fractured or collapsed vertebral end plates are directed in the cranio-caudal plane (as desired by an operator), for example, to correct deformity in the sagittal and coronal planes. In some embodiments, the device may be configured to provide a varying resistance to expansion in the radial direction of the spine in order to limit undue lateral expansion or posterior expansion towards the spinal canal. As a result, when expansion occurs, the regions of lesser resistance to expansion may expand before the regions of greater resistance to expansion.

In some embodiments, the device may comprise a balloon wherein the thickness of the balloon material varies along one sidewall of the balloon, the varying thickness providing a varying resistance to expansion, the thinner material providing lesser resistance to expansion, and the thicker material providing greater resistance to expansion, so that the balloon tends to directionally expand or differentially expand.

In some embodiments, the device may comprise a balloon-expandable stent crimped onto the balloon with a varying crimping force along the length of the stent. In some embodiments, whereas the device comprises a balloon-expandable stent, the stent may be more resistant to expansion at the level of the intervertebral disc. In other examples, separate stents may be positioned over the segmented balloons, spanning the intervertebral disc.

In some embodiments, the implantable multi-level kyphoplasty prosthesis may further include an externally placed expansion-preventing element.

In some embodiments, the externally placed expansion-preventing element may include a supporting structure secured over or along a catheter tubing carrying the balloon or inflatable member at a first location proximal to the balloon and at a second location distal to the balloon.

In some embodiments, a multi-level kyphoplasty implant may include at least two segmented non-compliant balloons that maintain flexibility at the waist portion when inflated. In an exemplary embodiment, an inflatable multi-level kyphoplasty implant may be configured to include supporting structures such as braid, wrap, mesh, and the like, which may be carried by the balloon membranes of the segmented balloons, e.g., wrapped or otherwise positioned externally of the segmented balloon membranes, spanning the waist portion. The supporting structure may allow the implant to maintain increased flexibility when inflated such that the implant is able to bend or curve at the waist even at relatively high inflation pressures. Generally, the multi-level kyphoplasty implant assembly may include a catheter having a length, at least two segmented inflatable balloons, e.g., with a waist portion therebetween, two substantially conical or otherwise tapered end sections, positioned upon the catheter, or inner tubing having a proximal portion or connector portion, a blunt distal tip portion, and a supporting structure secured over or along the catheter at the proximal location, mid or waist location, and distal or tip location, such that inflation of the segmented balloons reconfigures the supporting structure to urge the first location, the second location, and the third location towards one another thereby: (1) limiting longitudinal elongation of the segmented balloons relative to the catheter, (2) controllably biasing the implant (and secondarily the spinal segment) to reverse or correct kyphotic deformity of the affected vertebral segment, (3) stabilizing the vertebral segment by providing desired surface characteristics of interdigitation with the bone trabeculae, such as protrusions extending from the surface of the balloon membrane, and (4) anchoring the implant in position by providing locking and retaining mechanisms configured to secure the prosthesis in place within the vertebral segment.

In accordance with another embodiment, a method is provided for percutaneously implanting a multi-level kyphoplasty prosthesis that includes providing a multi-level kyphoplasty implant as described herein. The balloon catheter including the segmented balloons and overlying support structures may be positioned for insertion into at least two adjacent vertebral bodies, each having first and second end plates with an intervertebral disc therebetween. The segmented balloons may be inflated simultaneously or sequentially under fluoroscopic guidance. The expanded structure may remain within the vertebral segment, and the inflation cannula and delivery cannula may be removed.

In some embodiments, a spinal implant may include a housing including a wall having at least one opening therein; an inflatable member disposed in the housing; a fluid coupler connected to the housing; and a one-way valve disposed in the housing and configured to permit a hardenable fluid to flow in a distal direction from the fluid coupler into the inflatable member and to prevent the hardenable fluid from flowing back in a proximal direction from the inflatable member into the fluid coupler; wherein at least a portion of the inflatable member is configured to expand through the at least one opening of the housing upon inflation of the inflatable member by the hardenable fluid.

In some embodiments, a spinal implant may include a housing including a proximal housing segment, an intermediate housing segment, and a distal housing segment; an inflatable member connected to the distal housing segment; the proximal housing segment including a fluid coupler; the proximal housing segment having a maximum outer dimension; the intermediate housing segment including at least one resilient member; the at least one resilient member being configurable in a compressed condition in which the at least one resilient member does not extend beyond the maximum outer dimension, and the at least one resilient member being biased toward an expanded condition in which the at least one resilient member extends beyond the maximum outer dimension; an inflation tube disposed within the housing and extending from the fluid coupler into the inflatable member; and a one-way valve disposed in the inflation tube and configured to permit a hardenable fluid to flow in a distal direction from the fluid coupler into the inflatable member and to prevent the hardenable fluid from flowing back in a proximal direction from the inflatable member into the fluid coupler.

In some embodiments, an apparatus may include a spinal implant including an inflatable member, a one-way valve configured to permit inflation of the inflatable member and to prevent deflation of the inflatable member, and a fluid coupler; an inflation cannula configured for removable connection to the fluid coupler and a pressurized source of hardenable fluid; an insertion tool configured for removable engagement with the implant; and a delivery cannula configured to removably receive the implant, the inflation cannula, and the insertion tool; wherein the inflation cannula is configured to inject the hardenable fluid through the one-way valve into the inflatable member to cause expansion of the inflatable member.

In some embodiments, a method of treating a vertebra may include creating an insertion path in the vertebra; inserting an implant into the insertion path, the implant comprising an inflatable member, a one-way valve configured to permit inflation of the inflatable member and to prevent deflation of the inflatable member, and a fluid coupler; connecting an inflation cannula to the fluid coupler; injecting a hardenable fluid through the inflation cannula, the fluid coupler, and the one-way valve into the inflatable member to expand the inflatable member within the vertebra; and disconnecting the inflation cannula from the fluid coupler.

In some embodiments, a method of treating a vertebra may include creating a first insertion path in the vertebra; inserting a first implant into the first insertion path, the first implant including a first inflatable member, a first one-way valve configured to permit inflation of the first inflatable member and to prevent deflation of the first inflatable member, and a first fluid coupler; connecting a first inflation cannula to the first fluid coupler; injecting a hardenable fluid through the first inflation cannula, the first fluid coupler, and the first one-way valve into the first inflatable member to expand the first inflatable member within the vertebra; disconnecting the first inflation cannula from the first fluid coupler; creating a second insertion path in the vertebra; inserting a second implant into the second insertion path, the second implant including a second inflatable member, a second one-way valve configured to permit inflation of the second inflatable member and to prevent deflation of the second inflatable member, and a second fluid coupler; connecting a second inflation cannula to the second fluid coupler; injecting a hardenable fluid through the second inflation cannula, the second fluid coupler, and the second one-way valve into the second inflatable member to expand the second inflatable member within the vertebra; and disconnecting the second inflation cannula from the second fluid coupler; wherein the first and second inflatable members are expanded sufficiently to be pressed against each other.

In some embodiments, a method of treating a spinal disorder or injury may include drilling a path that at least partially traverses two or more vertebrae; inserting an implant into the path, the implant comprising an inflatable member, a one-way valve configured to permit inflation of the inflatable member and to prevent deflation of the inflatable member, and a fluid coupler; connecting an inflation cannula to the fluid coupler; injecting a hardenable fluid through the inflation cannula, the fluid coupler, and the one-way valve into the inflatable member to expand the inflatable member within the two or more vertebrae; and disconnecting the inflation cannula from the fluid coupler.

In some embodiments, a spinal implant apparatus for intra-vertebral reduction and fixation of an osteoporotic fracture may include an expandable body including an inflatable member having an interior for receiving a hardenable fluid; a fluid coupling configured for detachable joining of the expandable body to an inflation cannula; an anchoring portion disposed generally about an outer surface of the fluid coupling and configured to be deployed from a contracted state to an expanded state to engage surrounding bone tissue in the expanded state; and a delivery instrument having a lumen containing the expandable body, the fluid coupling, and the anchoring portion in a distal portion of the lumen with the anchoring portion in the contracted state; wherein the fluid coupling is releasably engageable with a counterpart coupling of the inflation cannula within the lumen of the delivery instrument.

In some embodiments, a method for treating two adjacent osteoporotic vertebral body fractures and associated fracture deformity in a patient may include directing an access cannula into a first vertebral body; introducing a pre-curved guide pin into the access cannula and directing a tip of the pre-curved guide pin cephalad or caudad towards an adjacent vertebral body; further extending the guide pin into the adjacent vertebral body through an intervertebral disc between the first vertebral body and the adjacent vertebral body to form an access path; retracting and removing the guide pin from the access cannula; inserting a delivery cannula through the access cannula, the delivery cannula including a pre-curved distal portion; inserting a delivery assembly into the delivery cannula, the delivery assembly including (a) a CFD-KI prosthesis in its distal portion and (b) an inflation cannula and anti-rotation device apparatus in its proximal portion, the apparatus reversibly engaged to the CFD-KI prosthesis, the CFD-KI prosthesis including proximal and distal segmental balloon portions; directing the pre-curved distal portion of the delivery cannula including the CFD-KI prosthesis therein into the access path; retracting the pre-curved distal portion of the delivery cannula sufficiently to expose the CFD-KI prosthesis; and expanding the proximal and distal segmental balloon portions with hardenable fluid media within the first vertebral body and the adjacent vertebral body, respectively, with sufficient hydraulic pressure to differentially and directionally expand each of the first vertebral body and the adjacent vertebral body.

In some embodiments, a spinal implant may include an inflatable member; an expandable jacket disposed about the inflatable member; an inflation tube in fluid communication with the inflatable member; the inflation tube configured to direct a hardenable fluid into the inflatable member and thereby expand the inflatable member; wherein the expandable jacket is configured to control expansion of the inflatable member in one or more directions.

The above is a brief description of some of the features and advantages of some embodiments of the present invention. Other features, advantages, and embodiments of the invention will be apparent to those skilled in the art from the following description, accompanying drawings, and appended claims. It is intended that all such additional systems, methods, features, and embodiments be within the scope of the invention and encompassed by the appended claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIG. 37A is an axial cross-sectional view of a spinal vertebra illustrating transpedicular and parapedicular paths for implantation of a spinal prosthesis as described herein.

FIG. 37B is a sagittal cross-sectional view of the spinal vertebra of FIG. 37A.

FIG. 38 is a cross-sectional view of a guide pin installed in a vertebral bone.

FIG. 39 is a cross-sectional view of the guide pin of FIG. 38 and a first tissue dilator disposed about the guide pin.

FIG. 40 is a cross-sectional view of the guide pin and first tissue dilator of FIG. 39 and a second tissue dilator disposed about the first tissue dilator.

FIG. 44 is a cross-sectional view of the guide pin, obturator, and access cannula of FIG. 43, the inner cannula and intermediate cannula having been removed.

FIG. 45 is a cross-sectional view of the guide pin, obturator, and access cannula of FIG. 44 with a fastener and an insertion tool disposed within the access cannula and about the obturator.

FIG. 46 is a cross-sectional view of the guide pin, obturator, fastener, access cannula, and insertion tool of FIG. 45 showing the fastener in an installed position.

FIG. 47 is a cross-sectional view of the fastener, access cannula, and insertion tool of FIG. 46, the obturator and guide pin having been removed, and an implantable prosthesis disposed within the access cannula ready for insertion into the vertebral bone.

Figure 62:
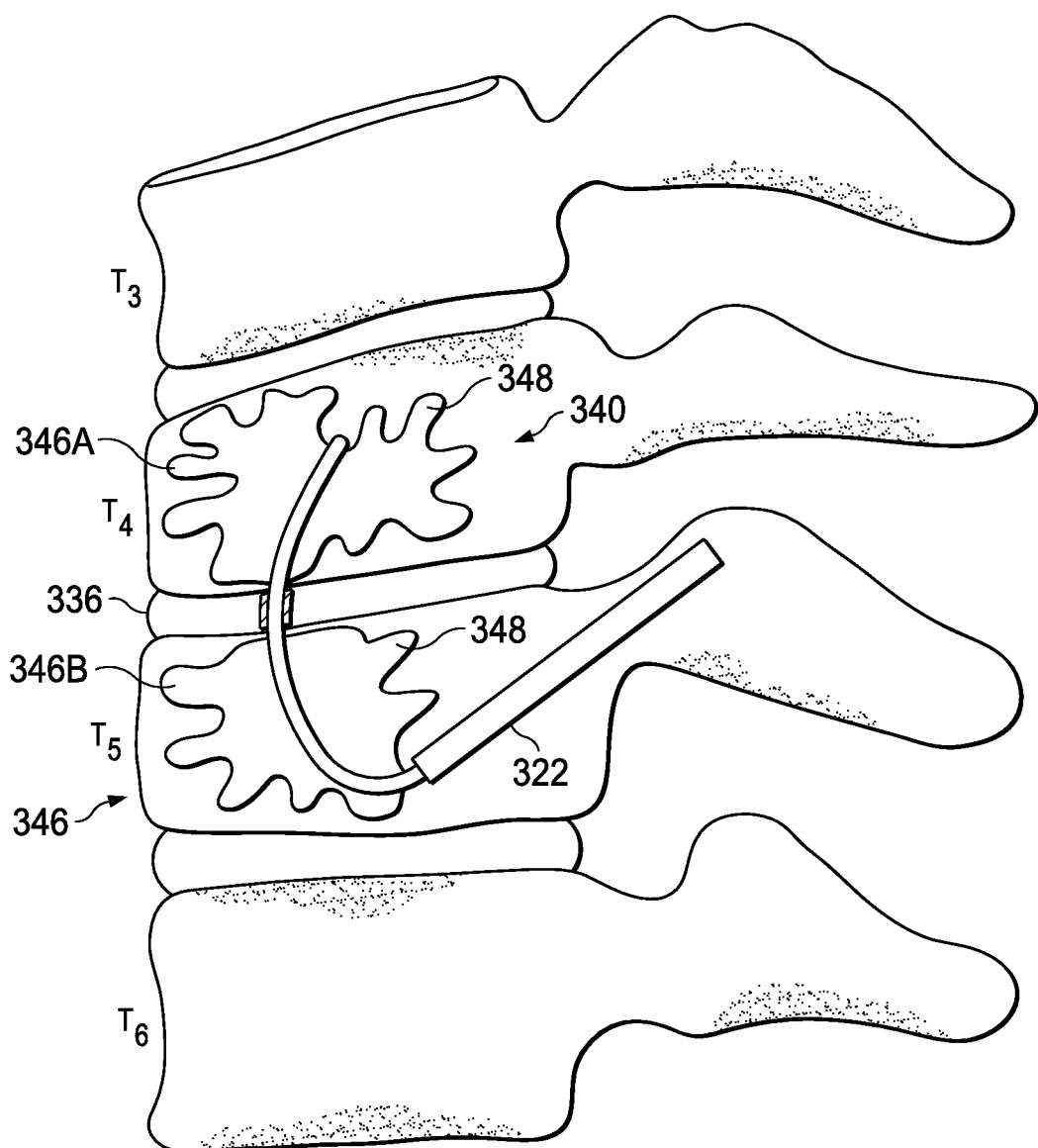
FIG. 62 is a schematic sagittal view of the T3-T6 level showing implantation and expansion of an alternative embodiment of a multilevel CFD-KI prosthesis in T4 and T5 having multiple protruding portions for improved fixation of the device to the vertebral bodies. Note the position of the CFD component at T5.
Figure 63:
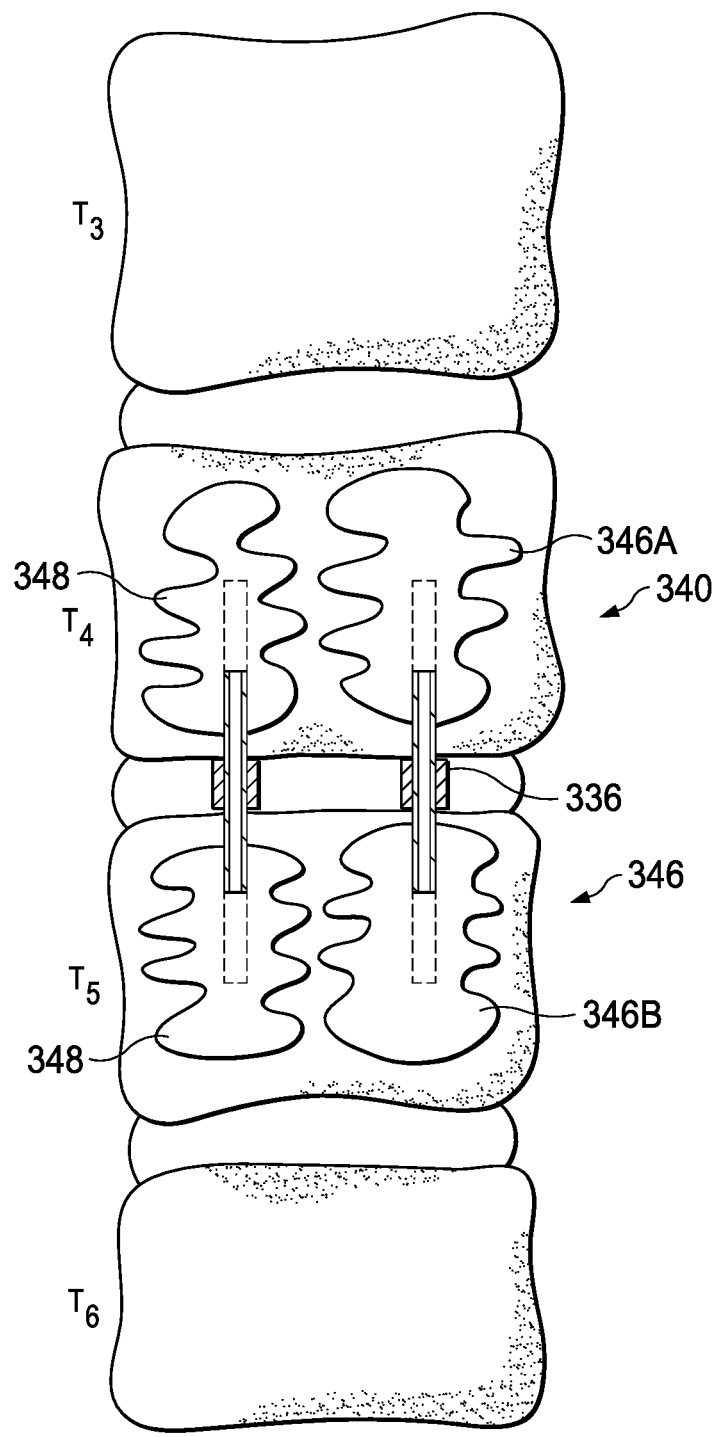

FIG. 63 is a schematic coronal view of the bilateral multilevel prostheses shown in FIG. 62.

Figure 64:
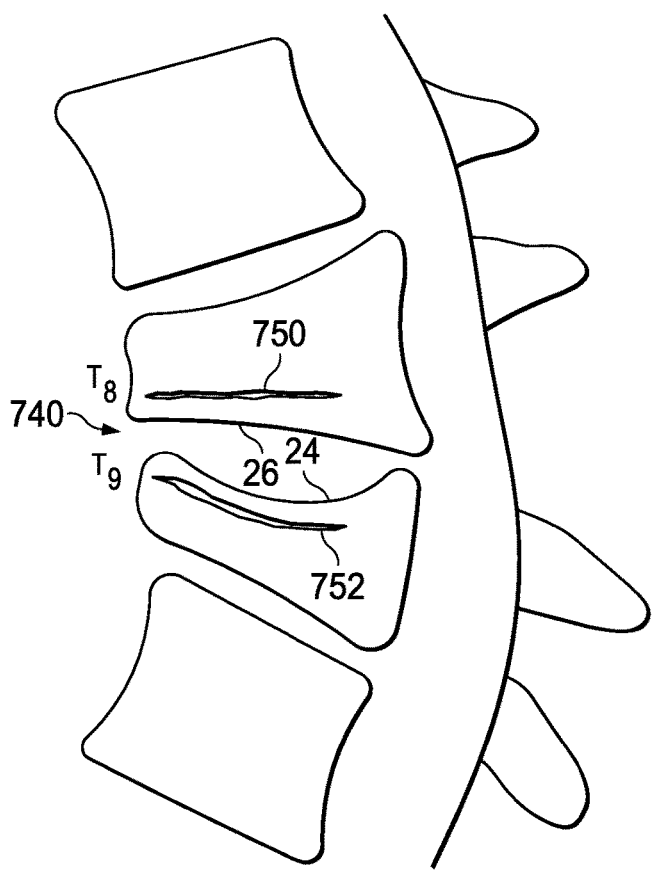

FIG. 64 is a schematic sagittal view at the T8-T9 level showing two contiguous osteoporotic vertebral body compression fractures involving the end plates, associated with kyphosis.

Figure 65:
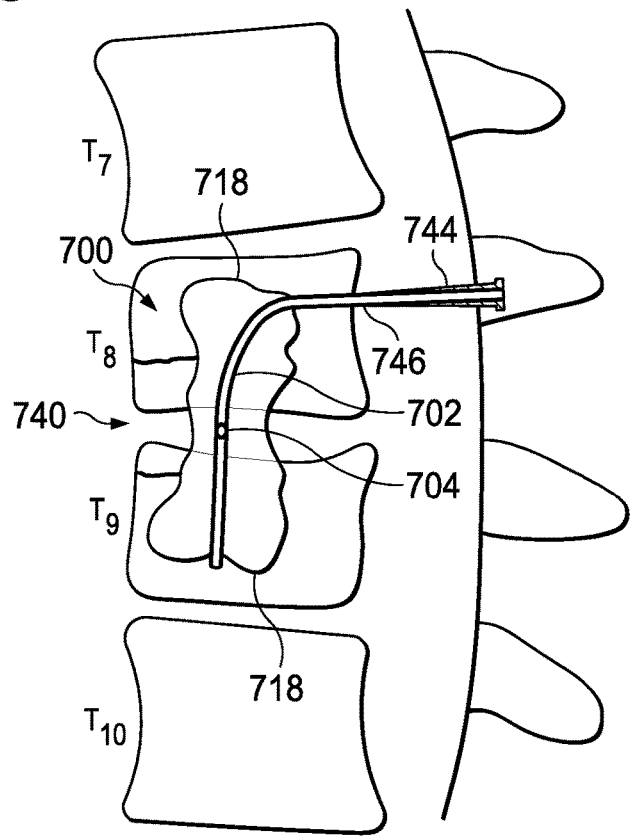

FIG. 65 is a schematic sagittal view similar to FIG. 64 following insertion of a multilevel CFD-KI prosthesis from the T8 level extending caudally to T9, crossing the T8-T9 disc. Note the lobulated single balloon extending through the disc level. Also note the fastener in the pedicle of the T8 vertebrae for improved fixation of the device.

Figure 66:
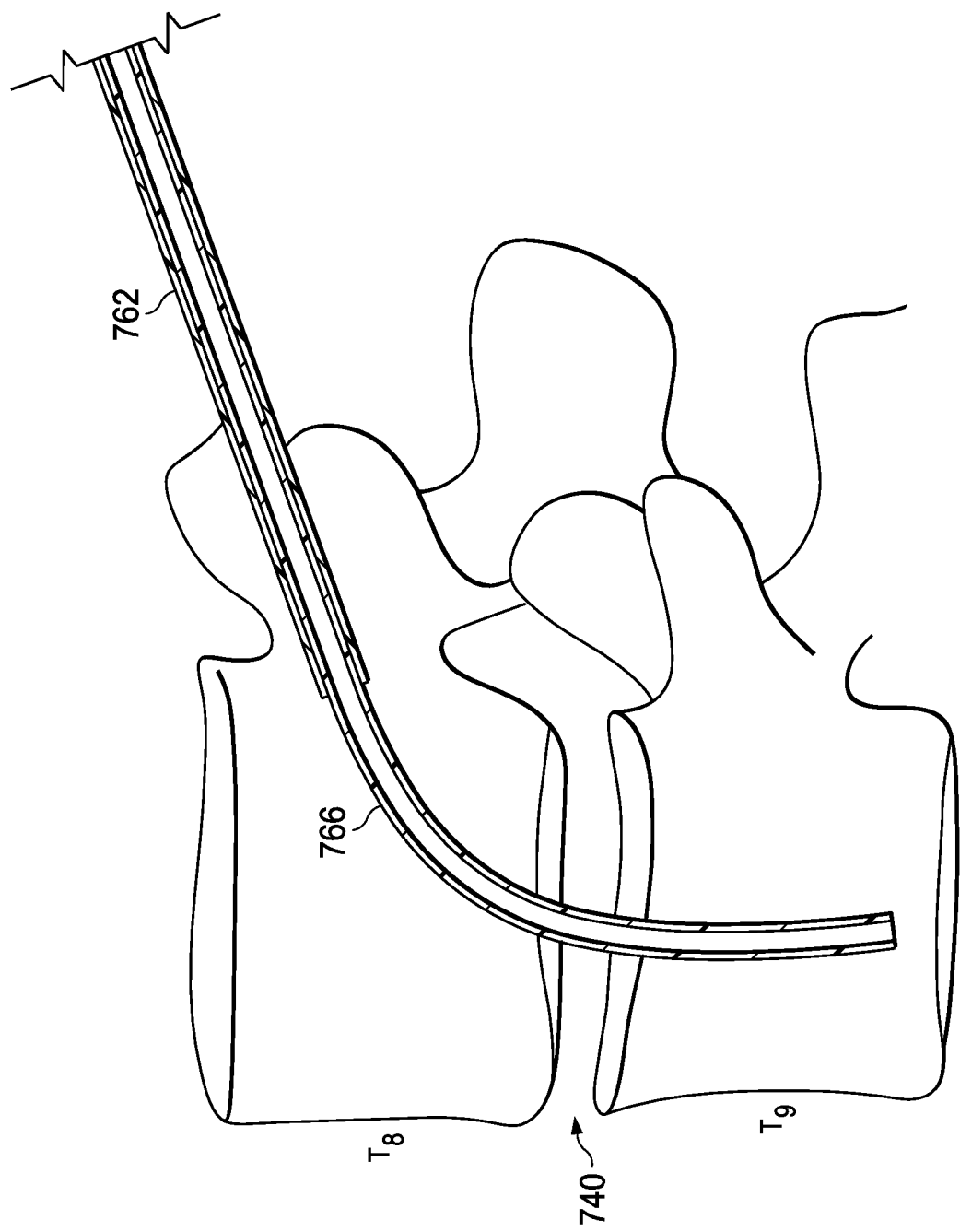

FIG. 66 is a side elevational view of two adjacent vertebrae illustrating an implantation method wherein a prosthesis deployment apparatus is employed to access an adjacent vertebrae through an intervertebral disc.

FIG. 67 is a side elevational view of a prosthesis deployment tool.

FIG. 68 is a partial side cross-sectional view of the prosthesis deployment tool of FIG. 67 including a pre-curved guide pin coaxially disposed in a lumen of a pre-curved access cannula, which in turn is disposed in a lumen of a straight guide cannula.

FIG. 69 is a partial side cross-sectional view of the prosthesis deployment tool of FIG. 67 including a centrally disposed pre-curved delivery cannula within a pre-curved access cannula, which in turn is disposed in the lumen of a straight guide cannula.

FIG. 70 is a schematic cross-sectional view of another embodiment of an inflatable spinal implant.

FIG. 71 is an enlarged cross-sectional view of the shaft of the inflatable spinal implant of FIG. 70 taken in the direction of section 71-71 as shown in FIG. 70.

DETAILED DESCRIPTION

The term implant is used broadly herein to include any foreign object which is inserted into the body.

As used herein, directional expansion refers to an expandable elastomeric implant or prosthesis having an expandable chamber in connection with a fluid source, the chamber defined by an elastic membrane having variable compliance in a specific direction whereby fluid pressurization of the chamber results in an expansion bias in the direction of the more compliant membrane portion.

As used herein, differential expansion refers to an expandable elastomeric implant having an expandable chamber in communication with a fluid source, the chamber defined by an elastic membrane having variable compliance wherein one wall of the chamber is more compliant than a contralateral wall of the chamber such that pressurized inflation of the chamber causes deflection or bending of the chamber in the direction of a strain limiting wall and away from a more elastically extensible wall. As the chamber is inflated, differential expansion occurs with the relatively thinner or more compliant wall section expanding more than the contralateral wall section.

As used herein, the term vertebral segment refers to two vertebrae having three articulations (the intervertebral disc and the two facet joints of the two vertebrae). The vertebral segment is generally described as having six degrees of freedom. It can rotate (in two directions) along three axes, resulting in flexion-extension (rotation around the left-right axis or X-axis), left and right lateral bending (around the sagittal axis or Z-axis), and left and right axial rotation (around the coronal axis or Y-axis); translational motion is also possible in the antero-posterior, left-right lateral, and up-down axial directions.

As used herein, the term inflatable member refers to a medical balloon or balloon membrane, used alone or in combination with an overlying or imbedded support structure such as a stent, fiber matrix, textile, mesh, etc.

Some embodiments of the present invention provide a multilevel implant or prosthesis for implantation within a vertebral segment of a patient suffering from at least two adjacent vertebral body fractures usually associated with kyphotic spinal deformity at this level.

Figure 1:
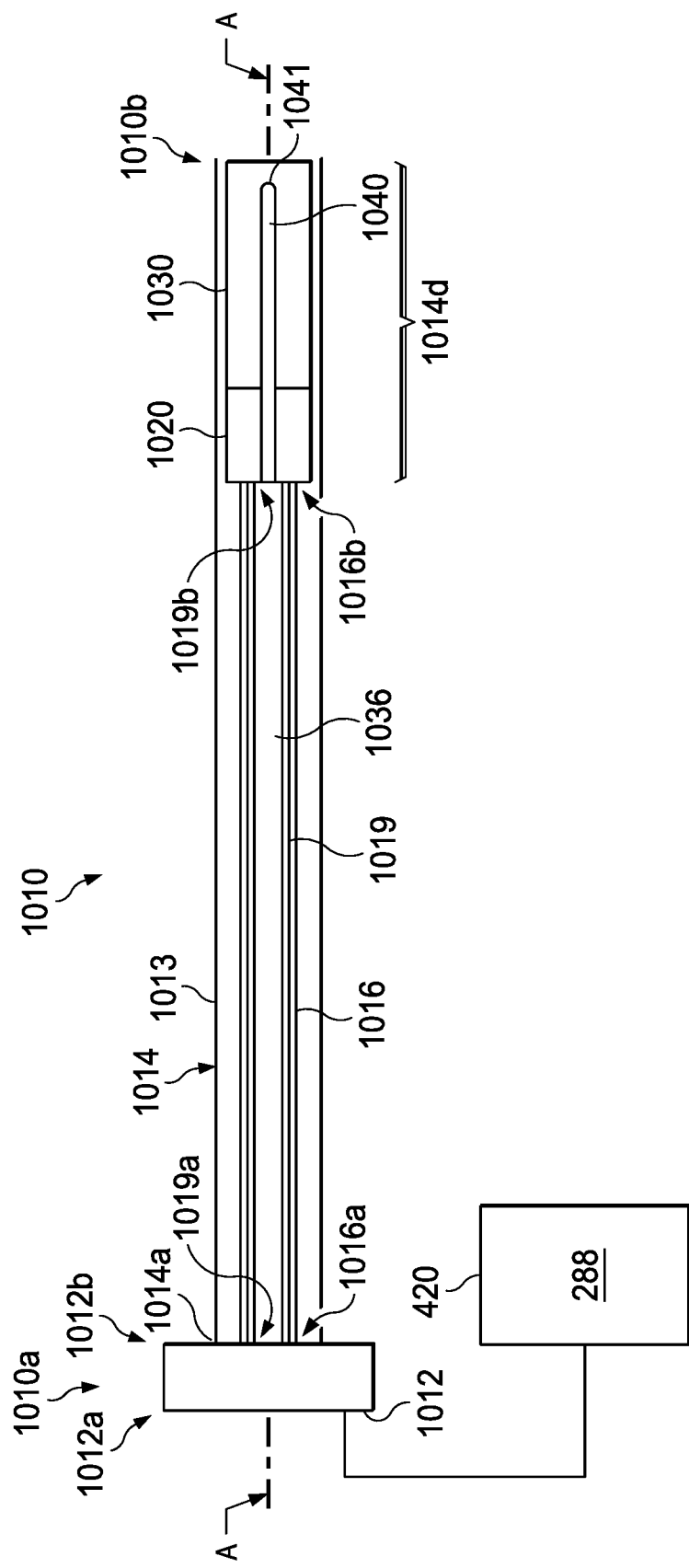
FIG. 1 is a schematic side view of a delivery apparatus for delivering a spinal implant having a connection fixation device (CFD).

FIG. 1 illustrates a customized kyphoplasty implant delivery apparatus 1010 for delivering a kyphoplasty implant (KI) 1030 to a site in a patient's spine. In some examples, the delivery apparatus 1010 may be sterilized by an ethylene oxide gas, radiation treatment (e.g., treatment with ebeam or gamma radiation), sterilization solution, any combination thereof, or other sterilization medium or procedure compatible with materials used in the kyphoplasty implant delivery apparatus. The delivery apparatus 1010 and the implant 1030 (which may include a CFD 1020 as shown) may be provided in separate kits, sterilized separately, and assembled at the time of the procedure. Alternatively, the entire assembly including the delivery apparatus 1010 and the implant 1030 may be provided in one package and sterilized together. A kyphoplasty implant 1030 together with a CFD 1020 is sometimes referred to herein as a CFD-KI assembly.

Although the present description is primarily focused on a kyphoplasty delivery apparatus 1010 that may be used for deploying a CFD-KI assembly, for example, in an osteoporotic vertebral fracture, other uses are possible. Accordingly, in some implementations, the delivery apparatus 1010 may be utilized to deploy, for example, an intervertebral disc implant. Other implementations may also be possible.

With further reference to FIG. 1, delivery apparatus 1010 may include a delivery cannula 1014 and may optionally include a handle 1012. The distal shaft portion 1014*d* of delivery cannula 1014 is shown as having a straight configuration. In some implementations, the distal shaft portion 1014*d* may be curved with one or more curves, and some implementations may include a distal shaft portion 1014*d* having one or more straight portions, one or more curved portions, or a combination thereof. In some implementations, the distal shaft portion 1014*d* may be manually or selectively steerable. By this method, the selected curved and/or straight portions may be propagated along the delivery cannula 1014 so that the delivery cannula 1014 largely conforms to the pathway selected. This configuration may allow the delivery apparatus 1010 to negotiate tortuous curves along a desired path through or around and between different components within a patient's body.

As seen in FIG. 1, an axis A-A may extend through the delivery apparatus 1010 from a proximal end 1010*a* to a distal end 1010*b*. The delivery apparatus 1010 may optionally include a handle 1012 having a proximal end 1012*a* and a distal end 1012*b*. Delivery apparatus 1010 may also include an inflation cannula 1019 having a proximal end 1019*a* and a distal end 1019*b*.

The proximal end 1014*a* of delivery cannula 1014 and the proximal end 1019*a* of inflation cannula 1019 may be reversibly coupled to handle 1012. The proximal end 1016*a* of anti-rotation device 1016 may be bonded or otherwise affixed to handle 1012, whereby rotation of handle 1012 about axis A-A by an operator results in an equal amount of rotation of anti-rotation device 1016 at its distal end 1016*b* where anti-rotation device 1016 reversibly engages the proximal end of CFD 1020. In some embodiments, anti-rotation device 1016 may be removably attached to handle 1012.

The proximal end 1019*a* of inflation cannula 1019 may be reversibly connected to handle 1012. A lumen or passage 1036 may extend from handle 1012 through inflation cannula 1019 to its distal end 1019*b* to provide a reversible fluid communication path with CFD 1020, allowing for inflation of an inflatable member 1046 (see FIG. 3) of kyphoplasty implant 1030 loaded within delivery cannula 1014.

In some embodiments, the presently disclosed apparatus and methods offer an improved alternative to the above described conventional kyphoplasty technique, which are advantageous, for example, by providing a kyphoplasty implant coupled to a connection fixation device at its proximal end that provides controllable pressurized inflation means and secure fixation and anchoring of the implant within the bone. Thus, the steps of conventional balloon inflation, deflation, and removal to create a void may be avoided. Instead, a delivery system as described herein carrying the CFD-KI assembly may be utilized to deploy, pressurize, expand, and anchor the CFD-KI assembly at the implantation site, thereby correcting the osteoporotic fracture deformity and stabilizing the vertebral segment, while avoiding the risk of inadvertent leakage of fluid hardenable media, and permit safe disconnection of the components at high inflation pressure.

Figure 2:
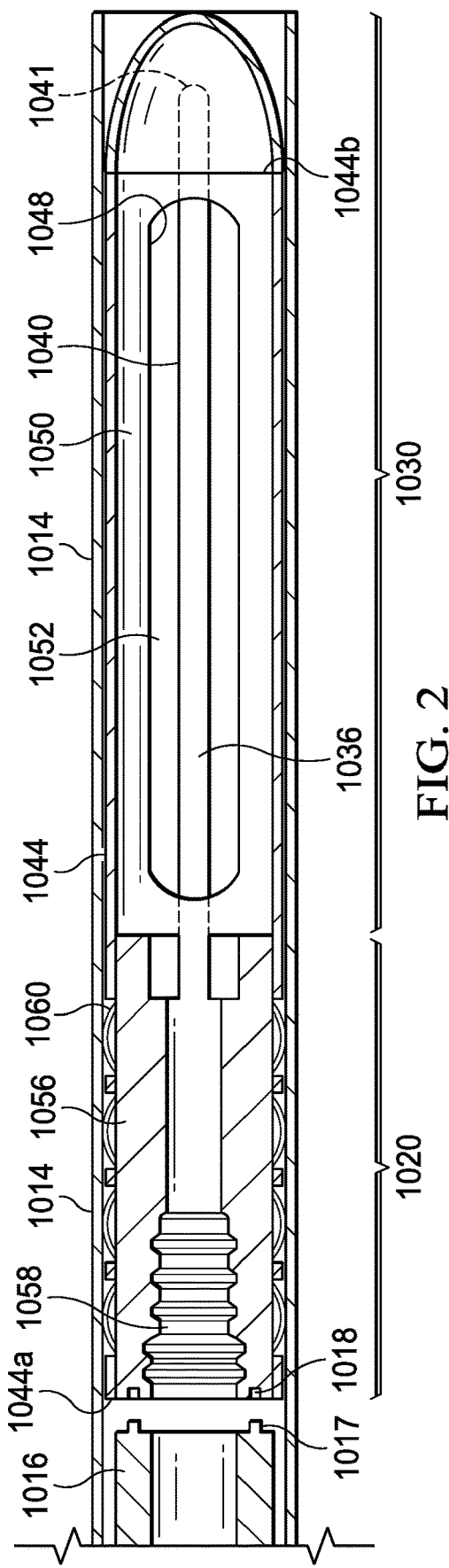
FIG. 2 is a top longitudinal sectional view of a distal shaft portion of the implant delivery apparatus of FIG. 1, including one embodiment of a CFD-KI device therein.
Figure 3:
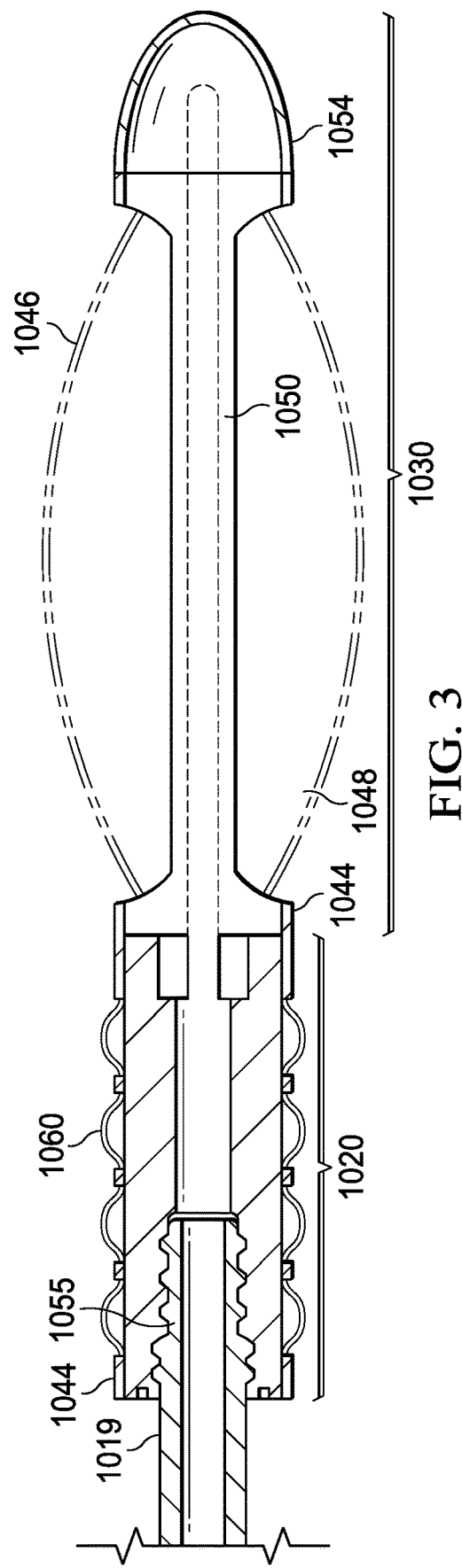
FIG. 3 is a side longitudinal sectional view of the distal shaft portion of the implant delivery apparatus of FIG. 2 wherein the delivery cannula has been withdrawn and the inflation cannula has been connected to the CFD.

In some implementations, referring to FIGS. 1-3, delivery apparatus 1010 may function in a manner that permits CFD 1020 and kyphoplasty implant 1030 (e.g., a CFD-KI assembly) to be removably attached to inflation cannula 1019 and anti-rotation device 1016 at distal ends 1019*b* and 1016*b*, respectively. Further, the distal portion 1014*d* of delivery cannula 1014 may retain the CFD-KI assembly and later deploy the CFD-KI assembly at, for example, a vertebral body to treat an osteoporotic fracture as described further below. Upon deployment of the CFD-KI assembly, the distal portion 1014*d* of delivery cannula 1014 may be retracted while the inflation cannula 1019 and the anti-rotation device 1016 are held stationary, the kyphoplasty implant 1030 is expanded by delivery of hardenable fluid 288 into the inflatable member 1046 through inflation cannula 1019, while the CFD-KI assembly is held in position by anti-rotation device 1016 and inflation cannula 1019. Specifically, protrusions 1017 of anti-rotation device 1016 may be engaged with corresponding recesses 1018 on shank 1056, and nozzle 1055 of inflation cannula 1019 may be engaged with socket 1058 of CFD 1020. The CFD-KI assembly then may be disengaged from inflation cannula 1019 by rotating the inflation cannula 1019 while holding the CFD-KI assembly stationary with the anti-rotation device 1016. This rotation (e.g., clockwise or counterclockwise, depending on whether the threads are right-handed or left-handed) may disengage nozzle 1055 of inflation cannula 1019 from socket 1058 of CFD 1020 (see FIGS. 3-7). Thereafter, the inflation cannula 1019, the anti-rotation device 1016, and the delivery cannula 1014 may be withdrawn.

The handle 1012 of delivery cannula 1014 may include an opening at its proximal face 1012*a* for introducing inflation cannula 1019. The distal face 1012*b* of handle 1012 may be securely attached (e.g., bonded) to a sheath 1013 and to the proximal end 1016*a* of anti-rotation device 1016 as shown in FIG. 1. With further reference to FIG. 1, along the distal face 1012*b* of handle 1012, sheath 1013 and anti-rotation device 1016 are shown to be concentrically disposed about axis A-A. Anti-rotation device 1016 may be bonded or otherwise affixed (either permanently or detachably) to handle 1012 at proximal end 1016*a*. Inflation cannula 1019 may exit the distal face 1012*b* of handle 1012 as shown at 1019*a* and may be slidable and rotatable through the opening of handle 1012. The handle 1012 may include a main port having a high-pressure valve (not shown) for connection of inflation cannula 1019 to a source 420 of hardenable fluid (HF) 288.

The handle 1012 and inflation cannula 1019 may function in a manner that permits communication of hardenable fluid HF from source 420 through inflation lumen 1036 of inflation cannula 1019 to the inner tube 1040 of the CFD-KI assembly. In some examples, the handle 1012 may function in a manner that permits or denies movement of the hardenable fluid HF into or out of inflation cannula 1019 towards inner tube 1040. In some embodiments, the HF may be pressurized to between about 10 and about 20 atmospheres, for example, but any suitable pressure may be utilized to inflate kyphoplasty implant 1030. In some implementations, a CFD 1020 may be connected to or part of a kyphoplasty implant 1030 such that when an inflatable member of implant 1030 is inflated with pressurized fluid HF, the risk of fluid leakage is reduced or eliminated. These implementations may reduce the likelihood that an inflation cannula 1019 may disengage prematurely or inadvertently from the CFD 1020 during pressurized inflation. Moreover, these implementations may immobilize the implant 1030 that has been expanded with hardenable fluid HF due to anchoring by CFD 1020 to surrounding firm tissue along the implantation path as explained in more detail below.

Referring again to FIG. 1, the customized delivery cannula 1014 may include a handle 1012 and a sheath 1013 that extends distally from the handle 1012. The sheath 1013 of delivery cannula 1014 may be constructed from a mid-to-high durometer material such that the sheath 1013, once inserted, does not collapse within the insertion path created in the bone. The sheath 1013 material can be a thin metal tube, for example, or a tube formed of high-density polyethylene having a low coefficient of friction to ensure that the CFD-KI assembly, anti-rotation device 1016, and inflation cannula 1019 move with ease through the lumen of sheath 1013. Alternatively, or additionally, a low friction coating can be applied to delivery cannula 1014. In yet other embodiments, the sheath 1013 may include braided or coiled structures formed from materials such as stainless steel wire, Nitinol, or other materials known in the art or later to be developed, to provide additional structural stability when needed. Generally, the sheath 1013 of delivery cannula 1014 should be of sufficient length to extend within the lumen of an access cannula (not shown) while the handle 1012 remains proximal to the access cannula. In some embodiments, a suitable length may be about 15 cm, for example; however, this should not be considered limiting, as the length of sheath 1013 may be less than or greater than 15 cm.

FIG. 1 further schematically illustrates a hardenable fluid source 420 containing a hardenable fluid 288 that is operatively connected to the front face 1012*a* of handle 1012 and reversibly but securely connectable to the proximal end of inflation cannula 1019. Though not specifically shown, in some embodiments handle 1012 of delivery apparatus 1010 may include a luer lock fluid connector in the alternative or in addition to a suitable proximal seal that may include, for example, a locking ring to proximally couple and seal the removable inflation cannula 1019 to a conduit carrying the hardenable fluid, which enables a user to disconnect the device easily from a female luer lock.

In operation, after creating the desired implantation path in the patient's bone, the guide pin or drill bit used to create the implantation path (see, e.g., FIGS. 38-47 and associated discussion below) may be removed, leaving the access cannula in the appropriate position to deliver the implant to the desired site. The delivery apparatus 1010 may then be back loaded, as a unit, into the lumen of the access cannula.

As shown in FIG. 1, inflation cannula 1019 may be coaxially disposed within the lumen of anti-rotation device 1016, and anti-rotation device 1016, in turn, may be coaxially disposed within the sheath 1013 of delivery cannula 1014. Inflation cannula 1019 and anti-rotation device 1016 may be custom sized and have distal ends, proximal ends, and lumens extending therebetween, and in some embodiments may be constructed as having three thin-layer walls. The exterior layer may be constructed of materials such as polyurethane, Nylon-11, Nylon-12, or PEBAX™ (Arkema, Inc., King of Prussia, PA), thermoplastic elastomers, copolymers, or blends, for example; the interior layer may be a liner made from a polytetrafluoroethylene (PTFE), nylon, or urethane with hydrogel coating, for example; and the mid-layer may be constructed from a braided material or a coiled member, such as stainless steel wire, Nitinol, or polyether ether ketones (PEEK) fibers, for example, to provide structural stability, especially to the inflation cannula 1019 and anti-rotation device 1016. The interior layer, or liner, may be extruded and placed upon a mandrel with the mid-layer and exterior layer respectively formed or otherwise placed over the interior layer. The layers may be laminated by a reflow process, for example, or other suitable manner of manufacture. Other layers may be heat shrunk and wrapped over the flexible inner layers for stability. In some embodiments, a superelastic coil such as Nitinol may be included to further increase rigidity of the cannulas (tubes) without compromising flexibility when needed. A polymeric layer may surround the superelastic coil or braid to reduce friction. In some embodiments, a lubricious material, such as HYROMED™ (AdvanSource Biomaterials Corp., Wilmington, Mass.) or a polyamide, for example, may be incorporated to reduce friction as the members 1019 and 1016 are rotated within delivery sheath 1013.

Referring to FIGS. 2 and 3, in some implementations the CFD-KI assembly may be loaded within delivery cannula 1014 and reconfigured from a low-profile delivery configuration shown in FIG. 2 to a deployed, expanded, securement configuration shown in FIG. 3. As shown, the CFD-KI assembly may include an elongate tubular housing 1044 that is sized to fit within a delivery cannula 1014 around 10 gauge in diameter, for example. Housing 1044 may be formed from a thin layer of material, such as a cannula or sheet of metal (e.g., stainless steel or Nitinol), that has been rolled into a cylinder, for example. By laser-cutting, etching, machining, stamping, otherwise cutting or forming, a plurality of elongate axial slots 1048 may be formed in housing 1044 to facilitate expansion of inflatable member 1046 outside housing 1044. In some embodiments, housing 1044 may have an outer diameter of approximately 4-8 mm, and a length of about 20-40 mm, for example. Of course, any suitable sizing may be used for housing 1044 and the other components described herein. An inner channel 1052 may extend longitudinally from a proximal end 1044*a* of housing 1044 to a distal end 1044*b* of housing 1044. The one or more slots 1048 may be bounded by one or more struts 1050.

The end cap 1054 is shown to have a nosecone shape, for example, but end cap 1054 may have other shapes that allow tracking of the kyphoplasty implant 1030 into a path created in trabecular bone by a guide pin or drill bit. The end cap 1054 may have a smooth, rounded leading end to facilitate insertion and movement through the insertion path. The end cap 1054 may be fabricated from a polymer having a firm durometer, such as 50-70 ShoreA, for example, or other suitable characteristics. In some embodiments, end cap 1054 may be formed in a mold having a mold cavity of corresponding shape. A rearward facing neck or relatively narrower portion of the base of end cap 1054 may be firmly inserted and bonded into the distal opening of housing 1044 and may be crimped firmly for secure bonding into a single, integral unit with respect to housing 1044, for example. The CFD 1020 may include an elongated cylindrical shank 1056 having an outside diameter selected such that the shank 1056 fits snugly into the lumen of housing 1044. Shank 1056 may include a threaded female socket 1058, for example, for fluid-tight connection to inflation cannula 1019 as will be described in more detail below.

Referring to FIGS. 4-7, the details of the fluid connector assembly will now be described. FIGS. 4-7 illustrate the details of an assembled (FIG. 4), partially assembled (FIG. 5), and disassembled (FIGS. 6 & 7) fluid connector assembly according to some embodiments of the present invention, which may include an inflation cannula 1019 including a threaded male nozzle 1055, anti-rotation device 1016, and a threaded female socket 1058. Inflation cannula 1019 may include a distally positioned nozzle 1055 (which may be integral to the rest of the cannula or separately molded) having a lumen 1036, which may be of the same caliber as the rest of the central lumen in the rest of the CFD 1020. The nozzle 1055 may be constructed from a polymeric material the same or similar to the material used in the rest of inflation cannula 1019, such as PEEK or PEBAX™, for example, or other suitable material. Alternatively, nozzle 1055 and socket 1058 may be molded from a thermoset material, such as silicone, or a thermoplastic material such as polyurethane, for example. An example of a polyurethane that may be used is CARBOTHANE™ (Lubrizol Advanced Materials, Inc., Cleveland, Ohio). The fluid connector components may be of relatively rigid design and may be constructed from a thermoset or thermoplastic material having a durometer ranging from about Shore 50 D to about 90 D, for example, or other suitable durometer. To promote smooth and frictionless rotation of nozzle 1055 within socket 1058, the surfaces may be polished to minimize irregularities from the molding and/or machining process. Highly polished surfaces may minimize inadvertent leaking of hardenable fluid at the connection at high inflation pressures and may facilitate uncoupling of the components at the end of the procedure.

Figure 4:
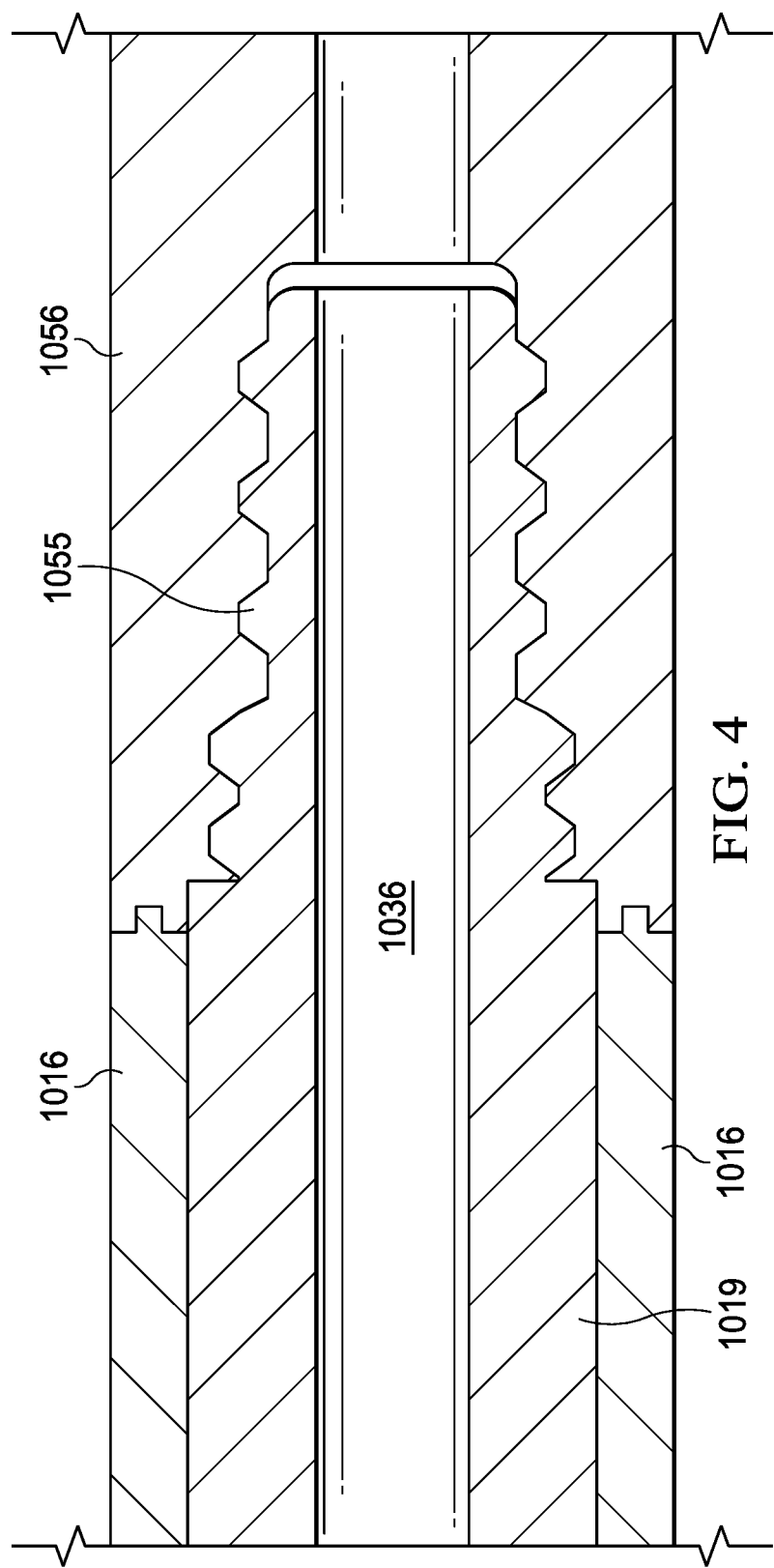
FIG. 4 is an enlarged longitudinal sectional view of a connector portion of the implant of FIG. 1 wherein the connector portion is engaged with an inflation cannula and an anti-rotation device.
Figure 5:
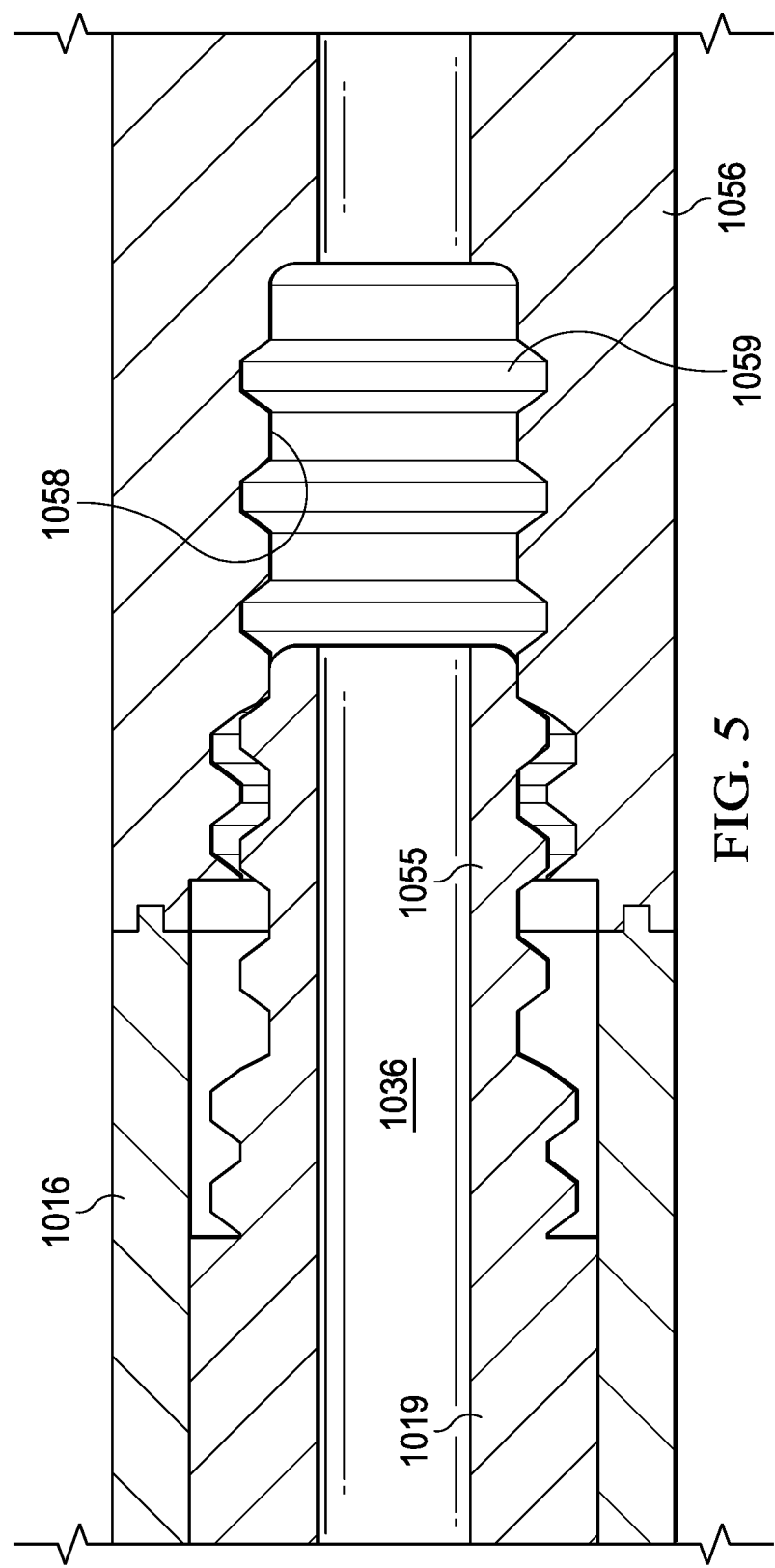
FIG. 5 is an enlarged longitudinal sectional view of the connector portion of the implant of FIG. 1 wherein the inflation cannula is partially withdrawn from the connector portion and the anti-rotation device is engaged with the connector portion.
Figure 6:
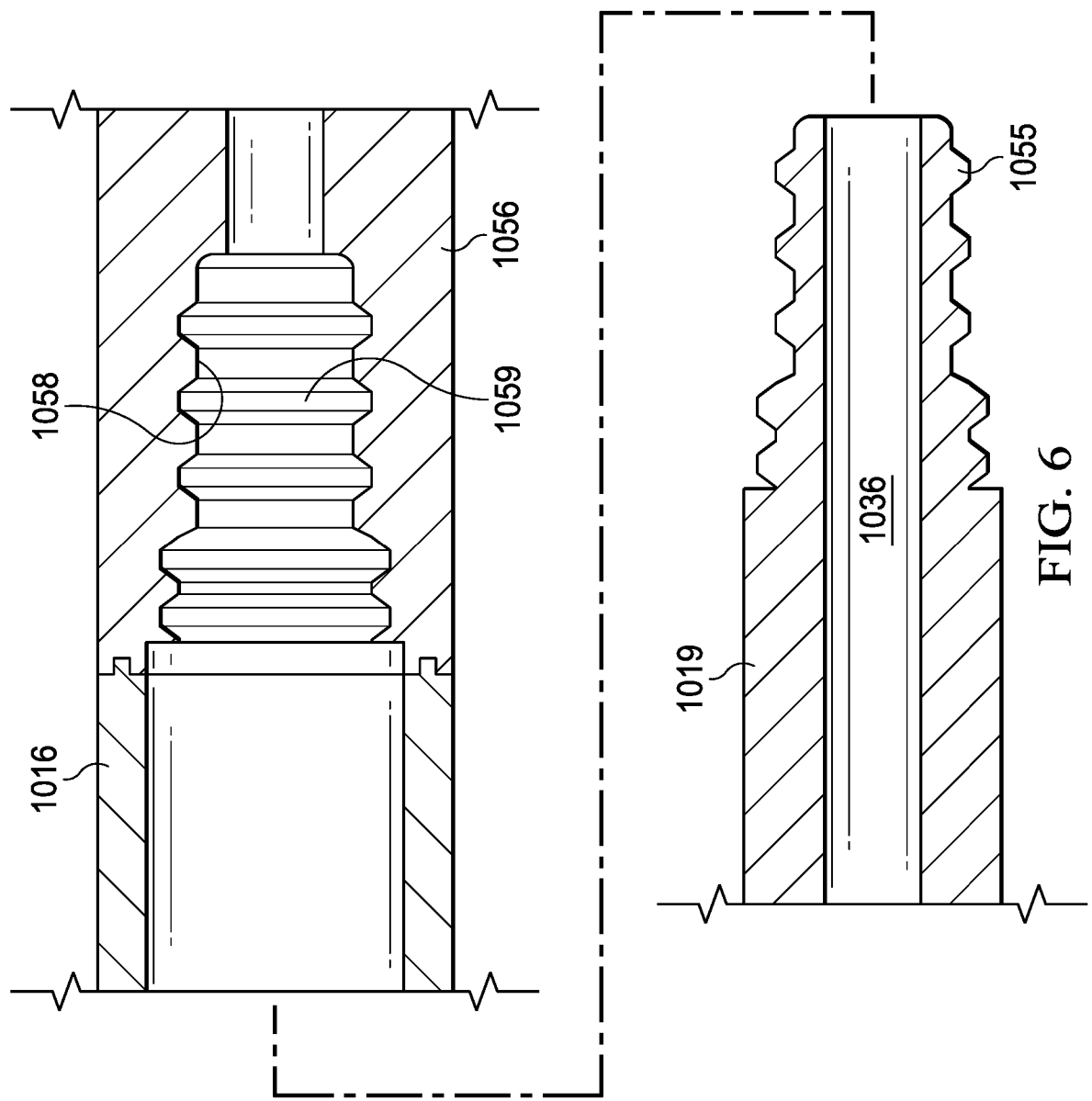
FIG. 6 is an enlarged, exploded longitudinal sectional view of the connector portion of the implant of FIG. 1 wherein the inflation cannula is fully withdrawn from the connector portion and the anti-rotation device is engaged with the connector portion.
Figure 7:
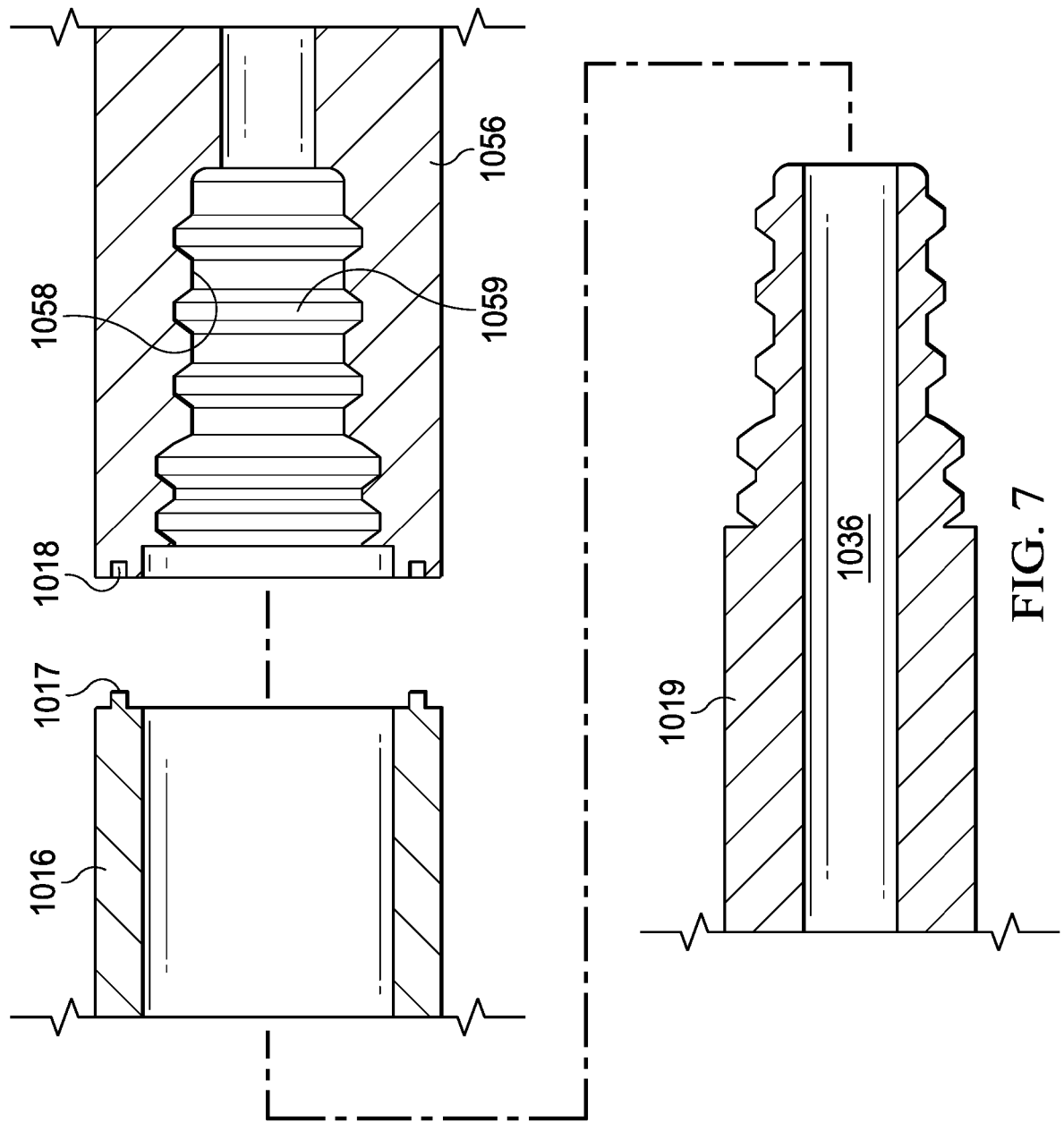
FIG. 7 is an enlarged, exploded longitudinal sectional view of the connector portion of the implant of FIG. 1 wherein the inflation cannula is fully withdrawn from the connector portion and the anti-rotation device is disengaged from the connector portion.

FIG. 4 illustrates the assembled connector components of the CFD 1020. Additional details of the connector can be seen. For example, while the diameter of the lumen 1036 may be constant in some embodiments throughout the length of the proximal and distal ends of the inflation cannula 1019, including nozzle 1055, an outer surface of nozzle 1055 may be generally discontinuous. The outer surface of nozzle 1055 may converge, or taper, such as in a frustoconical shape, distally from the transition point between the shaft of the inflation cannula 1019 and the tip of nozzle 1055. The length of the nozzle 1055 may range, generally, from about 5 mm to 10 mm and, more specifically, from about 4 mm when used in the thoracic spine and about 5 mm to about 11 mm when used in the lumbar spine, for example. These exemplary and non-limiting dimensions may be suitable to reduce the likelihood of disconnection or fluid leakage at high inflation pressures. Nozzle 1055 may have a central tubular portion which defines an axial bore or lumen 1036 having a generally circular cross-sectional configuration, for example. Of course, other suitable non-circular cross-sectional shapes may be used in some embodiments. Lumen 1036 may be substantially of uniform shape and diameter, for example, as it extends distally to terminate at the blunt tip 1041 of inner tube 1040 of implant 1030 (see, e.g., FIGS. 1 and 2). The female connector may include a cylindrical shank 1056 having a threaded female socket 1058, for example. In some embodiments, the female connector may be formed as a one-piece molded polymeric part, for example. The threaded male nozzle 1055 may project axially outward from the distal end of inflation cannula 1019. The threaded male nozzle 1055 may be adapted to mate in a threaded fashion with threaded female socket 1058 as shown. In some embodiments, the threaded male nozzle 1055 may include a single, continuous, tapered helical thread being narrower at the tip as compared with the base. Specifically, the tip may have a narrower lead-in section, and the base may have a wider friction-locking section. Thus, the male and female locking members of the fluid connector may be securely, threadably engaged so that leakage of fluid is avoided even at high pressures. Further, unintentional disengagement of the fluid connector components is unlikely, whereas intentional disengagement is quick and easy.

In some examples, a fluid connector having threads of increasing pitch may be used. In other examples, a male component of the connector may include two adjacent sections of male threads, the first section having a smaller width or diameter than the second section. The female component of the connector may include a socket with female receiving threads. The socket also may have two opening sections of varying diameters. The sections of the female component may each be configured to threadably engage the respective threaded sections of the male component. In some embodiments, the female component of the fluid connector may be on the inflation cannula 1019, and the male component of the fluid connector may be on the CFD 1020.

In some implementations, CFD 1020 may function in a manner that permits controlled disengagement from the distal shaft 1019b of inflation cannula 1019. Further, the distal shaft 1019b of inflation cannula 1019 may be connected to the CFD 1020 during the procedure prior to insertion into the lumen of delivery cannula 1014.

Female socket 1058 may include a central passage 1059. Nozzle 1055 may include a central passage 1036. When components 1055 and 1058 are connected, fluid may flow from lumen 1036 of inflation cannula 1019 through the central passage of nozzle 1055 towards the lumen of central tube 1040. Nozzle 1055 may be free to move rotationally but not longitudinally within central passage 1059 of socket 1058.

In some embodiments, the threaded nozzle 1055 may include a single continuous helical thread defined by three main axial sections: (i) a relatively narrow lead-in or tip section; (ii) an intermediate section; and (iii) a friction-locking base section. In some embodiments, the threaded fluid connector components 1055 and 1058 may be molded separately from polymeric material, for example, or other suitable material.

In use, to engage inflation cannula 1019 with CFD 1020, nozzle 1055 may be introduced into central passage 1059 of socket 1058. Continued threaded advancement of nozzle 1055 into socket 1058 may create an engagement between the male and female threads at the intermediate section, at which time the tip may begin to frictionally engage the root of the socket thread. Further threaded advancement of the nozzle 1055 into central passage 1058 may cause the friction-locking section at the base to move into full engagement with its counterpart socket thread, which may result in tight frictional locking of the male and female threads which may prevent inadvertent disengagement of the components even at high fluid pressurization. Further, because of the tight frictional fit of the threads, inadvertent fluid leak at high pressure may be prevented.

In some embodiments of the present invention, the nozzle 1055 may have a generally conical shape and may feature a variable thread pitch towards its tip, with the size increasing gradually from its tip to its base. This increase may be continuous and incremental at each thread and may vary between 0.01 and 0.1 mm per thread, for example. Of course, other suitable thread configurations may be employed.

Figure 8:
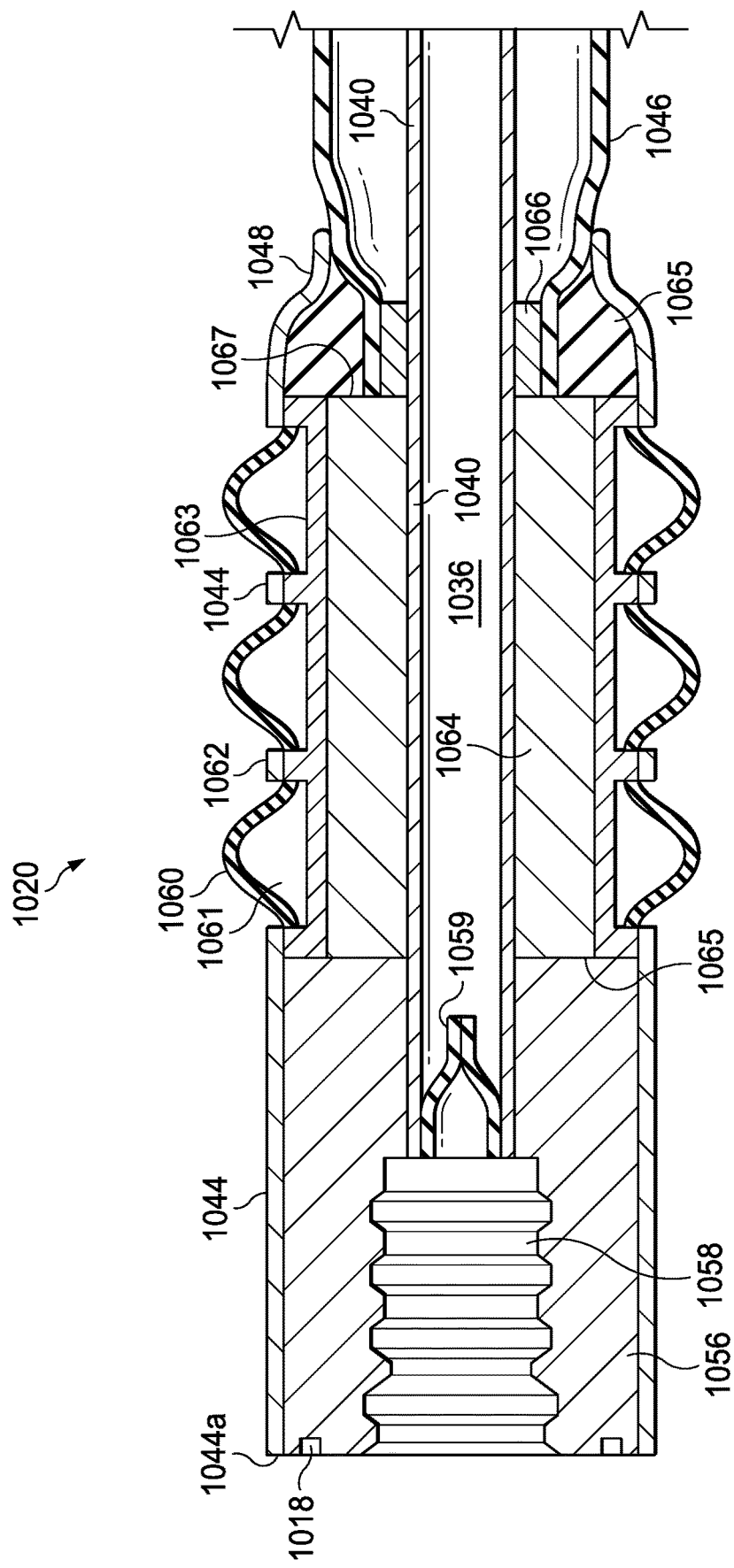
FIG. 8 is an enlarged longitudinal sectional view of an embodiment of a CFD showing one example of expandable arms as anchoring means around the middle section of the CFD that are preformed and biased into an outwardly bowed configuration.
Figure 9:
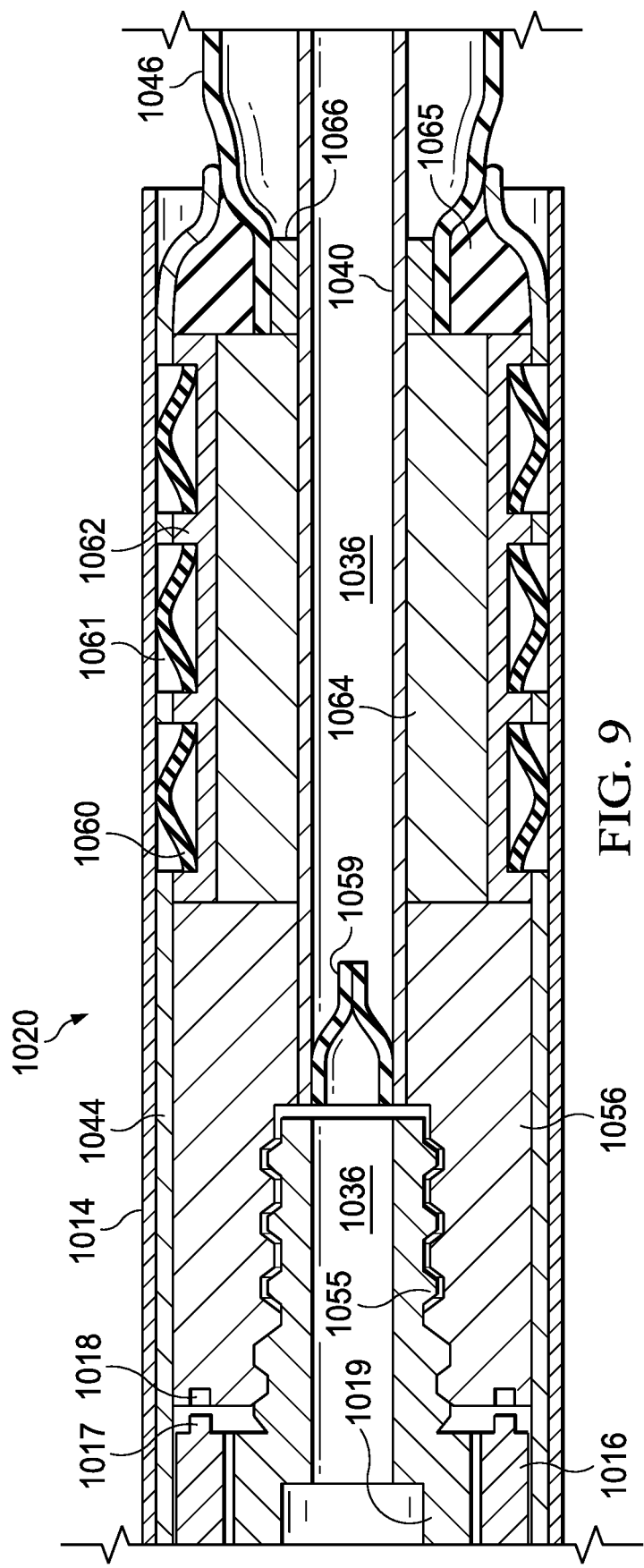
FIG. 9 is an enlarged longitudinal sectional view of the CFD of FIG. 8 loaded in a distal portion of a delivery cannula and showing flattening of the expandable arms to fit inside the delivery cannula.

With reference to FIGS. 8 and 9, one aspect of the disclosure provides a connection fixation device 1020 including a housing 1044 which is shared with kyphoplasty implant 1030. In some embodiments, CFD 1020 may include three separate sections that are described as follows: (i) a proximal section which provides fluid connection/disconnection means to the kyphoplasty implant 1030 and engagement/disengagement means between inflation cannula 1019 and anti-rotation device 1016 apparatus and a proximal face of CFD 1020; (ii) an intermediate section which provides anchoring means of CFD 1020 for fixation of the CFD-KI assembly to the bony trabeculae of the fractured vertebra or other bone in which the CFD-KI assembly is inserted; and (iii) a distal section that fixedly joins inflatable member 1046 of the kyphoplasty implant 1030 to the CFD 1020. In some implementations of the present invention, the anchoring means may surround substantially the entire outer surface of CFD 1020. In some examples, the anchoring section may occupy a recessed portion of housing 1044 and may define a slight peripheral gap in the housing between the proximal connection section and the distal mounting section. This slight gap may be useful for ease of folding of the anchors during insertion of the CFD-KI assembly into the lumen of a delivery cannula 1014. Further, the manufacturing process may be simplified.

The intermediate section of CFD 1020 will now be described in more detail. In this illustrated embodiment, at least two sets of expandable arms 1060 that are preformed and biased into an outwardly bowed configuration are arranged in a series of rows around the circumference of the intermediate section of CFD 1020. When uncovered by sliding delivery cannula 1014 proximally, the expandable arms 1060 may expand outwardly into close fit opposition to bone trabeculae along the implantation path for fixing the CFD-KI assembly in position within the bone.

In the embodiment of FIGS. 8 and 9, the outwardly expanded arms 1060 may be compressed into a low profile within a series of slots 1061 formed in a circumferentially recessed section of housing 1044. A plurality of perforated bridges 1062 may be configured to retain arms 1060 pinned down at the bases of slots 1061. The arms 1060 may be formed of a shape memory material which may be a wire or flat ribbon having a sinusoidal configuration, for example. Two examples of such a material are spring steel and the shape memory metal known as Nitinol. Of course, other suitable materials and shapes may be employed. The arms 1060 may thus be biased outward when flattened and compressed into slots 1061 and retained by perforated bridges 1062. In some embodiments, the outwardly expanded arms 1060 may be flat metallic strips that are twisted axially, bent into a sinusoidal configuration, and intermittently firmly retained in perforated bridges 1062. Such flat metallic strips may have widths ranging from about 0.005 to about 0.050 inches (0.127 to 1.270 mm), for example, or between about 0.015 and about 0.030 inches (0.381-0.762 mm), for example. Of course, other sizes and configurations may be employed. In some embodiments, four or more rows or sets of arms 1060 may be arranged circumferentially around the intermediate anchoring section. The flat metallic strips may be strong enough to exert a close fit interface with the bone to hold the CFD-KI assembly in place and yet thin enough to allow flattening or retraction into a low profile to fit within the lumen of delivery cannula 1014 as shown in FIG. 9. In other embodiments, arms 1060 may be round, oval, hemispherical, or have other cross-sectional configurations as needed or desired.

In the arrangement shown in FIGS. 8 and 9, perforated bridges 1062 may be integral to a circumferential band 1063 portion of housing 1044 or may be manufactured separately and attached or permanently welded or bonded to the band 1063 in a later step, for example. Band 1063 and bridges 1062 may be formed of a suitable polymeric or metallic material similar to housing 1044, for example. However, this may not be necessary, as the components may be manufactured separately in different manufacturing steps and subsequently assembled by suitable attachment means, such as welding, bonding, mechanical fastening, or otherwise. A tubular or cylindrical polymeric insert 1064 may be interposed concentrically between inner tube 1040 and circumferential band 1063. Insert 1064 may be formed of a polymeric material the same or similar to cylindrical shank 1056 (which includes female socket 1058) and may be attached or bonded thereto at interface 1065. Alternatively, shank 1056 and insert 1064 may be molded together in one integral component.

Turning now to the distal section of CFD 1020 shown in FIGS. 8 and 9, the distal section of CFD 1020 serves to attach CFD 1020 to kyphoplasty implant 1030 to form the CFD-KI assembly. In this particular embodiment of the CFD-KI assembly, housing 1044 may taper distally into a funnel-like configuration towards elongate axial slot 1048 of housing 1044. The proximal portion of inflatable member 1046 may be interposed and firmly bonded and/or crimped between an inner mounting portion 1066 and an outer mounting portion 1065. The bonded structure may then be operatively secured within the confines of the tapered distal housing portion 1044 and supported centrally by inner tube 1040. Inner mounting portion 1066 and outer mounting portion 1065 may function as polymeric inserts and may be bonded to cylindrical polymeric insert 1064 at interface 1067.

Figure 10:
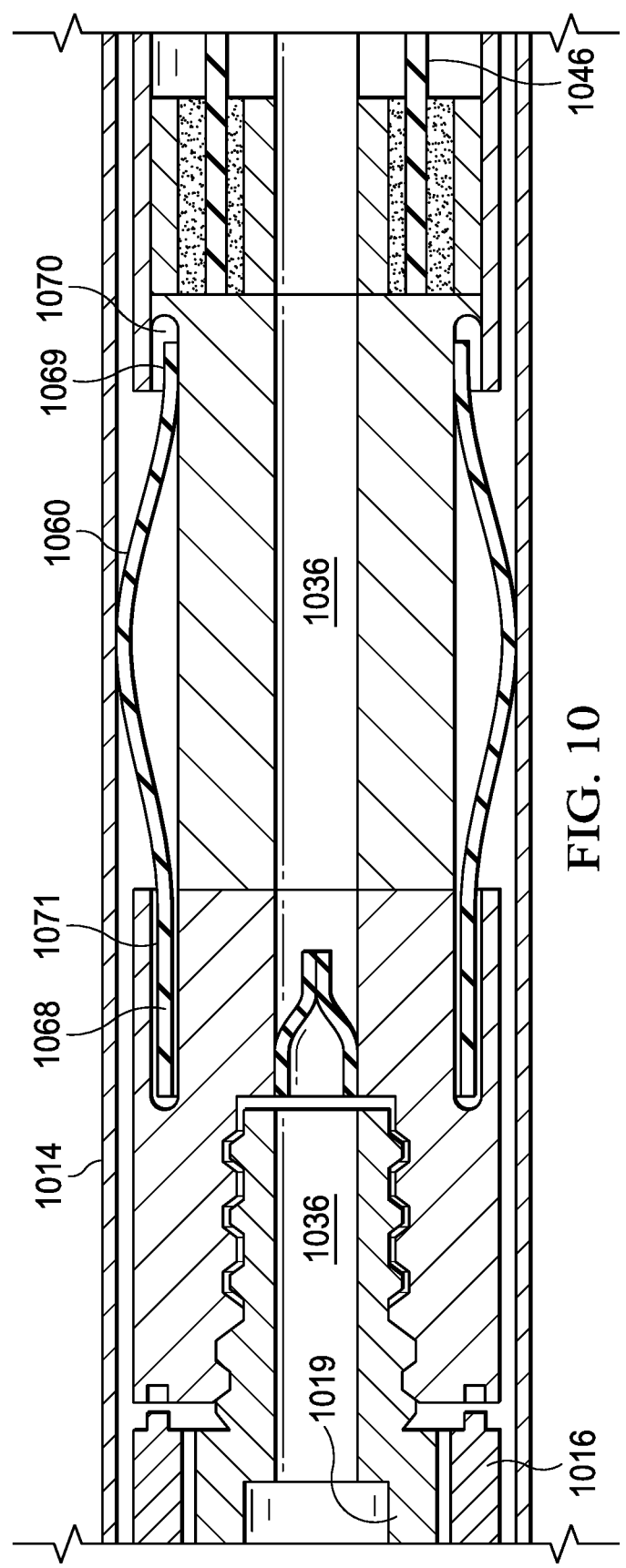
FIG. 10 is a partially exploded longitudinal sectional view of an alternative embodiment of a CFD having expandable arms in a contracted position within a delivery cannula.
Figure 11:
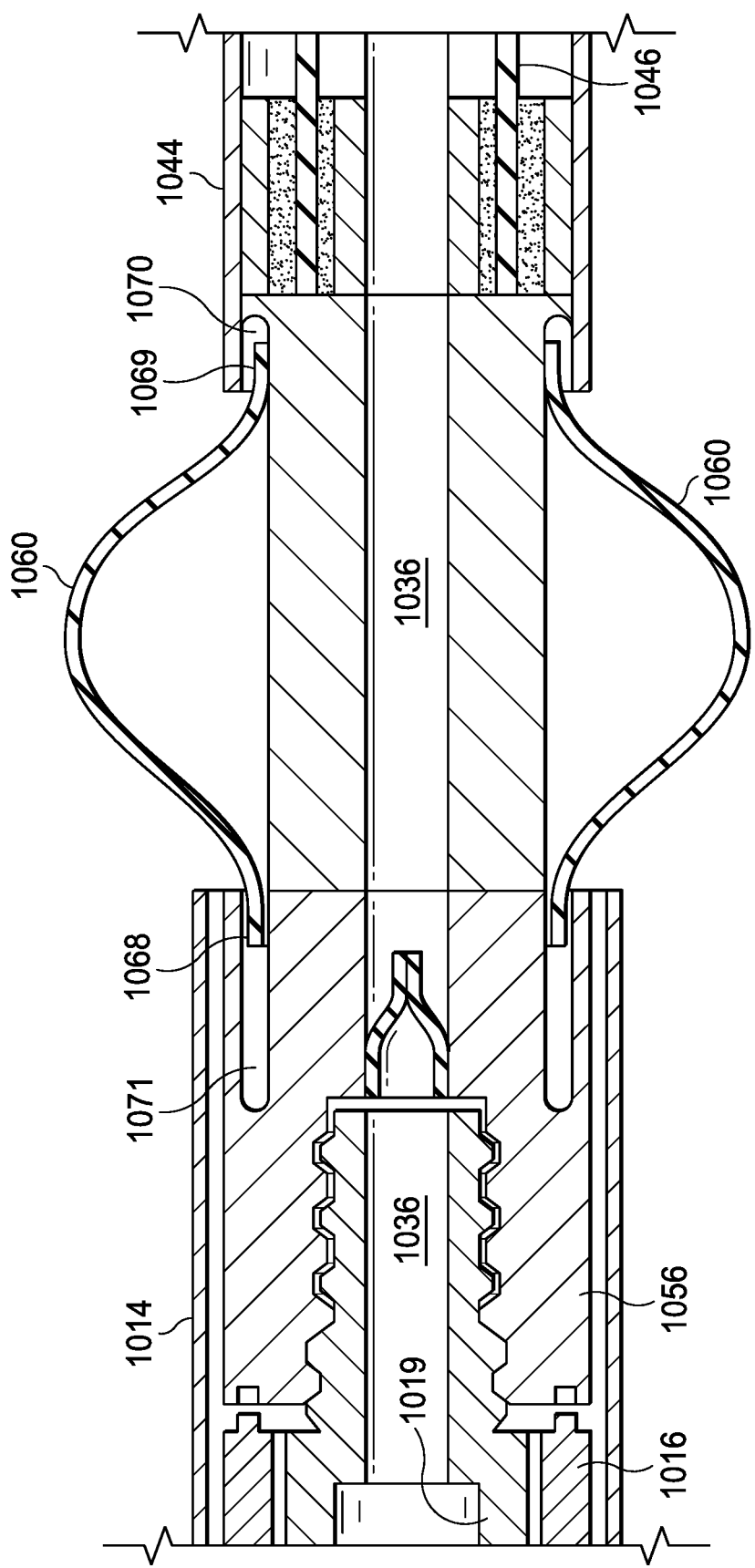
FIG. 11 is a partially exploded longitudinal sectional view of the CFD of FIG. 10 showing expansion of the expandable arms following retraction of the delivery cannula.

Referring to FIGS. 10 and 11, an alternative arrangement for expandable and contractable arms 1060 is shown. In this embodiment, the distal ends 1069 of arms 1060 are fixedly mounted in slots 1070, and the proximal ends 1068 of arms 1060 are slidably mounted in slots 1071. Thus, arms 1060 may be compressed to fit within delivery cannula 1014 as shown in FIG. 10, and arms 1060 may be biased to expand outward into bone structure as shown in FIG. 11 when the delivery cannula 1014 is moved proximally. Because the expandable arms 1060 are anchored or attached at one end only and are free to slide axially at the other end, the arms 1060 retain their flexibility and an increased degree of outward bowing while remaining attached at one end. This configuration may also result in ease of manufacturing as there are fewer connections to be made in assembling the CFD components. In FIG. 10, the expandable arms 1060 are constrained by the overlying delivery cannula 1014, and the distal ends 1068 of arms 1060 have been advanced deeper into slots 1071. In this embodiment, the expandable arms 1060 are free to expand outwardly to a more marked degree upon release from their constrained configuration as shown in FIG. 11. In FIG. 11, the proximal ends 1068 of arms 1060 have retracted somewhat within slots 1071, whereas distal ends 1069 of arms 1060 are stationary in slots 1070 as they are firmly attached in this position. Because the distal ends 1069 are held in position in distal slots 1070 and the proximal ends 1068 are movable in proximal slots 1071, arms 1060 are able to bow outwardly in accordance with the amount of movement of proximal ends 1068 within proximal slots 1071, while firm attachment of the arms 1060 distally prevents undue rotation of the arms 1060 about their longitudinal axes.

Figure 12:
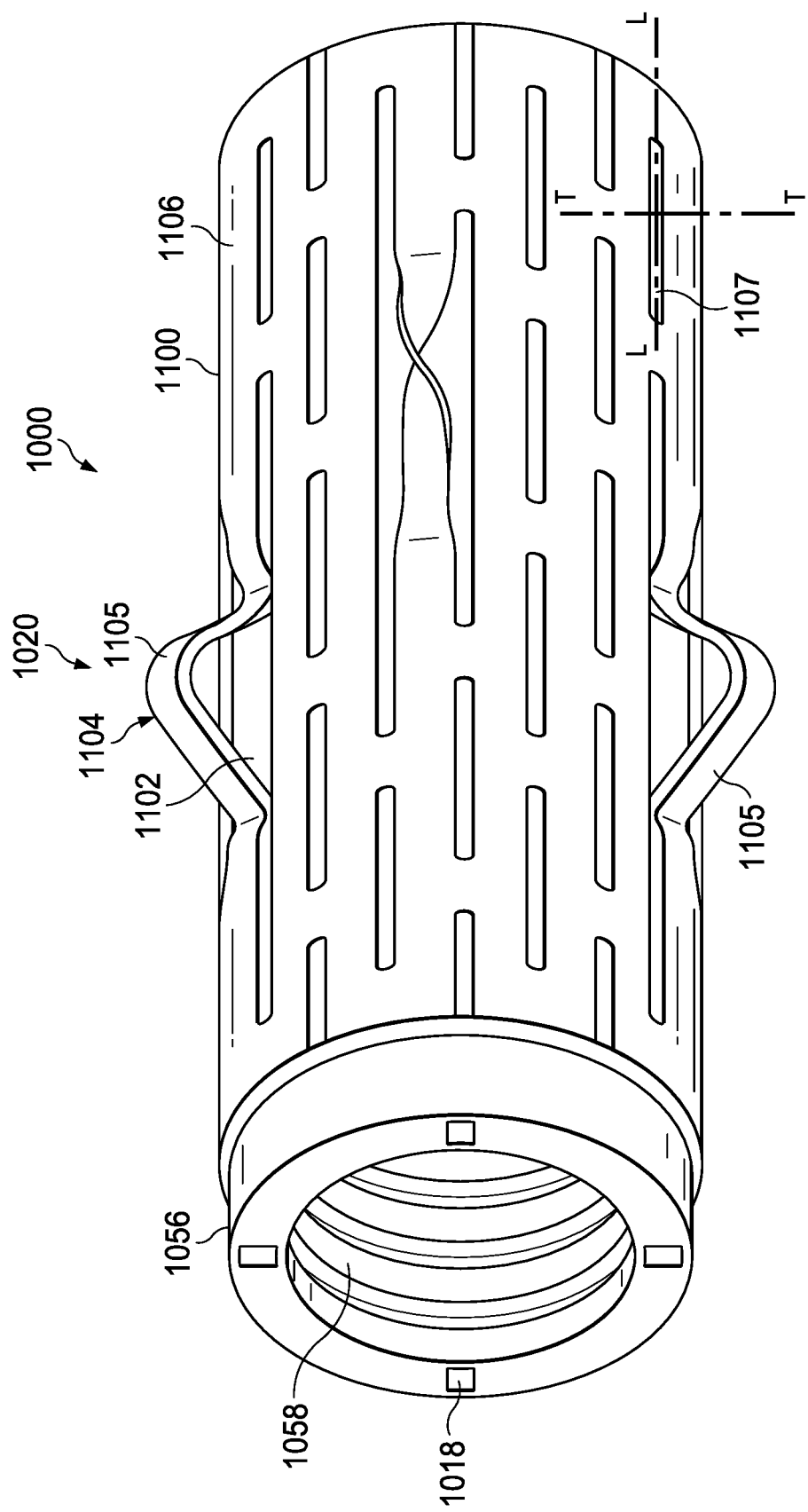
FIG. 12 is an enlarged perspective view of another embodiment of a CFD showing an anchoring component surrounding a connection component wherein the anchors of the anchoring component exhibit outward twisting.

FIG. 12 illustrates an embodiment of a connection fixation device CFD 1020 wherein the fixation or anti-migration feature is a tissue engagement stent (TES) 1000. TES 1000 may include modifications on the type of stent implanted in a variety of body lumens or vessels such as within the vascular system, urinary tract, or airways, for example. However, unlike conventional stents, TES 1000 may be neither self-expanding nor balloon expandable in the traditional sense. Rather, TES 1000 may be applied over or around the outer surface of housing 1044, for example, such as in a recessed groove that may include the anchoring section of CFD 1020. Therein, TES 1000 may be welded, bonded, or otherwise attached to the housing 1044. A plurality of openings 1102 may be formed in the wall 1100 of TES 1000 to define a plurality of flexible anchors 1104 that may protrude outwardly under tension and that may be collapsed back into the openings 1102 for ease of loading into the lumen of a delivery cannula 1014.

In some implementations, TES 1000 may include a reticulated hollow tube 1106 which defines a plurality of cells 1107. Similar designs have been used in other stents, such as those shown in U.S. Pat. No. 5,449,373 to Pinchasik et.al. and U.S. Pat. No. 5,695,516 to Fischell, for example, which may be employed for TES 1000. TES 1000 may be formed through any suitable means, including laser or chemical milling, for example. In such processes, a hollow cylindrical tube is milled to remove material and form open cells 1107. The cells 1107 may have a major longitudinal axis L-L and a transverse minor axis T-T. A plurality of peaks and valleys, struts, linking members, and turns may be formed as needed or desired. In some embodiments, an anchor 1104 may engage two peaks of adjacent struts within an opening 1102. Thus, in some embodiments, the entire length of the anchor 1104 may be between two adjacent struts or linking members, and in other embodiments only a portion of the length of the anchor 1104 may be between two adjacent struts or linking members. A protruding region 1105 may form a peak of anchor 1104.

Figure 13:
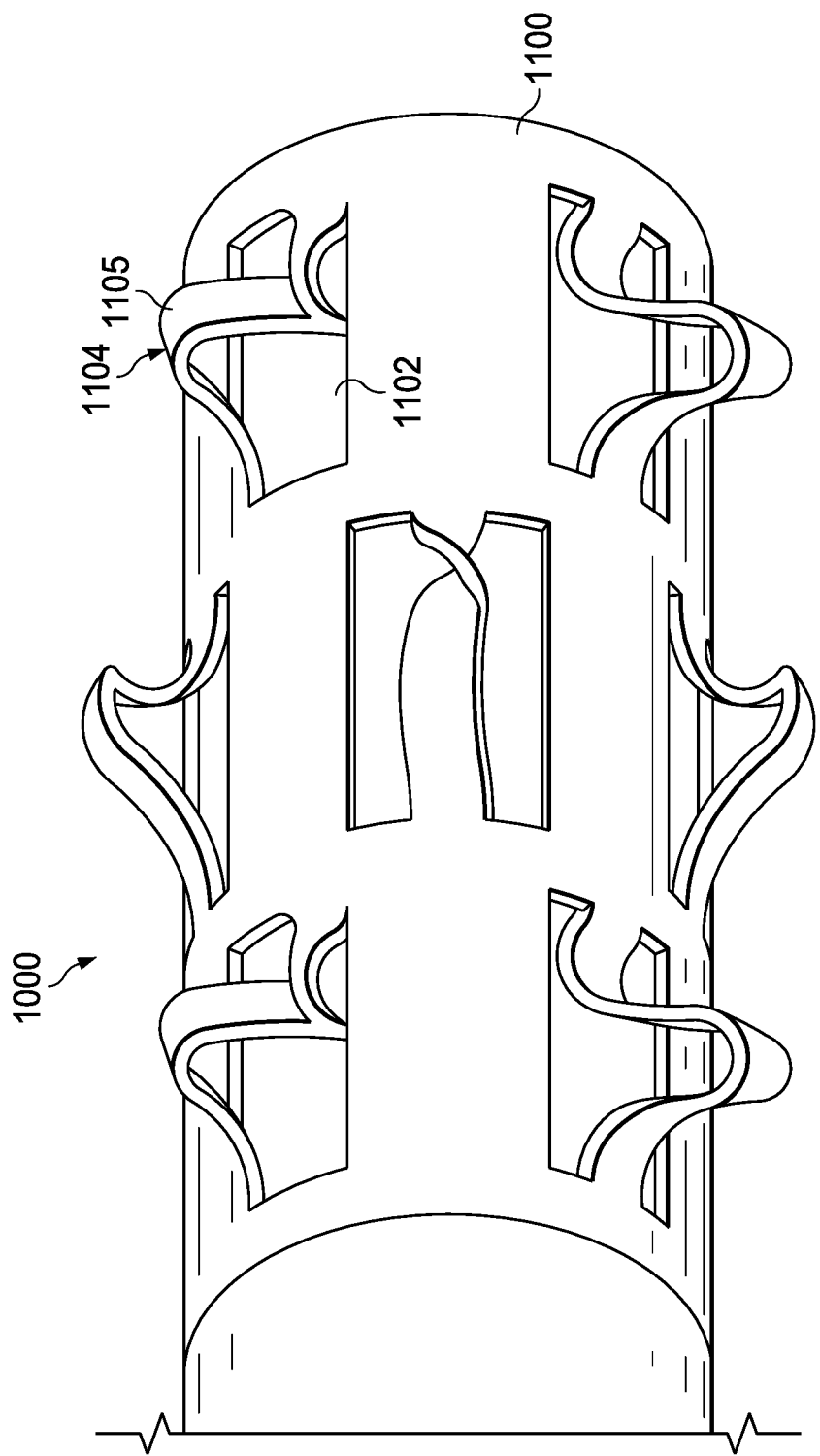
FIG. 13 is an enlarged perspective view of another embodiment of a CFD demonstrating a tissue engagement stent (TES) portion having a plurality of anchors of different shapes, sizes, and orientations.
Figure 14:
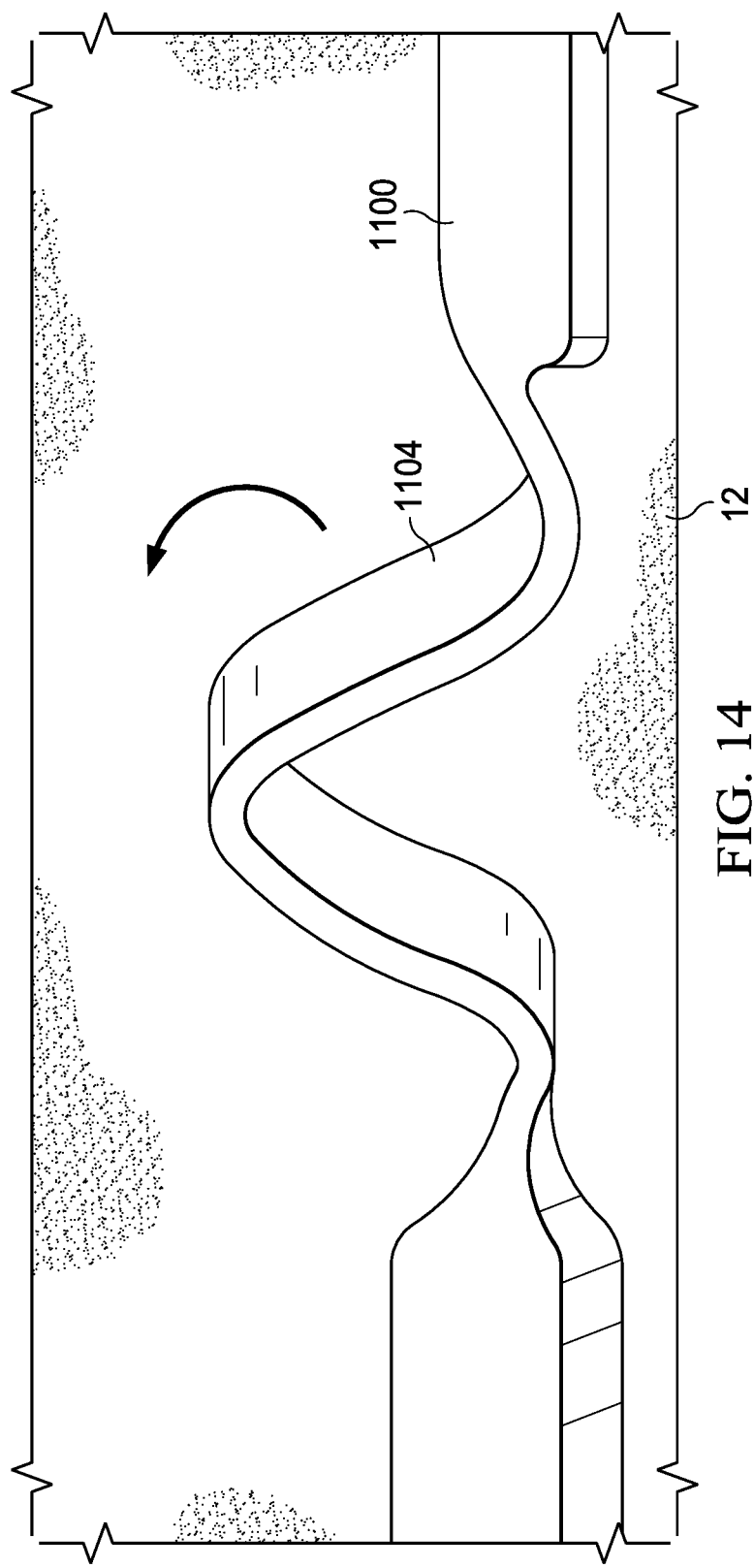
FIG. 14 is an enlarged perspective view of an anchor of a CFD having a rounded design in a twisted configuration for fastening the implant in a bone and preventing micromotions from taking place.
Figure 15:
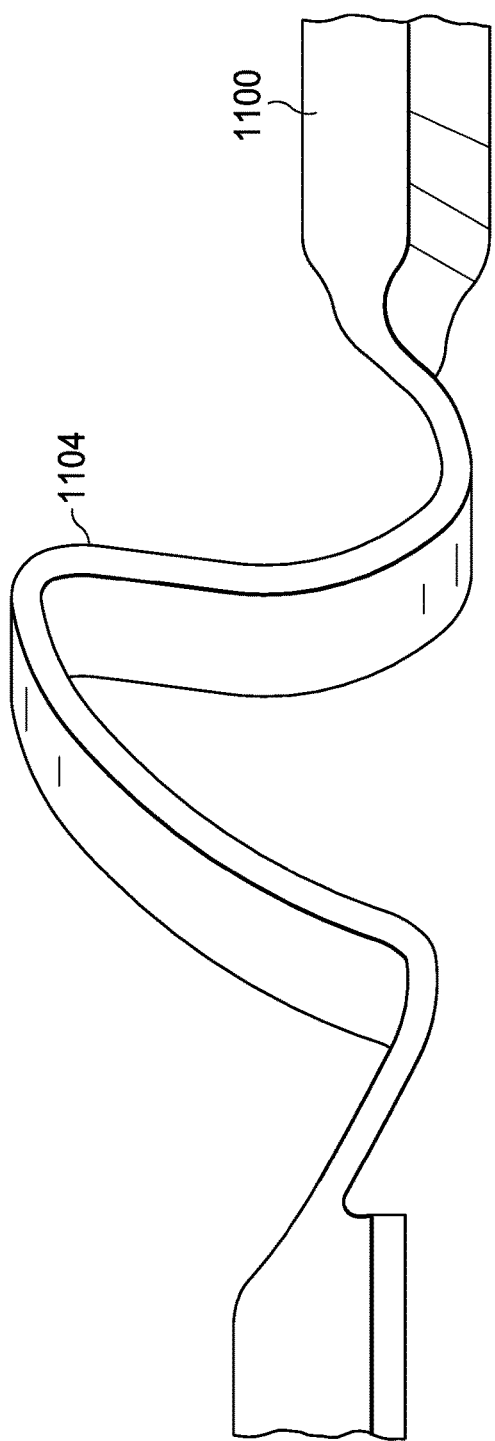
FIG. 15 is an enlarged perspective view of an anchor of a CFD having a wave design and a straight portion that projects to the right of the figure and a curved portion to the left.
Figure 16:
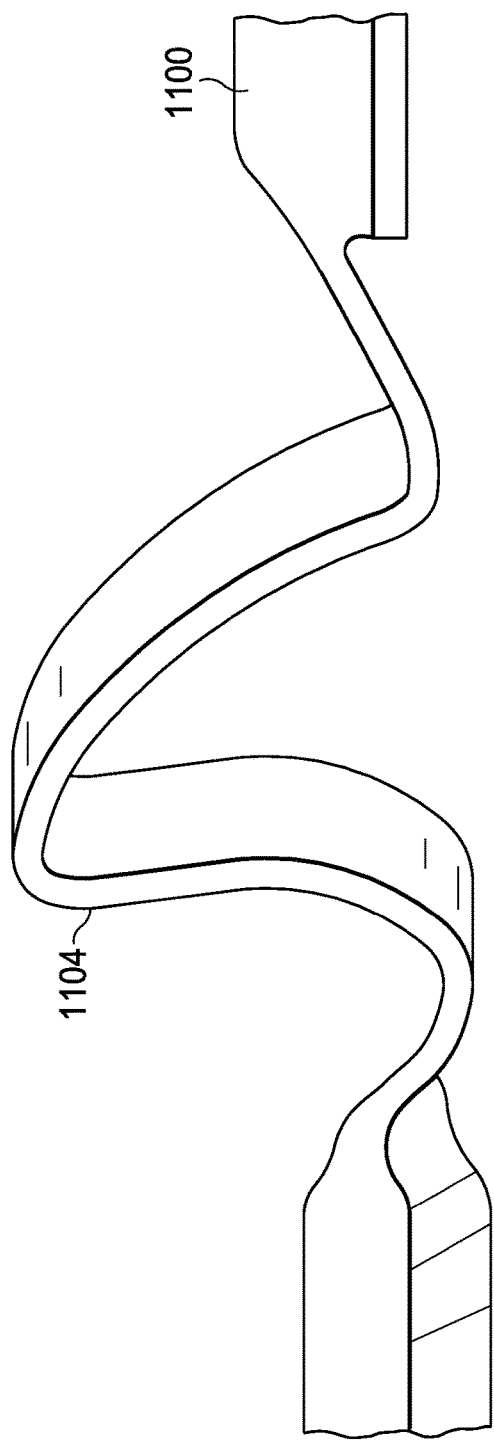
FIG. 16 is an enlarged perspective view of an anchor of a CFD similar to FIG. 15 except that the straight portion of the anchor projects to the left, and the curved portion projects to the right.

FIG. 13 shows an example of a TES 1000 with all of its anchors 1104 in an expanded state to secure CFD 1020 in surrounding tissue. FIGS. 14, 15, and 16 illustrate several exemplary embodiments of anchors 1104 in various configurations. Anchor 1104 in FIG. 14 is shown embedded in cancellous bone 12.

A variety of metallic materials, superelastic alloys, and preferably Nitinol in some embodiments, are suitable for use in TES 1000, but other materials may also be employed. In some embodiments, desired characteristics of the materials may include that they be suitably springy even when fashioned into very thin sheets. Various stainless steels which have been physically, chemically, and otherwise treated to produce such desirable properties are suitable, as are other metal alloys such as cobalt chrome alloys (e.g., ELGILOY™ available from Elgiloy Specialty Metals, Elgin, Ill.), platinum/tungsten alloys, and especially nickel/titanium alloys generically known as "Nitinol," for example. Nitinol may be preferred for some embodiments because of its physical properties and its significant history in implantable medical devices. A notable property of Nitinol is that it is non-ferromagnetic and is compatible with magnetic resonance imaging (MRI) processes. Further, Nitinol has a relatively high strength to volume ratio. This may allow the anchors 1104 to assume a thinner profile which may facilitate compaction into openings 1102 and loading of the CFD-KI assembly into delivery cannula 1014. Spring tempered stainless steels and cobalt-chromium alloys such as ELGILOY™ are also suitable, as are a wide variety of other known "superelastic" alloys. Other materials suitable for the TES 1000 may include certain polymeric materials, particularly engineering plastics such as thermotropic liquid crystal polymers (LCP's), for example. These polymers are high molecular weight materials which can exist in a so-called "liquid crystalline state" wherein the material has some of the properties of a liquid in that it can flow but it retains the long-range molecular order of a crystal. These materials are particularly suitable when augmented or filled with fibers such as those of metals or alloys, for example.

With reference to FIGS. 17-19 and FIG. 12, in some embodiments the TES 1000 structure may also include barbs 1110, 1112, 1114 depending from wall 1100 that are twisted, shaped, and configured to point radially outward. An anchoring barb tip structure 1116, 1118, 1120 may be configured to twist and point substantially obliquely relative to the longitudinal axis of the TES 1000 and penetrate into trabeculae along the implantation path in the bone tissue of the fractured vertebra. Barbs 1110, 1112, 1114 may be compressed to a very small profile. In some implementations, the motion to reconfigure the barbs 1110, 1112, 1114 from a non-deployed configuration (within the stent opening 1102 of TES 1000, for example, loaded within delivery cannula 1014) into a deployed configuration for anchoring the CFD-KI assembly to bone tissue may be a twisting motion which moves the barbs 1110, 1112, 1114 from being substantially aligned with the circumference of the TES 1000 to extend radially or obliquely outwards from the TES 1000. In any of the embodiments of the anchors described herein, the strength and flexibility provided by the twisting motion of the anchor is primarily affected by the width W of the neck portion of the twisted structure rather than its thickness T, which provides great advantage for design flexibility. Beam theory provides that the strength of a beam is primarily dictated by its thickness rather than its width. Accordingly, for a given wall thickness of stent tubing, by changing the width to which the anchors 1104 and the barbs 1110, 1112, 1114 are cut, the stiffness and flexibility of the anchors and barbs are easily changed.

Figure 17:
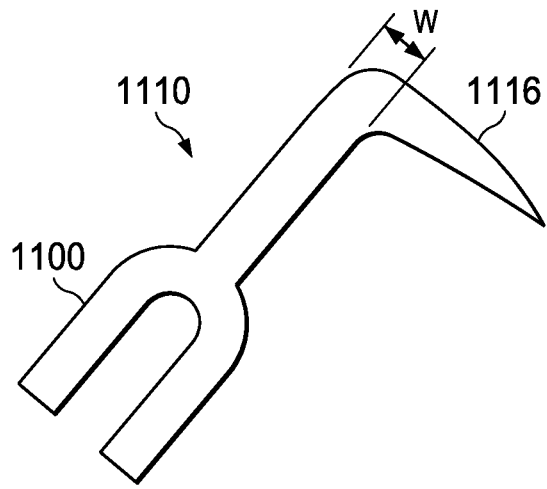
FIG. 17 is a perspective view of an exemplary expandable and retractable barb of a CFD, in an as-cut state.
Figure 18:
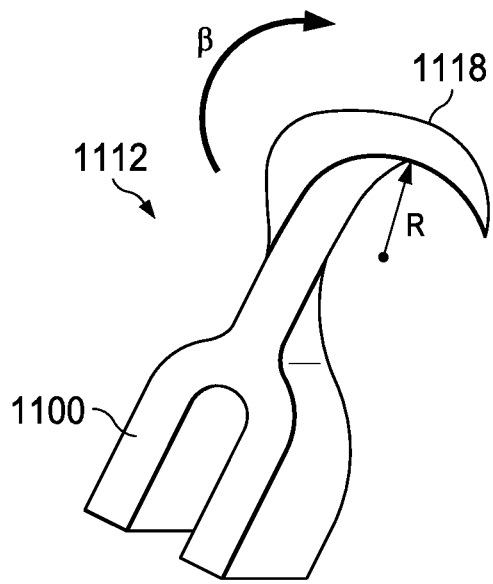
FIG. 18 is a perspective view of another exemplary expandable and retractable barb of a CFD in a set state.
Figure 19:
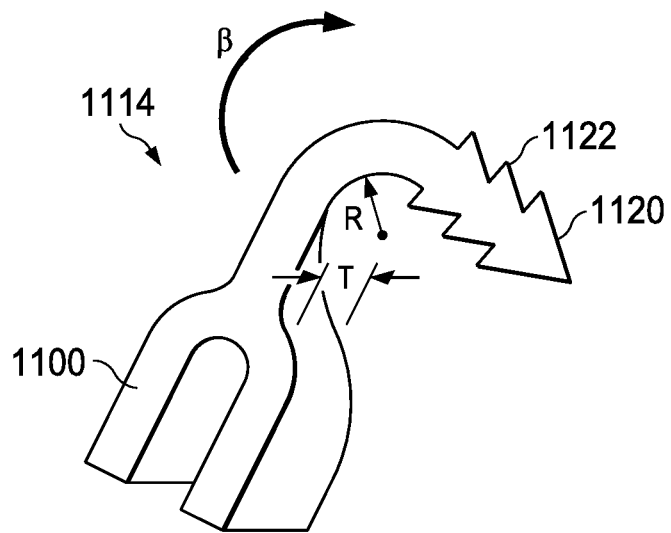
FIG. 19 is a perspective view of still another exemplary expandable and retractable barb of a CFD.
Figure 20A:
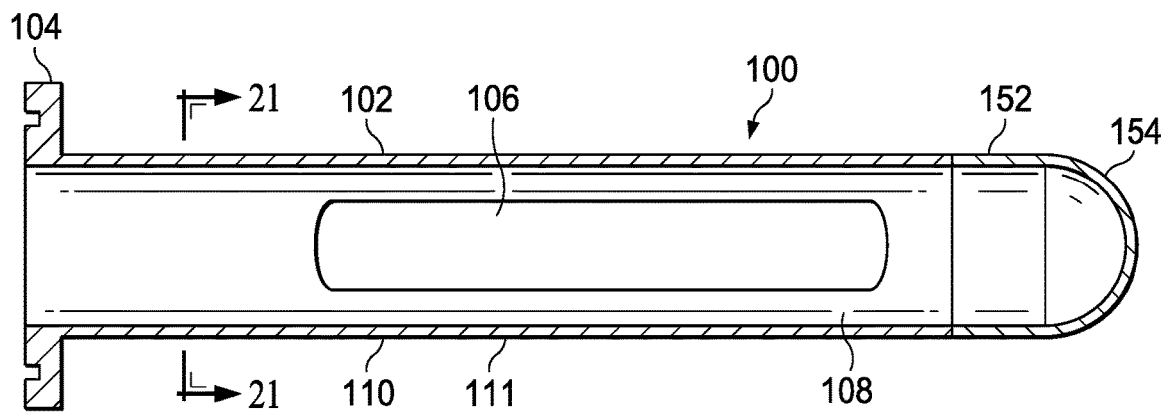
FIG. 20A is a top plan view of another implantable prosthesis.
Figure 20B:
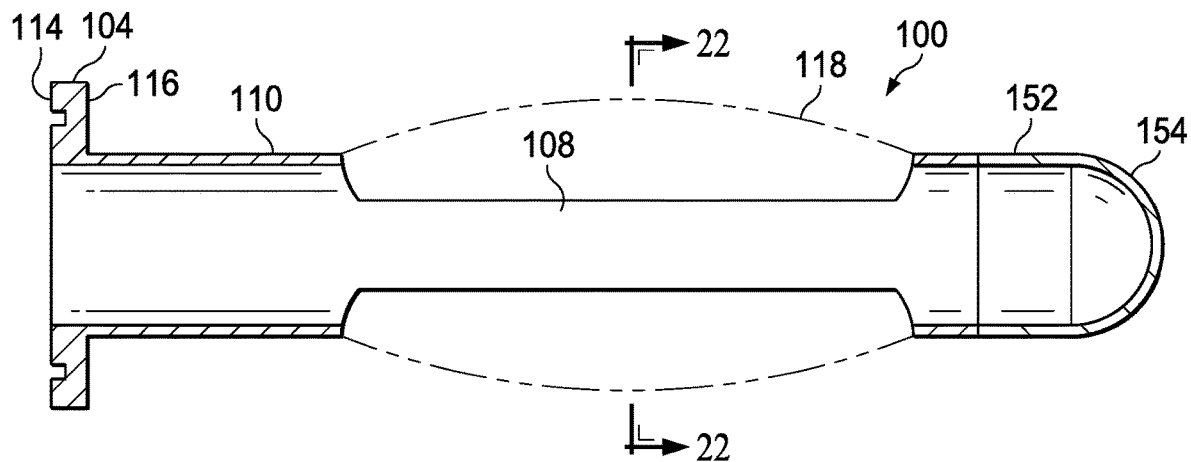
FIG. 20B is a side elevational view of the implantable prosthesis of FIG. 20A.

FIG. 17 shows a laser cut barb 1110 (in the as-cut state) made from a shape memory alloy tube (or flat sheet which can be bent into a tube) for creating the twisted barbs 1112 and 1114 (in a set state) shown in FIGS. 18 and 19, respectively, of TES 1000 for use in a CFD 1020 according to some embodiments of the invention. When the barb 1110 is in the as-cut state, the entire length of the anchor forms part of the wall 1100 of the TES 1000, whereas the when the barbs 1112, 1114 are in the set state or twisted state, a portion of the anchor protrudes from the outer surface of the TES 1000, as seen for example in FIG. 12. The barb angle β with respect to the wall 1100 can be modified to optimize the balance between anchoring force and flexibility of the barb. The radius R of the barb can also be modified to change the stiffness of the barb. Further, the width W of the barb can also be modified. By way of one example, and not by limitation, the barb angle β can be about 110 degrees, the radius R can be about 0.0200 inch, and the width W can be about 0.0100 inch. Of course, other angles, radii, widths, lengths, and thicknesses may be employed.

FIG. 19 illustrates one example wherein reverse barbs 1122 are formed on the tip of barb 1114, which may improve trabecular traction and fixation of the CFD 1020 to adjacent bone. Of course, a plurality of such barbs and anchors may be included and distributed around the circumference and length of TES 1000 as needed.

In some embodiments, a TES such as TES 1000 may be movable between a collapsed non-deployed configuration within the delivery instrument and an expanded deployed configuration along the access path, and when the TES is in the non-deployed configuration, the anchoring portion may be substantially within a slot portion within the circumference of the TES (see, e.g., FIG. 9).

As shown in FIGS. 20A, 20B, 21 and 22, an implant 100 useful for performing kyphoplasty may include an elongated tubular housing 102 and an inflatable member 118 disposed in housing 102. In some embodiments, inflatable member 118 may be constructed of a compliant material (e.g., an elastomeric material such as polyurethane or silicone), a semi-compliant material (e.g., PEBAX™ or higher durometer polyurethanes), or a noncompliant material (e.g., polyester or nylon), for example, or a combination thereof. Housing 102 may have a flange 104 at its proximal end and a rounded end cap 152 including a nose cone 154 at its distal end to help facilitate insertion of implant 100 into an access cannula 210 (see, e.g., FIGS. 23 and 47) and ultimately into a vertebral body 10 as described further below. Housing 102 may have one or more slots 106 to facilitate expansion of inflatable member 118 outside housing 102. In some embodiments, housing 102, end cap 152, and inflatable member 118 may be fabricated separately and assembled together in a three-piece construction as described in more detail below.

Figure 21:
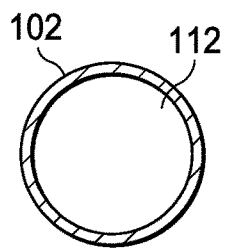
FIG. 21 is a cross-sectional view of section 21-21 as shown in FIG. 20A.
Figure 22:
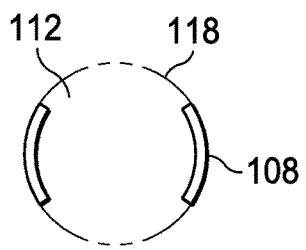
FIG. 22 is a cross-sectional view of section 22-22 as shown in FIG. 20A.

Housing 102 may include an elongated, generally cylindrical structure which has a cylindrical inner channel 112 traversing through housing 102, as shown in the cross-sectional views of FIGS. 21 and 22, for example. Housing 102, which may include a thin rigid cylindrical wall, may be fabricated from metal, polymer, other suitable materials, or a combination thereof. In some embodiments, housing 102 may have an outer diameter of approximately 4-8 mm and a length of approximately 20-40 mm, for example. Of course, any suitable sizing may be used for housing 102 and the other components described herein. Inner channel 112 may extend longitudinally from a proximal end of housing 102 to a distal end of housing 102. An intermediate portion 111 of housing 102 may have one or more slots 106 cut or otherwise formed therein. The one or more slots 106 may be bounded by one or more struts 108. Housing 102 may include an anchoring portion 110 that extends between flange 104 and intermediate portion 111. Anchoring portion 110 may serve to anchor implant 100 in a vertebral body 10, sometimes in conjunction with an external fastener 126 as shown in FIG. 23.

Figure 23:
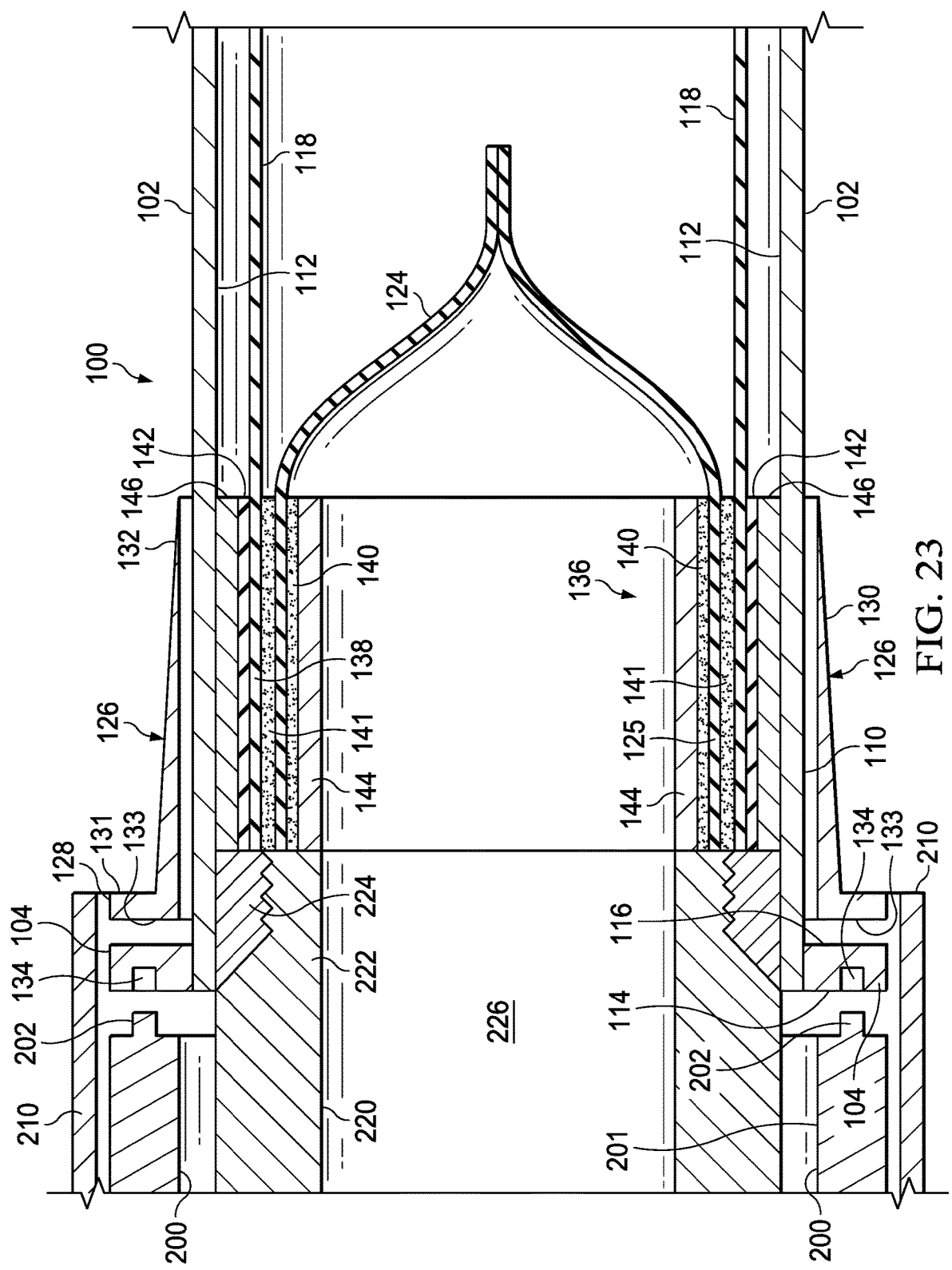
FIG. 23 is a longitudinal cross-sectional view of a proximal portion of the implantable prosthesis of FIG. 20A and a cortical fastener, an inflation cannula, an access cannula, and an anti-rotation device.

Referring to FIG. 23, in some embodiments, a tubular, conically shaped external fastener 126 may be disposed about anchoring portion 110 to aid in securely attaching implant 100 with respect to a vertebral body 10 as described further below. External fastener 126 may include a shaft 130 having a cylindrical bore and a conically tapered exterior surface, a collar 128 at a proximal end of shaft 130, and a sharp tip 132 (e.g., in the form of a circular edge due to the tubular nature of external fastener 126) at a distal end of shaft 130. Sharp tip 132 may help facilitate insertion of external fastener 126 into a vertebral body 10 as described further below in conjunction with FIGS. 45-47, and the conically tapered shape of shaft 130 may help facilitate secure attachment of external fastener 126 in a vertebral body 10. Although FIG. 23 shows a slight gap between external fastener 126 and housing 102 for the sake of clarity, the inner diameter of external fastener 126 may be substantially the same as the outer diameter of housing 102 to achieve a press fit (sometimes referred to as a friction fit) of housing 102 within external fastener 126 such that housing 102 may be fixed with respect to external fastener 126. Once installed, housing 102 may thus be substantially prevented from rotation or translation with respect to external fastener 126. Collar 128 of external fastener 126 may include a distal face 131 and a proximal face 133, and flange 104 of housing 102 may have a proximal face 114 and a distal face 116. Distal face 116 of flange 104 may be configured to abuttingly engage proximal face 133 of collar 128 when implant 100 is fully inserted into a vertebral body 10. Proximal face 114 of flange 104 may include an engagement seat 134 (e.g., in the form of a recess) sized and shaped for removable engagement with a protrusion 202 or other suitable engagement structure of an anti-rotation device 200 (sometimes referred to herein as an insertion tool), which may be used to insert external fastener 126 and implant 100 as described further below. The removable engagement of anti-rotation device 200 with implant 100 may serve to (1) hold the kyphoplasty implant 100 securely within the lumen of an access cannula 210 during insertion, (2) control rotation therebetween, and (3) hold implant 100 in place during counterclockwise rotation of inflation cannula 220 to disengage the inflation cannula 220 from implant 100 following completion of fluid injection. Alternatively, flange 104 may have a non-circular cross-sectional shape, such as a polygonal shape, and more particularly, a hexagonal shape, for example, to provide removable engagement with a complementarily shaped distal end of insertion tool 200. However, it should be understood that other shapes and configurations of the tool engaging portion are also contemplated as fully within the scope of some embodiments of the present invention.

In some embodiments, the shaft 201 of anti-rotation device 200 may be an integral tubular structure constructed of surgical steel, although any suitable material can be used, and may include a shaped engagement structure (such as protrusions 202) integrally formed at the distal end thereof. The engagement structure, which may have a hexagonal configuration, for example, may help facilitate mating and rotational engagement of the flange 104 of implant 100 with the anti-rotation device 200. It will be appreciated that the engagement structure of anti-rotation device 200 may take any angular configuration such as square, octagonal, or the like and can alternatively engage an outer periphery on the proximal face 114 of flange 104, for example.

The engagement structure (e.g., protrusions 202) of shaft 201 and the engagement seat 134 of flange 104 may be of complementary size and shape (e.g., male-female) so that the engagement structure (e.g., protrusions 202) can be snugly received within the engagement seat 134 of the flange 104 to rotationally lock the anti-rotation device 200 with the kyphoplasty implant 100. When the anti-rotation device 200 and the kyphoplasty implant 100 are so engaged, they may be inserted through the proximal opening of access cannula 210 and advanced together within the lumen of access cannula 210 to deposit implant 100 at the kyphoplasty site under fluoroscopic observation. Reverse rotation and/or pulling out of the anti-rotation device 200 will of course unlock the insertion tool 200 and flange 104.

Other configurations for rotationally and axially releasably interlocking the insertion tool 200 and the flange 104 of implant 100 are contemplated and are within the scope of some embodiments of the present invention. A single assembly, which may be referred to as a kyphoplasty implantation, reduction and fixation assembly, may allow a physician to expedite the procedure percutaneously with relative efficiency and increased safety.

In some embodiments, engagement mechanisms, as used herein, for releasably coupling an insertion tool 200 with an implant 100 may include annular snap-fits featuring a male component with a peripheral ridge or other protrusion and a corresponding female component having an undercut groove formed into the inside diameter of the female component. The male component deflects the female component and engages into the undercut groove, at which point the female component returns to a stress-free condition.

Still referring to FIG. 23, in some embodiments, inflatable member 118 may be securely attached to housing 102 near a proximal end thereof by a proximal mounting assembly 136. For example, a proximal waist 138 of inflatable member 118 and a skirt 125 of a one-way, self-sealing valve 124 may be sandwiched between an inner retaining ring 144 and an outer retaining ring 146 using an inner tie layer 140, an intermediate tie layer 141, and an outer tie layer 142. Inner tie layer 140, intermediate tie layer 141, and outer tie layer 142 may include or be composed of a polymeric bonding or adhesive material, for example, and outer retaining ring 146 may be press fit, bonded, or otherwise fixedly attached to an inner surface of housing 102. However, any suitable means of attachment may be employed to securely fasten inflatable member 118 to housing 102. At its proximal end, implant 100 may include a female fluid coupler 224 (e.g., a Luer connector or other suitable connector) configured for removable engagement with a male fluid coupler 222 of an inflation cannula 220 having an inflation lumen 226. Alternatively, implant 100 may include a male fluid coupler configured for removable engagement with a female fluid coupler of inflation cannula 220. At its proximal end (not shown), inflation cannula 220 may be directly or indirectly connected to a pressurized source of hardenable fluid material (not shown) that may be injected into implant 100 to facilitate pressurized expansion of inflatable member 118 as described further below. Although a threaded connection is shown between inflation cannula 220 and implant 100, any suitable connection may be used to sealingly and removably connect inflation cannula 220 to implant 100 to facilitate pressurized expansion of inflatable member 118 with a hardenable fluid material and removal of inflation cannula 220 after such expansion is completed.

The hardenable (curable) fluid material can assume various forms appropriate for delivering the material and may typically comprise a two-part delivery system. For example, commercially available systems for mixing and delivery of a two-part polymer material are available and may be utilized. Such systems further advantageously provide ethylene oxide sterilization capabilities and specialized extrusion devices that avoid air bubble entrapment in the mixture.

FIG. 23 illustrates a seal at a proximal mounting assembly 136, which in some embodiments may be accomplished as follows. An inner retaining ring 144 may be placed over a mandrel (not shown). A first layer of adhesive material and/or inner tie layer 140 may be applied over the inner retaining ring 144. The skirt 125 of valve 124 may then be applied, followed by intermediate tie layer 141 (e.g., adhesive material and/or polymeric insert), and the proximal waist 138 of the inflatable member 118. Another layer of adhesive material and/or polymeric insert (outer tie layer 142) may then be applied. An outer retaining ring 146 may be positioned over the outer tie layer 142 and crimped onto the proximal waist 138 of the inflatable member 118 and skirt 125 of the valve 124 by suitable mechanical means, such as a crimping fixture, for example. Finally, heat may be applied to the assembly 136, allowing the seal to conform to the underlying assembly and heat fusing the inflatable member 118 and valve 124 components to the retaining rings 144, 146. The bonded components may then be removed from the mandrel after it has cooled and may be inserted into the lumen 112 of housing 102.

The inner, intermediate, and outer tie layers 140, 141, 142 (e.g., polymeric inserts) and retaining rings 144, 146 may be made of biocompatible material, preferably polymeric in some embodiments, allowing for precise measurement and positioning of the layers. The polymeric inserts may be relatively more elastic and may be of lower durometer, providing matching of suitable durometer to the inflatable member 118 components.

In some embodiments, the outside diameter of proximal waist 138 may be configured to fit precisely in its designated position in housing 102. A groove or notch may be formed in an inner surface 112 of housing 102 to serve as a retaining means for proximal mounting assembly 136 as needed. As is apparent, there are numerous modifications of the embodiments described above that will be readily apparent to one skilled in the art to which this manufacturing process relates.

In some embodiments, a selected group of polymeric materials may be used to form the tie layers 140, 141, 142 and retaining rings 144, 146. Materials suitable to aid bonding between the layers may possess affinity to both materials forming the inflatable member 118 and retaining ring on one side, and the inflatable member 118 and the housing 102 on the other. Especially suited are materials such as PLEXAR™ available from LyondellBasell, Houston, Tex., or other such materials known in the art. With the use of such thermal bonding techniques and materials, especially utilizing suitable tie rings or layers, in some embodiments adhesives may not be required to form a desirable or secure bond among the components of proximal mounting assembly 136. As used herein, the term "polymer" will be understood to include polymers, copolymers (e.g., polymers formed using two or more different monomers), oligomers, and combinations thereof, as well as polymers, oligomers, or copolymers that can be formed in a miscible blend by, for example, coextrusion or reaction, including transesterification.

Figure 24:
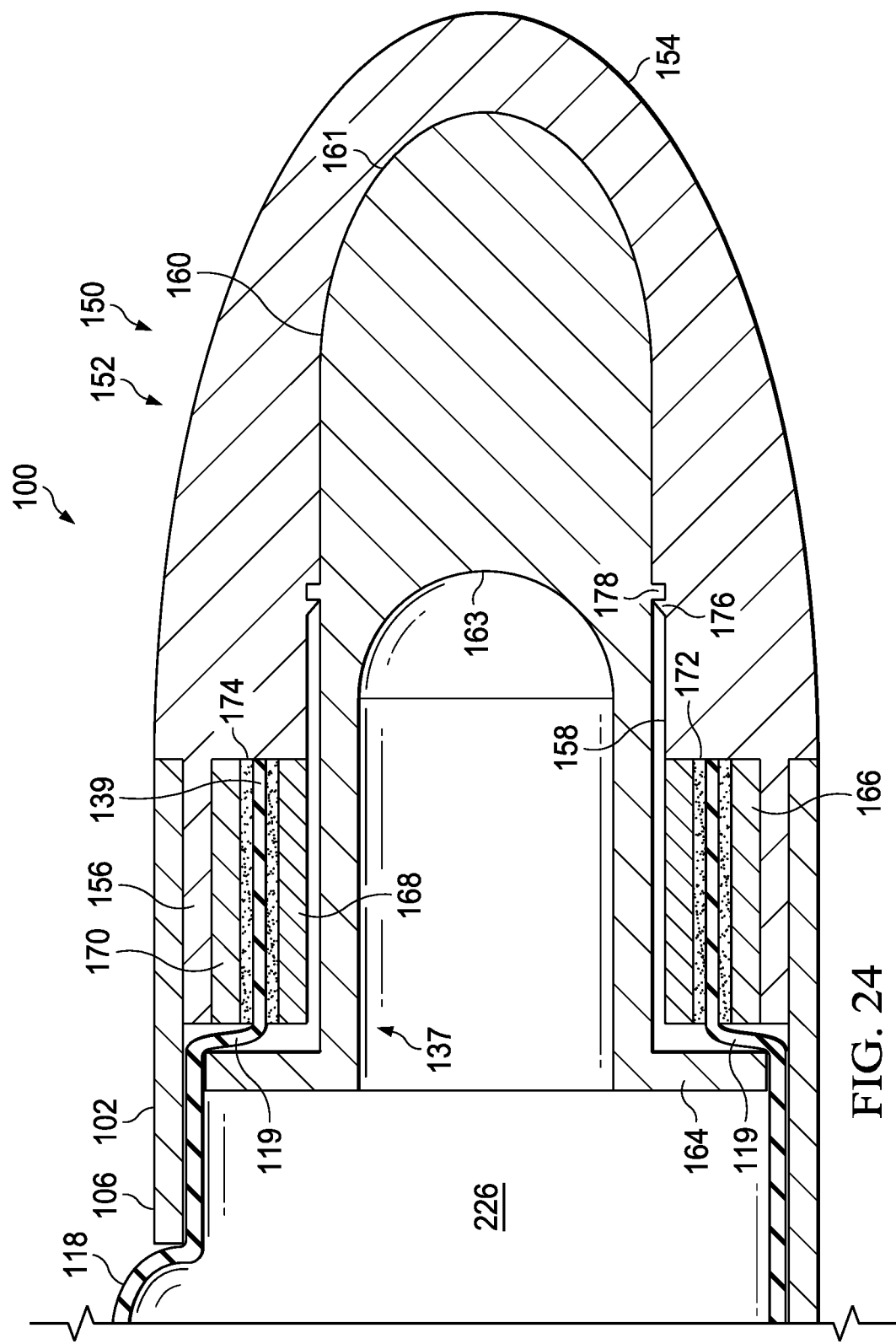
FIG. 24 is a longitudinal cross-sectional view of a distal portion of the implantable prosthesis of FIG. 20A.
Figure 25:
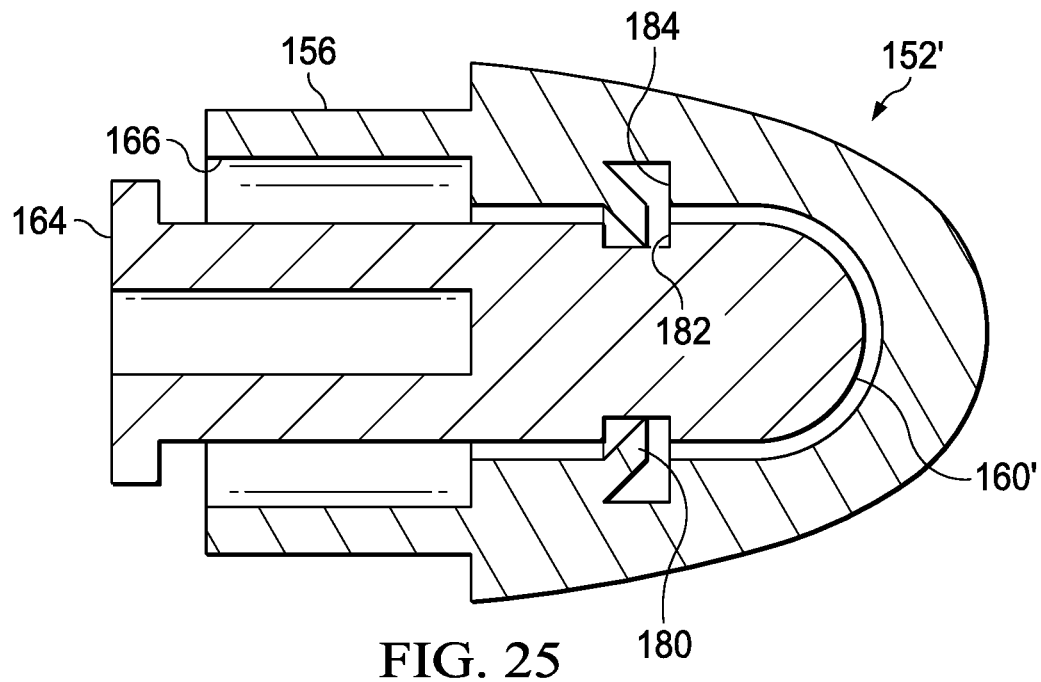
FIG. 25 is a longitudinal cross-sectional view of an alternative embodiment of a distal portion of an implantable prosthesis.
Figure 26:
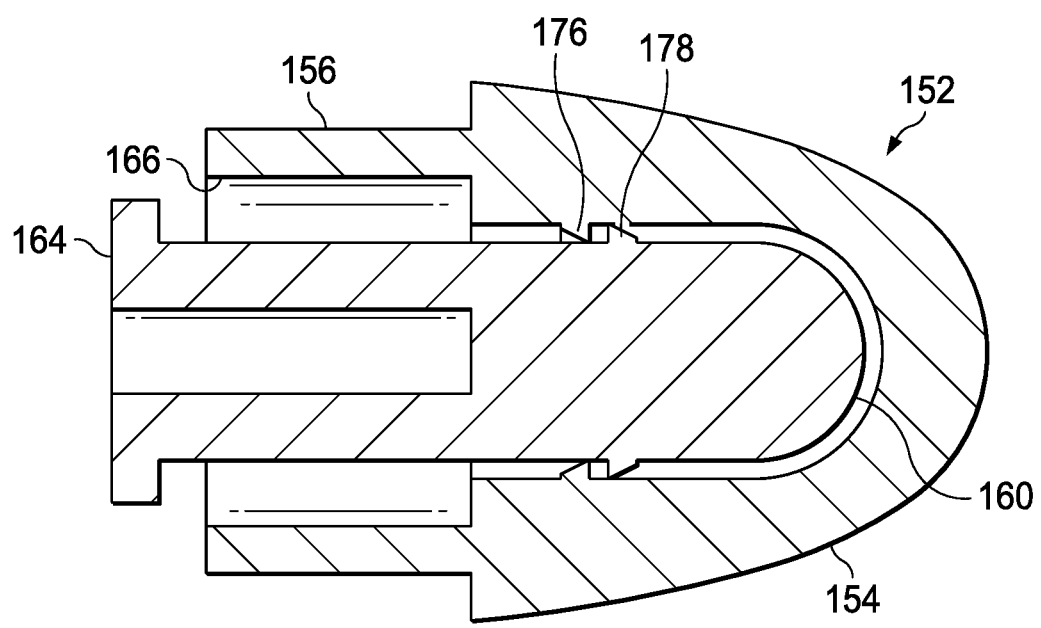
FIG. 26 is a longitudinal cross-sectional view of another alternative embodiment of a distal portion of an implantable prosthesis.

Referring to FIG. 24, in some embodiments, inflatable member 118 may be securely attached to housing 102 near a distal end thereof by a distal mounting assembly 137. For example, a distal waist 139 of inflatable member 118 may be sandwiched between an inner retaining ring 168 and an outer retaining ring 170 using an inner tie layer 172 and an outer tie layer 174. Inner tie layer 172 and outer tie layer 174 may include or be composed of a polymeric bonding or adhesive material, for example, and outer retaining ring 170 may be press fit, bonded, or otherwise fixedly attached to an inner surface of a collar 156 of end cap 152. In some embodiments, an internal fastener 160 may be used to help secure a distal end of inflatable member 118 to housing 102. For example, internal fastener 160 may include a flange 164 at its proximal end that is configured to capture a portion of inflatable member 118 between flange 164 and the proximal ends of collar 156 and outer retaining ring 170. As also shown in FIG. 26, internal fastener 160 may also include a protrusion 178 (e.g., an annular protrusion) configured for engagement with a catch 176 (e.g., another annular protrusion) that protrudes inward from an internal bore 158 of end cap 152. A distal edge of protrusion 178 and/or a proximal edge of catch 176 may be chamfered to help facilitate sliding of protrusion 178 over catch 176 as internal fastener 160 is pressed into end cap 152. Internal fastener 160 may be sized and configured with respect to end cap 152 such that when internal fastener 160 is fully inserted into end cap 152, flange 164 firmly holds inflatable member 118 against the proximal ends of collar 156 and outer retaining ring 170, and a distal edge of catch 176 bears against a proximal edge of protrusion 178 to prevent internal fastener 160 from being removed from end cap 152. Alternatively, in some embodiments, end cap 152 may include internal threads configured for engaging external threads of internal fastener 160. Another alternative configuration of an end cap and internal fastener is shown in FIG. 25. For example, an end cap 152' may include a catch 180 configured for engaging a recess 182 of an internal fastener 160'. Catch 180 may extend in a slanted direction away from a recess 184, which may allow catch 180 to flex as internal fastener 160' is inserted into end cap 152' until catch 180 springs into recess 182. A distal edge of recess 182 may then engage with a distal edge of catch 180 to prevent internal fastener 160' from being removed from end cap 152'. Of course, any suitable means of attachment may be employed to securely fasten inflatable member 118 to housing 102 at or near their distal ends. For example, other types of fasteners may include, but are not limited to, bayonet style fasteners, lock-and-key mechanism style fasteners, polymeric strain relief snap-fit, and the like.

FIG. 24 illustrates a seal at the distal mounting assembly 137, which in some embodiments may be accomplished as follows. Inner retaining ring 168 may be placed over a mandrel (not shown). A first layer of adhesive material and/or inner polymeric insert (inner tie layer 172) may be applied over the inner retaining ring 168. The distal waist 139 of the inflatable member 118 may then be stretched and applied over the tie layer 172. A second layer of adhesive material and/or outer polymeric insert (outer tie layer 174) may be applied over the distal end of the inflatable member 118. The outer retaining ring 170 may be applied and crimped onto the distal end of the inflatable member 118 by suitable mechanical means, such as a crimping fixture, for example, and excess material of inflatable member 118 may be trimmed distal to the outer retaining ring 170. The assembly 137 may be heat fused and, when cooled, inserted into the bore 166 of end cap collar 156.

In some embodiments, the distal mounting assembly 137 described above may be inserted snugly into end cap bore 166 and covered with end cap collar 156, which may be formed of a polymeric material, which when heated may act as a shrink tube to conform to the underlying assembly 137 and heat fusing the assembly 137 including the distal portion of the inflatable member 118 (and optionally including any support structure, if present, of the inflatable member, such as jacket 258, support 706, or supporting structure 726 described below) to end cap 152.

In some embodiments of the distal mounting assembly 137, an internal fastener such as fastener 160 may be inserted into the bore 158 of end cap 152 and permanently engaged therein. Flange 164 of internal fastener 160 may entrap segment 119 of inflatable member 118 against the inner wall 112 of housing 102 and a proximal face portion of mounting assembly 137 creating an interference fit therebetween that securely fastens and seals the distal region of inflatable member 118 to housing 102.

End cap 152 and internal fastener 160 distal tip members of some embodiments of the present invention may be made of any material known to those of skill in the art to be compatible with orthopedic usage. For example, in some embodiments, the distal tip members may be made of metals such as titanium, titanium alloys, stainless steel, stainless steel alloys, chrome cobalt, or graphite ceramics, or a combination thereof. Non-metals may also be used, such as biocompatible polymers, carbon reinforced composites, and the like.

Figure 27:
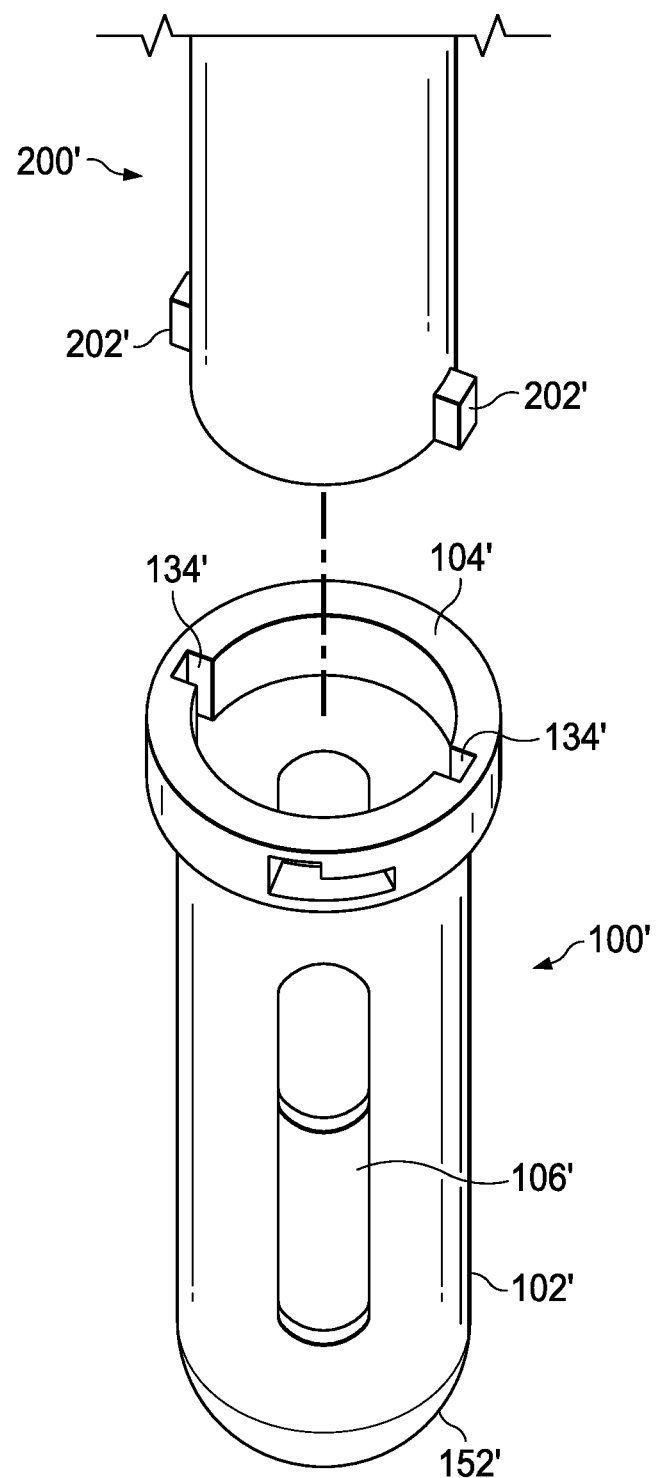
FIG. 27 is an exploded perspective view of the implantable prosthesis of FIG. 20A and an anti-rotation device.

As shown in FIG. 27, an alternative embodiment of an implant 100' may include a proximal flange 104' having engagement seats 134' configured for removably receiving respective protrusions 202' of an insertion tool 200'. Similar to implant 100, implant 100' may include an end cap 152' and a housing 102' having one or more slots 106' through which an inflatable member may be expanded. Insertion tool 200' may be used to insert implant 100' into a vertebral body 10 through a cannula as described herein, and after implant 100' is installed, insertion tool 200' may be removed.

Figure 28:
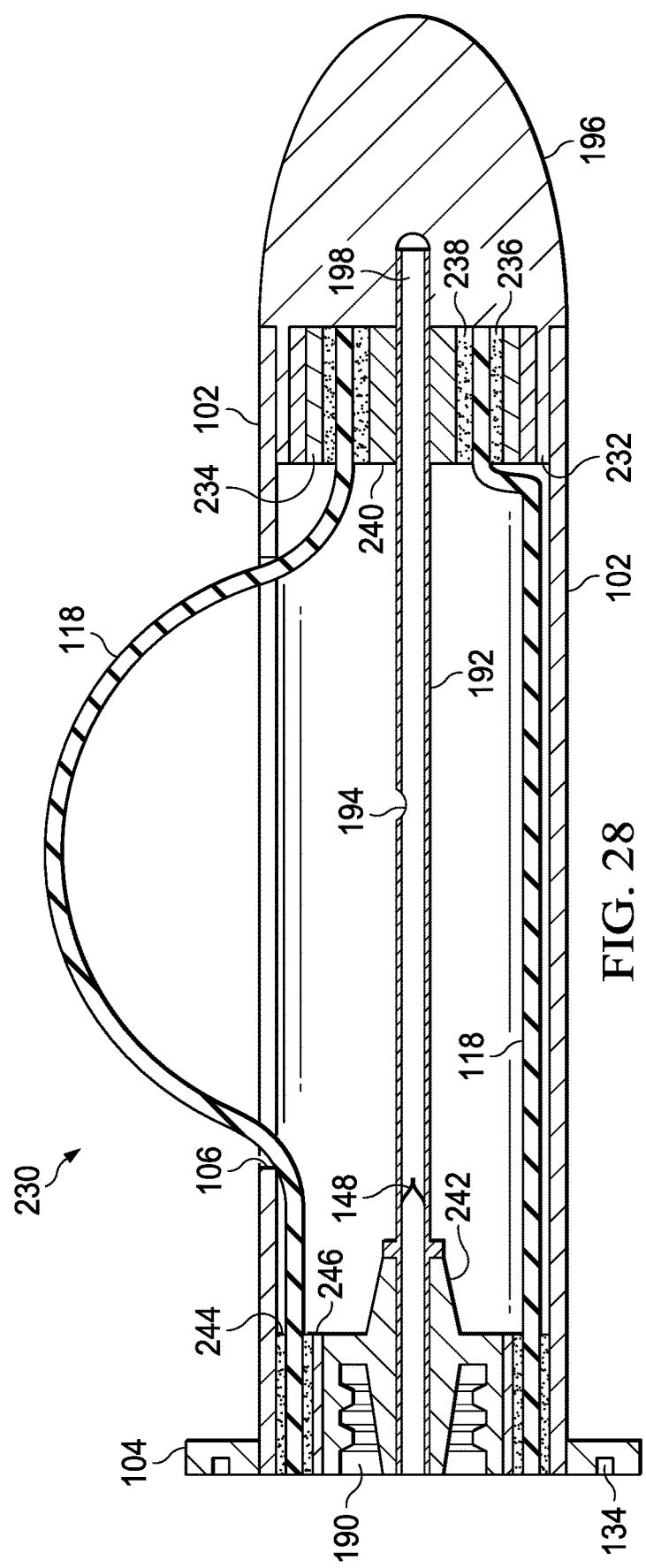
FIG. 28 is a longitudinal cross-sectional view of another embodiment of an implantable prosthesis.

Referring to FIG. 28, another alternative embodiment of an implant 230 is shown. Implant 230 may include a generally hollow tubular housing 102, an end cap 196 at a distal end of housing 102, and a flange 104 at a proximal end of housing 102. Implant 230 may also include an inflatable member 118 that is initially disposed within housing 102 but is inflatable to expand outside of housing 102 via a slot 106 in housing 102. The edges of slot 106 may be smooth to prevent rupture or puncture of inflatable member 118 as it expands through slot 106. Similar to implant 100 described above, a distal end of inflatable member 118 may be secured in place adjacent end cap 196 by being annularly sandwiched between a skirt 232 of end cap 196 and an internal cannula 192 using an inner retaining ring 240, an outer retaining ring 234, an inner tie layer 238, and an outer tie layer 236. Inner tie layer 238 and outer tie layer 236 may include or be composed of a polymeric bonding or adhesive material, for example, and outer retaining ring 234 may be press fit, bonded, or otherwise fixedly attached to an inner surface of skirt 232 of end cap 196. Likewise, skirt 232 may be press fit, bonded, or otherwise fixedly attached to an inner surface of housing 102. Internal cannula 192 may have a distal end disposed in a recess 198 of end cap 196 for stability. Inner retaining ring 240 may have an internal diameter that is substantially the same as the outer diameter of internal cannula 192 to help support internal cannula 192. Internal cannula 192 may be supported at a proximal end of housing 102 by a proximal end fitting 242. Proximal end fitting 242 may include a female Luer connector 190 configured for removable and sealing connection to a male Luer connector (not shown), which in turn may be directly or indirectly connected to a pressurized source of hardenable fluid material (not shown) that may be injected into internal cannula 192 to facilitate pressurized expansion of inflatable member 118 with the hardenable fluid material through an orifice 194 of internal cannula 192. Proximal end fitting 242 and a proximal end of inflatable member 118 may be secured to housing 102 by any suitable means. For example, a proximal end of inflatable member 118 may be annularly sandwiched between housing 102 and proximal end fitting 242 using an inner tie layer 246 and an outer tie layer 244. Inner tie layer 246 and outer tie layer 244 may include or be composed of a polymeric bonding or adhesive material, for example, to fasten proximal end fitting 242 and the proximal end of inflatable member 118 in place at the proximal end of housing 102 as shown. Of course, other fastening means may be used. Proximal end fitting 242 may include a one-way, self-sealing valve 148 to allow hardenable fluid material to be injected into internal cannula 192 and prevent hardenable fluid material from leaking back out of internal cannula 192. Housing 102 may include a flange 104 at its proximal end as described above for implant 100.

Still referring to FIG. 28, a kyphoplasty implant 230 of some embodiments of this invention may include three main parts: a housing 102, an internal cannula 192, and an inflatable member 118. For ease of manufacturing, the housing 102 may be formed from three pieces, with the proximal piece surrounded by a flange 104, the middle piece provided with at least one longitudinal slot 106, and the distal piece having a blunt end cap 196. In some embodiments, the internal cannula 192 may be formed separately from the housing 102 and bonded in a central aspect of the housing 102. The inflatable member 118 can be a medical balloon located about the internal cannula 192 in the annular space between the cannula 192 and the housing wall 112 and may evaginate through the housing slot 106 upon inflation via the internal cannula 192. A movable diaphragm and/or duckbill valve 148 may be incorporated in the proximal opening of the housing 102 or internal cannula 192.

When the kyphoplasty implant is assembled, the housing 102 may include a proximal end and a distal end. The proximal end of the housing 102 may include a flange 104 with a proximal opening in the form of a female connector 190 (such as a Luer connector, for example). The distal end of the housing may include an end cap 196 having a blunt nose cone.

The internal cannula 192 may be hollow to define a fluid flow path therethrough and may include a proximal end and a distal end. The proximal end of the cannula 192 may be disposed adjacent the female connector 190 of the housing 102, and the distal end of the cannula 192 may be closed and attached in a central aspect of the end cap 196. An opening 194 in a middle portion of the internal cannula 192 may provide fluid communication between the proximal inlet and the lumen of the inflatable member 118. With this arrangement, hardenable fluid may flow through the one-way valve 148 into the internal cannula 192 and through the opening 194 and expand the inflatable member 118, which may evaginate through the slot 106 in a direction generally perpendicular to the longitudinal axis of the housing 102. A duckbill valve 148 may fit snugly in a proximal aspect of the cannula 192 in the proximity of the female connector 190. An inflation cannula 220 with a male connector at its tip may engage the female connector 190 in a leak proof fashion. An insertion tool 200 that engages a proximal end of the housing 102, such as the housing flange 104, may allow easy and safe remote disconnection of the inflation cannula 220 and insertion tool 200 at the end of the percutaneous procedure.

The end cap 196 may be made from PEBAX™ or other suitable material, and its outer diameter may range from about 3-7 mm, for example, preferably about 5 mm in some embodiments. Its length may be in the range of about 5-8 mm in some embodiments. Of course, any suitable sizing may be used. An outer margin of the nose cone of end cap 196 may form a smooth transition with an outer margin of the housing 102 and may have a smooth frictionless outer surface and an elongated, conical, or tapered shape adapted to facilitate maneuverability of the implant 230 along the access path.

Referring again to FIG. 28, in some embodiments, inner tie layer 238 and outer tie layer 236 may be or may include polymeric inserts to aid in bond formation between the distal portion of the inflatable member 118, the outer surface of the inner retaining ring 240, and the inner surface of the skirt 232 of the end cap 196. The polymeric inserts may be formed of the same or different polymeric materials of suitable durometer and bonding characteristics. In some embodiments, the primary considerations in the choice of suitable polymeric materials to function in this manner are that the components subjected to bonding are compatible with each other and that they have suitable durometer in order to maintain a strong mechanical, non-deformable bond, especially with the inflatable member 118. The inner and outer polymeric inserts may serve as tie layers to facilitate bonding of the various materials which may ordinarily be considered to be incompatible for thermal bonding. These inserts or tie layers may also be used in facilitating bonding of other parts of the implant device where two incompatible materials are being used. For example, such techniques are commonly used in medical balloon catheter tip designs. In some examples, a polymeric insert or tie layer may include a polyester polymer and a polyamide polymer. Unlike traditional bonding procedures, such as use of adhesives, a polymeric insert or tie layer may permit manufacturers to form a secured bond between different layers such as balloons and catheters using thermal bonding processing alone. Adhesives, although they may still be used, may not be required to form a secure bond in some embodiments.

Medical balloons suitable for inflatable member 118 may be of semi-compliant or non-compliant variety. Conventional balloons utilized for kyphoplasty procedures may be suitable, as long as the material used is bio-compatible for long-term implantation. Semi-compliant balloons may offer some advantages over non-compliant balloons in some embodiments of this invention for several reasons. For example, semi-compliant balloons tend to be less stiff than non-compliant balloons, resulting in easier foldability and sizing. Semi-compliant balloons may also provide better puncture resistance. Semi-compliant balloons may be produced from materials such as nylon which is softer than polyethylene terephthalate (PET) and provides moderate compliance and flexibility. In some embodiments, semi-compliant balloons may have a desirable combination of distensibility, elastic stress response, and strength.

The balloons may be constructed in any of a variety of ways, including techniques utilized for balloon kyphoplasty applications, for example. Alternatively, balloon-like structures may be made of fabrics, ePTFE, or composite materials, for example. In some embodiments, multi-layered or fiber reinforced balloons may be used to minimize the risk of rupture, and/or provide surface features that improve integration with the surrounding cancellous bone.

In some embodiments, the hardenable fluid material may be or may include a room temperature vulcanizing polymer such as silicone, polyurethane, polyester, or blends of polyurethane-silicone, or a combination thereof. In some embodiments, such materials may be preferable to polymethyl methacrylate (PMMA), which may be used in some embodiments, as their durometer can be adjusted to be close to the durometer of the adjacent bone. In vertebrae that are severely osteoporotic, it is generally desirable that the hardenable material utilized exhibits a low modulus of elasticity, which may range between about 10-150 GPa, for example. In some embodiments, the polymerization may be only minimally exothermic to prevent thermal damage to the surrounding tissues.

Figure 29A:
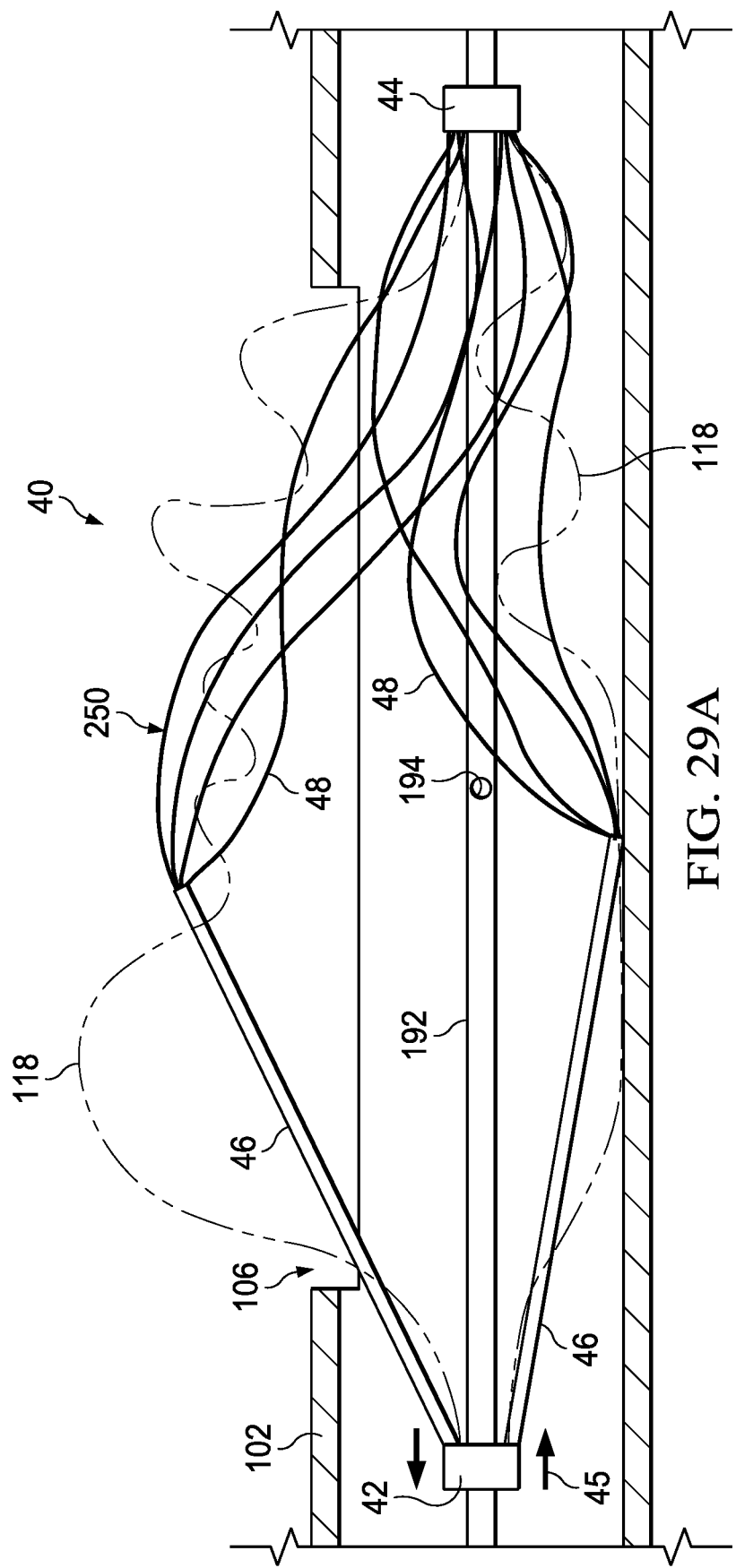
FIG. 29A is a longitudinal cross-sectional view of an intermediate portion of an implantable prosthesis including an inflatable member and an expandable jacket.

As illustrated in FIG. 29A, in some embodiments, a kyphoplasty inflatable implant 40 may include a housing 102, an inflatable member 118, and an expandable jacket 250 disposed about inflatable member 118. Expandable jacket 250 may include one or more legs 46 and one or more filaments 48 configured to direct the expansion of inflatable member 118. Inflatable member 118 may be attached about an internal cannula (inflation tube) 192 having an orifice 194 through which a hardenable fluid may be injected to expand inflatable member 118 once implant 40 is suitably positioned within a vertebra as described herein. Inflatable member 118 and expandable jacket 250 initially may be disposed within housing 102 but are expandable to extend outside of housing 102 via a slot 106 in housing 102 as inflatable member 118 is inflated with hardenable fluid. In some implementations, the edges of slot 106 may be rounded, beveled, or otherwise smooth to prevent entanglement of jacket 250 within slot 106 and to prevent inadvertent rupture of inflatable member 118 as the assembly expands through slot 106. Similar to implants 100 and 230 described above, in some embodiments, the distal ends of expandable jacket 250 and inflatable member 118 may be secured in place adjacent end cap 196, such as with a fixed ring 44 attached to internal cannula 192, for example. A proximal end of expandable jacket 250 (e.g., the proximal ends of legs 46) and inflatable member 118 may be attached to a sliding ring 42 that is movable longitudinally along internal cannula 192 within housing 102. Sliding ring 42 may include an opening that admits inflation tube 192 therethrough, and ring 42 may be slidable proximally and distally along inflation tube 192 as indicated by arrows 45. When the expandable assembly of inflatable member 118 and expandable jacket 250 is within housing 102, the assembly assumes a collapsed, reduced diameter profile. When inflatable member 118 is pressurized and expanded with fluid, the array of filaments 48 and legs 46 diverge outward from inflation tube 192, and filaments 48 (via legs 46) pull the sliding ring 42 distally along inflation tube 192. As the ring 42 is moved distally along the inflation tube 192, the expandable assembly shifts between a collapsed state and an expanded state. Filaments 48 and legs 46 may be made of stainless steel, Nitinol, polymer composites, other suitable materials, or a combination thereof.

Although expandable jacket 250 and inflatable member 118 are shown as being initially disposed within a housing 102 in FIG. 29A, some embodiments may not include a housing. Instead, in some embodiments, implant 40 without a housing may be delivered to a desired location within a vertebra through a delivery cannula, the delivery cannula may be retracted from the implant 40, and implant 40 may be expanded within the vertebra by inflating inflatable member 118 with hardenable fluid as described herein.

Figure 29B:
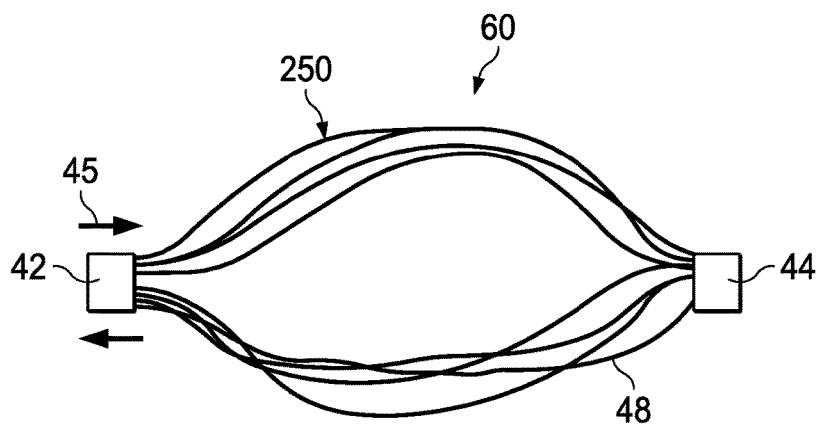
FIG. 29B is a longitudinal cross-sectional view of another embodiment of an expandable jacket of an implantable prosthesis in the form of a wire basket formed of helical wires attached proximally to a slidable ring and distally to a fixed element in the end cap.

Referring to FIG. 29B, in some embodiments, an inflatable implant 60 may or may not include a housing. As shown, implant 60 may include an expandable jacket 250 made of an array of helical filaments 48 (e.g., wires, cables, strings, or the like) disposed about an inflatable member (not shown), which may be expanded with a hardenable fluid as described herein. Similar to implant 40, implant 60 may have a sliding ring 42 at one end and a fixed ring 44 at the other end. Sliding ring 42 may be slidable along an inflation tube (not shown) as described above for implant 40 as indicated by arrows 45, and fixed ring 44 may be fixedly attached to the inflation tube. Unlike implant 40, the expandable jacket 250 of implant 60 may not have any legs 46.

Figure 29C:
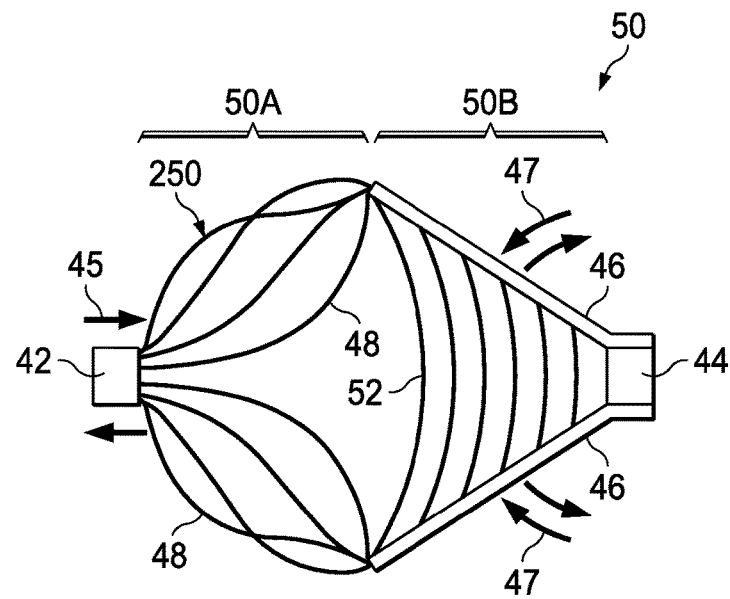
FIG. 29C is a longitudinal cross-sectional view of another embodiment of an expandable jacket of an implantable prosthesis including a distal ribbon portion formed of a first material and a proximal portion formed of a second material.

Referring to FIG. 29C, in some embodiments, an inflatable implant 50 may have an expandable jacket 250 including a first portion 50A and a second portion 50B. The expandable jacket 250 may be disposed about an inflatable member (not shown) similar to other embodiments described herein. The first portion 50A may be made with a plurality of filaments 48 made of a first material, and the second portion 50B may be made with a plurality of filaments 52 of a second material. The first and second materials may have different stiffnesses, which may be configured to produce differential expansion of the inflatable member in specific directions within a vertebra as needed to correct specific deformities. Expandable jacket 250 may include two or more diverging legs 46 that at one end, for example, are bonded or otherwise attached to an end cap (e.g., end cap 196 as shown in FIG. 28), such as at a fixed ring 44 which is attached to or part of the end cap, for example, and are articulated at the other end whereby a plurality of thin and flexible filaments 48 are in turn articulated to a slidable insertion ring 42. Filaments 48 and 52 may be attached to legs 46 as shown. Legs 46 may be flexibly attached to ring 44 to permit pivotal movement of legs 46 as shown by arrows 47, and ring 44 may be fixedly attached to the inflation tube (not shown) as described for implant 40. Filaments 48 may be attached to sliding ring 42, which may be slidably installed on the inflation tube as indicated by arrows 45 to facilitate expansion of the inflatable member and expandable jacket 250 as described for implant 40. In some embodiments, the first portion 50A may be proximal and the second portion 50B may be distal, and in some embodiments, the first portion 50A may be distal and the second portion 50B may be proximal. Each of the sliding ring 42 and the fixed ring 44 may be either proximal or distal, depending on the particular application and the desired differential expansion characteristics. As illustrated, in some embodiments, the gap between diverging legs 46 may be bridged by a transversely oriented plurality of filaments 52 or by a net formed of fabric or thin wires, for example. Such a net member may limit balloon protrusion through expandable jacket 250. This particular feature may have utility in some kyphoplasty implants intended for use in an anteriorly wedge-shaped vertebral body fracture, for example (see FIGS. 52 and 53), where differential expansion of the anterior aspect of a vertebral body is desirable, with relatively less expansion of the posterior aspect of the vertebral body.

In some embodiments, the inflatable member 118 and the expandable jacket 250 may be separate and movable with respect to each other (e.g., in areas other than where they are both attached to other structure, such as rings 42 and 44, for example) to achieve a collapsed position of the expandable assembly in which the assembly is within the lumen of a housing or a delivery cannula and another position of the expandable assembly in which at least a portion of the assembly extends away from its initial collapsed position. In the expanded position, the expandable assembly assumes a generally controllable 3-dimensional shape as it interdigitates with the vertebral trabeculae and differentially and directionally expands the fractured vertebral body and restores vertebral alignment.

In some embodiments, the expandable assembly may take the form of a basket similar to conventional retrieval baskets, such as shown in FIGS. 29A-29E, for example. The basket may have a plurality of legs 46; for example, the basket may have 2, 3, 4, 5 or more legs 46. In some embodiments, the legs 46 may be preformed into a spiral or other curved configuration, for example.

In some embodiments, the legs 46 of the expandable assembly may feature a proximal portion and a distal portion. The proximal portion of the legs 46 may include a first material and the distal portion of the legs 46 may include a second material, the second material being more flexible than the first material. Alternatively or additionally, different flexibility of the proximal and distal portions of the legs 46 may be achieved via different thicknesses, cross-sectional shapes, or a combination thereof. The legs 46 may be straight or curved or a combination thereof. In some embodiments, the legs 46 may have a greater stiffness than filaments 48 such that inflatable member 118 may be allowed to expand to a greater extent in the vicinity of filaments 48 than in the vicinity of legs 46.

Figure 29D:
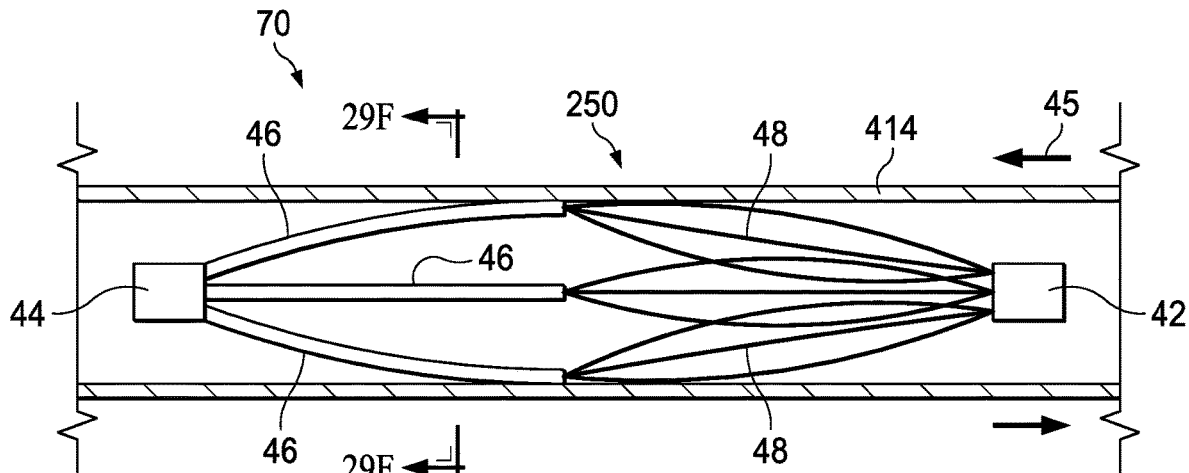
FIG. 29D is a longitudinal cross-sectional view of another embodiment of an expandable jacket of an implantable prosthesis collapsed within the lumen of a delivery cannula.
Figure 29E:
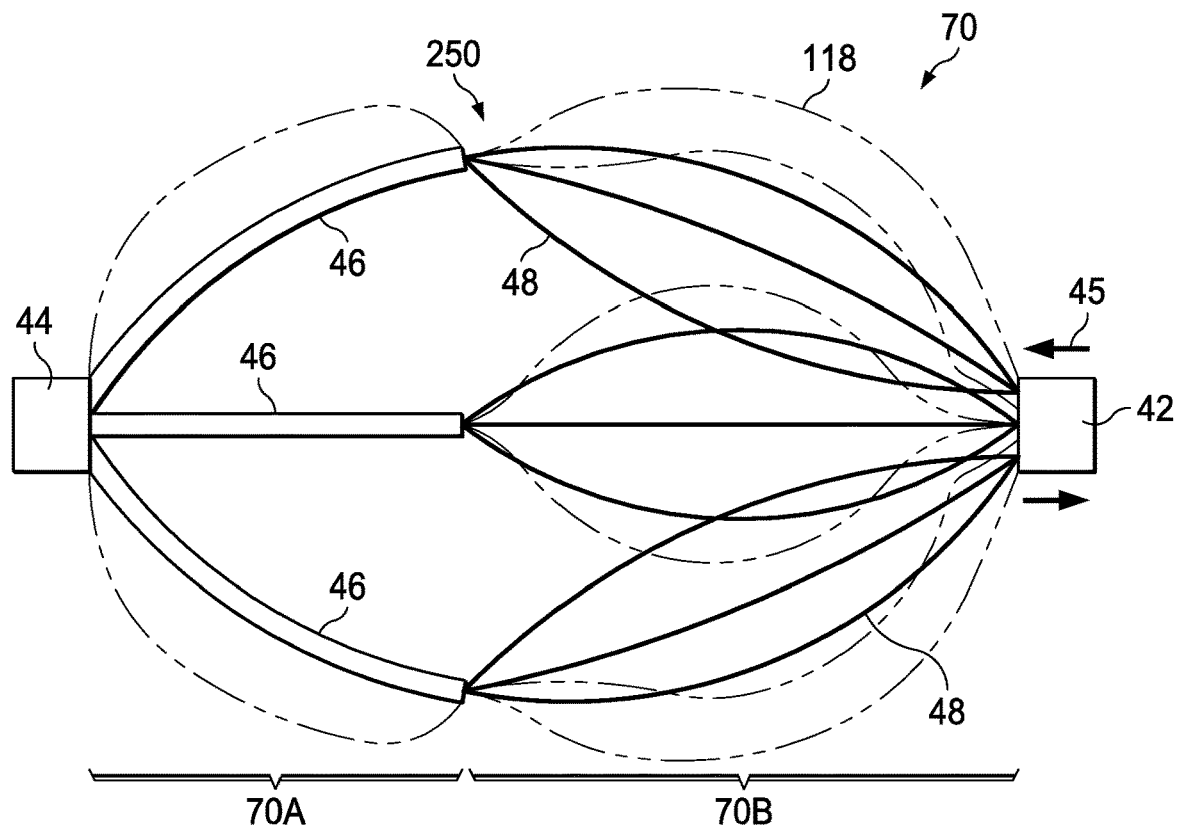
FIG. 29E is a longitudinal cross-sectional view of the expandable jacket shown in FIG. 29D following expansion by an inflatable member shown in dashed lines.
Figure 29F:
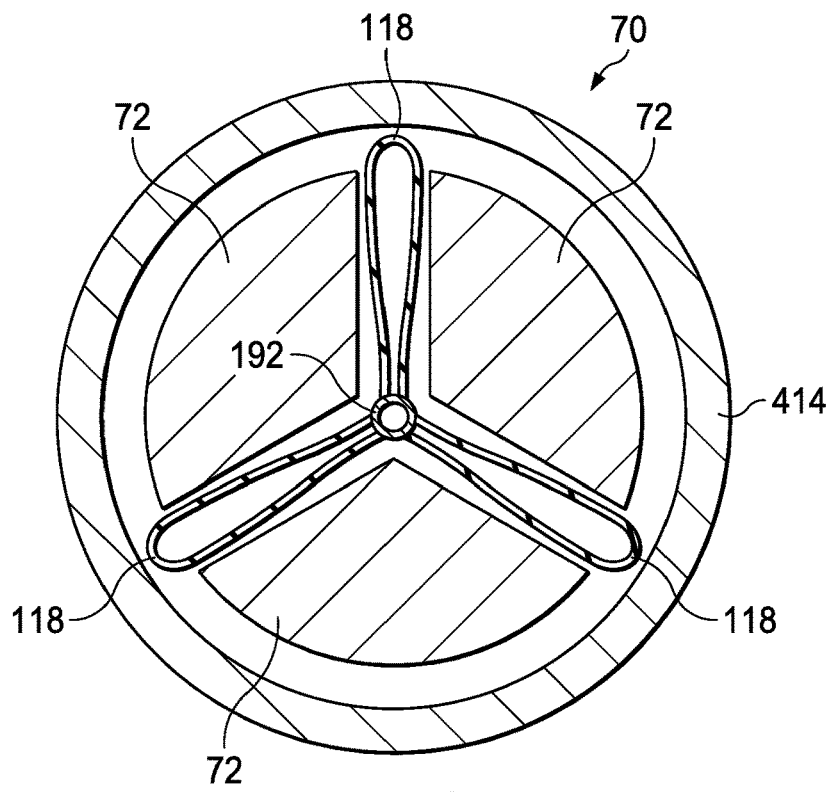
FIG. 29F is a cross-sectional view taken along the line 29F-29F of FIG. 29D in which wedge-shaped legs are depicted enclosing a trefoil-shaped inflatable member therebetween.
Figure 29G:
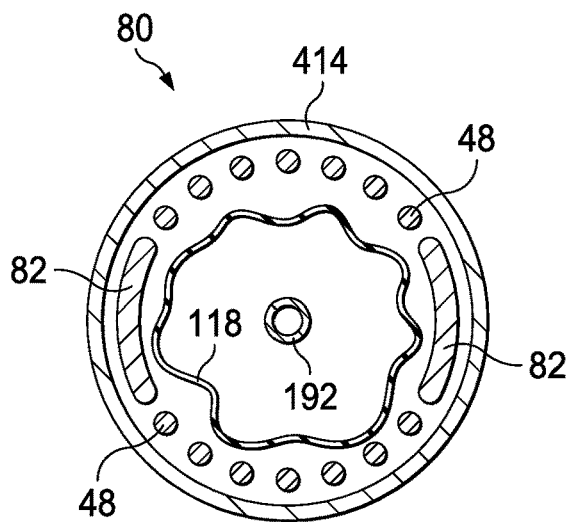
FIG. 29G is an axial cross-sectional view of an inflatable implant including an inflatable balloon-expandable jacket assembly having a pair of spiral type ribbons with cross-sectional curvature spaced laterally within the lumen of a delivery cannula together with a plurality of round cross-section wires arranged cephalad and caudad around the inner circumference of the delivery cannula, and an inner inflatable member and a central inflation tube.
Figure 29H:
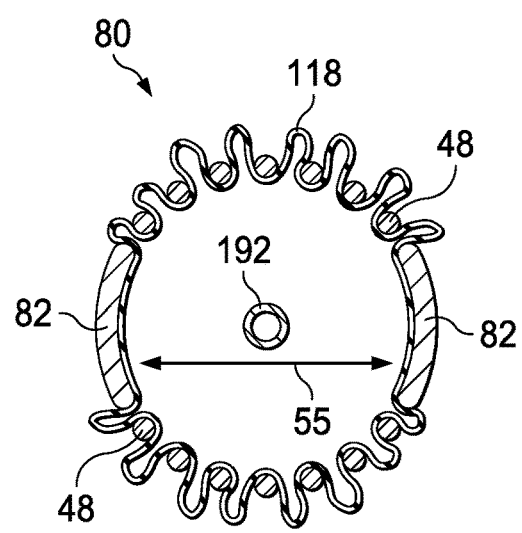
FIG. 29H is an axial cross-sectional view of the inflatable implant of FIG. 29G without the delivery cannula wherein the inflatable member is partially inflated.
Figure 29I:
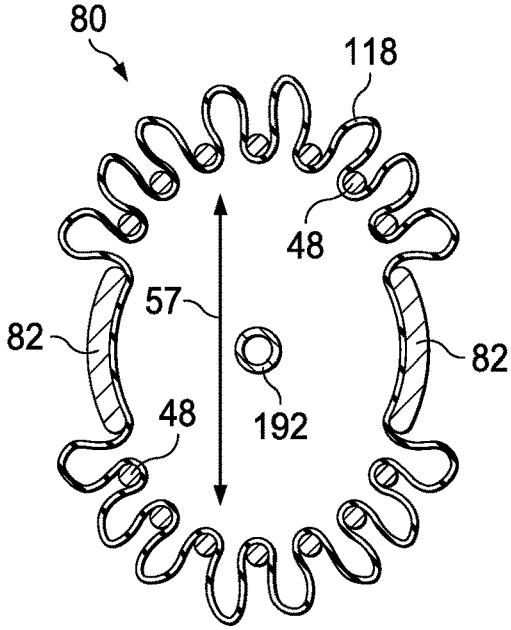
FIG. 29I is an axial cross-sectional view of the inflatable implant of FIG. 29G without the delivery cannula similar to FIG. 29H but demonstrating further inflation and expansion of the assembly.
Figure 29J:
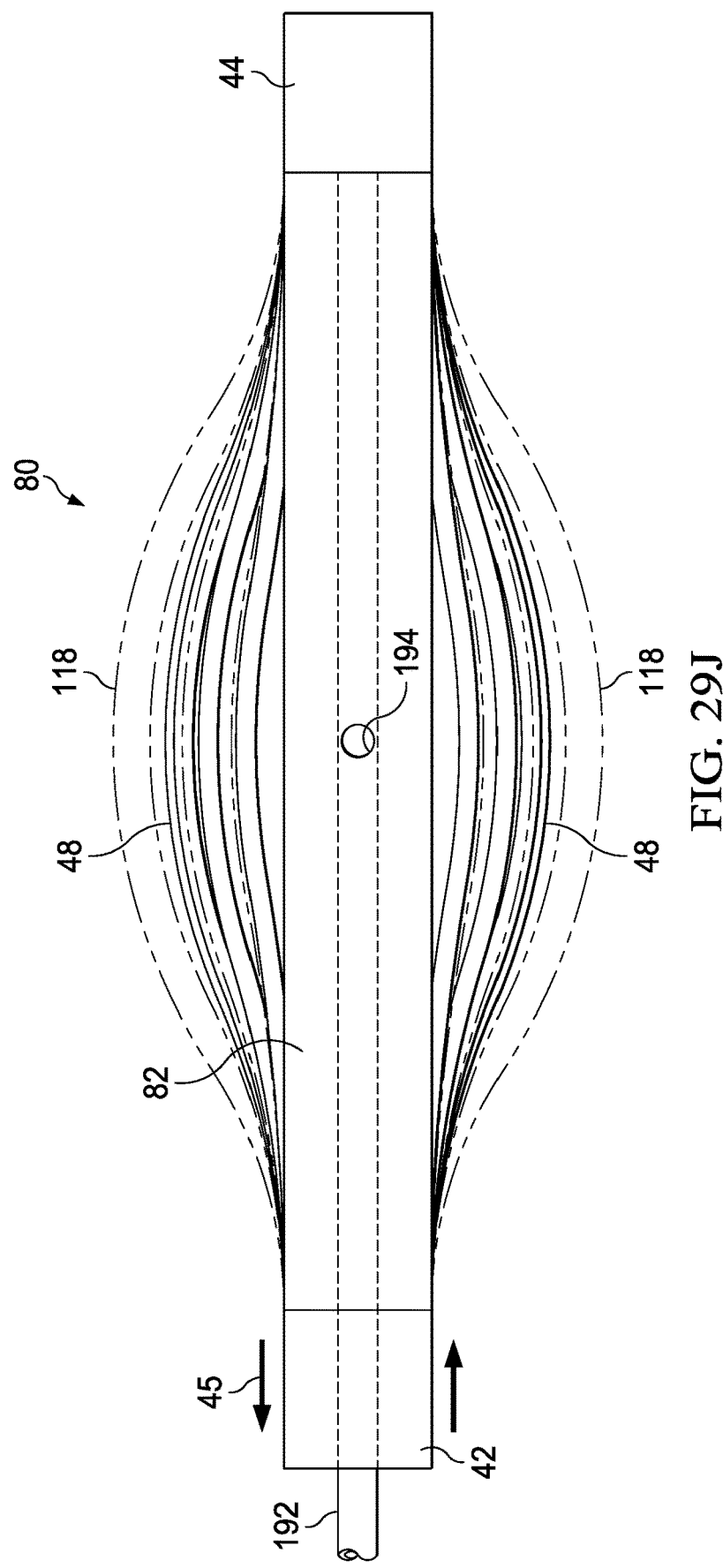
FIG. 29J is a schematic lateral perspective view of the inflatable implant of FIG. 29I showing interdigitation of the inflatable member through gaps between the wire filaments and the pair of laterally placed ribbons.

With reference to FIGS. 29D-29F, in some embodiments, a kyphoplasty implant 70 that includes an inflatable member 118 and a constraining jacket 250 may be movable in and out of a delivery cannula 414. When the implant 70 is within the delivery cannula 414, the implant 70 may assume a collapsed, reduced diameter profile as shown in FIG. 29D. When the delivery cannula 414 is retracted relative to the implant 70, or the implant 70 is moved beyond the tip of the delivery cannula 414, the implant 70 may expand to a larger diameter due to the action of pressurized inflation of the inflatable balloon member 118 therein as shown in FIG. 29E. In this expanded position, the implant may assume a 3-dimensional shape that is configured to expand and stabilize the fractured vertebral segment in which implant 70 is implanted. For example, in some embodiments, inflatable implant 70 may include an expandable jacket 250 disposed about an inflatable member 118. An inflation tube 192 (not shown in FIGS. 29D and 29E for clarity) may extend through the inflatable member 118 similar to implant 40 described above. Expandable jacket 250 may include a first portion 70A having a plurality of legs 46 flexibly connected to a fixed ring 44, which may be fixedly attached to the inflation tube 192. Expandable jacket 250 may also include a second portion 70B having a plurality of filaments 48, one end of which may be attached to legs 46 and one end of which may be attached to sliding ring 42. Sliding ring 42 may be slidably attached to the inflation tube 192 as described for implant 40 and as illustrated by arrows 45. In some embodiments, filaments 48 may be connected to sliding ring 42 at a joint. The joint may be a crimp, solder, weld, or any other mechanism known for connecting the ends of at least two wires or similar structures to the ring 42. In a collapsed state, implant 70 may be disposed within a delivery cannula 414 as shown in FIG. 29D (in which inflatable member 118 is not shown for clarity). When the delivery cannula 414 is retracted from implant 70, implant 70 may be inflated into an expanded state as shown in FIG. 29E.

In some embodiments as shown in FIG. 29F, legs 46 may be composed of a plurality of wires 72 which may be substantially wedge-shaped in cross-section and spaced apart by a multi-lobe inflatable member 118, such as a trefoil balloon in which each lobe may be filled simultaneously or sequentially with hardenable fluid as described herein, wherein the multi-lobe balloon 118 and the wedge-shaped wires 72 may assume the configuration of a rosette, for example. The adjacent disposition of the balloon 118 and wires 72 within the delivery cannula 414 may substantially fill the cross-sectional area of the delivery cannula 414 in which the members are disposed. In such embodiments, for a given cross-sectional area filled by the wires 72 and multi-lobe balloon 118, the wires 72 and balloon 118 are capable of fitting into the lumen of a tubular delivery cannula 414, and a small amount of space can be left between the wires 72 and the balloon 118 to facilitate frictionless sliding of the implant within the delivery cannula 414 during deployment. In some embodiments, wires 72 may be formed from helical wires that are substantially wedge-shaped in cross-section and assume a minimal profile when packed with inflatable member 118 in the interior of housing 102 or within delivery cannula 414. Alternatively, rounded, flat-shaped, or other cross-sectional shapes may be used for wires 72, or a combination thereof. In some embodiments, wires 72 may exhibit good resistance to twisting and bending, while being capable of being formed into various shapes not normally achieved with flat wires. Wires 72 are shown configured in a wire assembly packed into the interior of a housing 102 or delivery cannula 414, including three wedge-shaped wires 72 for adjacent disposition within the housing so as to substantially share the inflatable member 118 within the cross-sectional area of the housing or delivery cannula in which the wires are disposed. In some embodiments, the wires 72 collectively include the inflatable member 118 therebetween to assume an approximately cylindrical form to substantially fill the lumen of the housing 102 or delivery cannula 414. The shapes of the wires 72 may be configured to accommodate the interposed inflatable member 118 so that there is a minimum of unoccupied space in the lumen of the housing 102 or delivery cannula 414.

In certain embodiments of the spinal implants of the present invention, an implantable expandable jacket-balloon combination may include a plurality of proximal portion filaments and a plurality of distal portion filaments wherein the filaments in each portion vary in number, caliber, flexibility, or a combination thereof. The gaps between the filaments in the proximal jacket portion may be narrower or wider than the gaps between the filaments in the distal jacket portion. Upon pressurized inflation of the balloon member, (a) the balloon may protrude through the gaps between the filaments, (b) the filaments may be spread apart and bow outwards as the balloon expands, and (c) the sliding ring may translate toward the central portion of the implant along the course of the inflation cannula.

With reference to FIGS. 29G-29J, in certain embodiments, an implant 80 having an inflatable balloon-expandable jacket assembly may be loaded in a delivery cannula 414. Implant 80 may include an inflatable member 118 and an expandable jacket disposed about the inflatable member 118, the expandable jacket including a plurality of filaments 48 and a plurality of ribbons 82. In some embodiments, ribbons 82 may be made of a relatively stiffer material than filaments 48. An inflation tube 192 having an orifice 194 may extend through the interior of the inflatable member 118 to facilitate expansion of inflatable member 118 with a hardenable fluid as described herein. Implant 80 may have a proximal end and a distal end wherein the plurality of filaments 48 and the plurality of ribbons 82 extend between the proximal end and the distal end. For example, in some embodiments, the filaments 48 may extend along one or more of a medial quadrant, a lateral quadrant, a cephalad quadrant, and a caudal quadrant (cephalad and caudal shown for simplicity and clarity). In lieu of a quadrant arrangement, filaments 48 may be arranged in any suitable configuration (e.g., halves, thirds, irregular, or other configurations). In certain applications, the filaments 48 in each of those quadrants or other arrangements may be of the same material and configuration. In other applications, the filaments 48 in those quadrants or other arrangements may be of different materials and may have different configurations. In certain applications, the filaments 48 may be formed of spiral type ribbons having selected applied cross-curvature that determines differential and directional expansion of the implant 80 within a particular fractured vertebral body. Filaments 48 and ribbons 82 may be attached to a sliding ring 42 at one end and to a fixed ring 44 at another end. Sliding ring 42 may be slidably mounted to inflation cannula 192 as indicated by arrows 45 to help facilitate expansion as described herein. Fixed ring 44 may be fixedly attached to inflation cannula 192. In some embodiments, the relatively greater stiffness of ribbons 82 compared to filaments 48 may cause relatively lesser lateral expansion (as indicated by arrows 55) and relatively greater vertical expansion (as indicated by arrows 57) as inflatable member 118 is expanded with hardenable fluid. As inflatable member 118 expands, it may bulge outward at multiple locations between the filaments 48 and ribbons 82 as shown, which facilitates interdigitation of the implant 80 in the cancellous bone, thereby enhancing stability of implant 80 within the vertebra in which it is implanted.

In some embodiments, an expandable jacket 250 as described herein may be disposed about inflatable member 118 to control the direction and amount of expansion of inflatable member 118. For example, jacket 250 may include or be composed of an interconnected array of segments of substantially solid but flexible material, such as metal, wire, fabric, fiber, or plastic, for example, or a combination thereof, that have an ability to expand and form an array of openings through which inflatable member 118 may bulge outward under pressure from the hardenable fluid material. The bulges of inflatable member 118 through the openings of expandable jacket 250 may help facilitate interdigitation of inflatable member 118 into various regions of cancellous bone 12, thereby enhancing the stability of the implant within a vertebral body 10. In some embodiments, the bulges may extend out beyond jacket 250 about 2-4 mm, for example, or other suitable amount. In some embodiments, jacket 250 may be secured to inflatable member 118 only at its proximal and distal ends. Alternatively, jacket 250 may be secured to inflatable member 118 at other locations. The maximum expansion and direction of expansion of inflatable member 118 may be controlled by the size and configuration of the jacket 250. In some embodiments, the amount of bulging and interdigitation may be controlled by selection of appropriate combinations of various parameters, such as the durometer and thickness of inflatable member 118, the material properties and dimensions of jacket 250, the number, sizing, shape, and orientation of openings (which may or may not be the same or different throughout jacket 250), and the pressure, temperature, and viscosity of the hardenable fluid material. In some embodiments, one or more protrusions may be formed on an exterior surface of inflatable member 118 to interdigitate with cancellous bone 12 and help prevent unwanted movement of the kyphoplasty implant following expansion of inflatable member 118. The protrusions may be disposed regularly or irregularly about inflatable member 118 with respect to openings in jacket 250, for example, or without regard to such openings if no jacket 250 is used, for example. In some embodiments, inflatable member 118 may be made by incorporating protrusions into inflatable member 118 in a blow mold via a heat set process similar to processes used to form angioplasty or kyphoplasty balloons, for example. In some embodiments, thermoplastic or thermoset polymeric material approved for long-term implantation may be used to manufacture inflatable member 118, including silicone, polyethylene, polyethylene terephthalate (PET), arnitel, hydrel, polyether ketone (PEEK), PEBAX™, TEFLON™ (The Chemours Company, Wilmington Del.), other polyolefins, and combinations thereof, for example.

Figure 30:
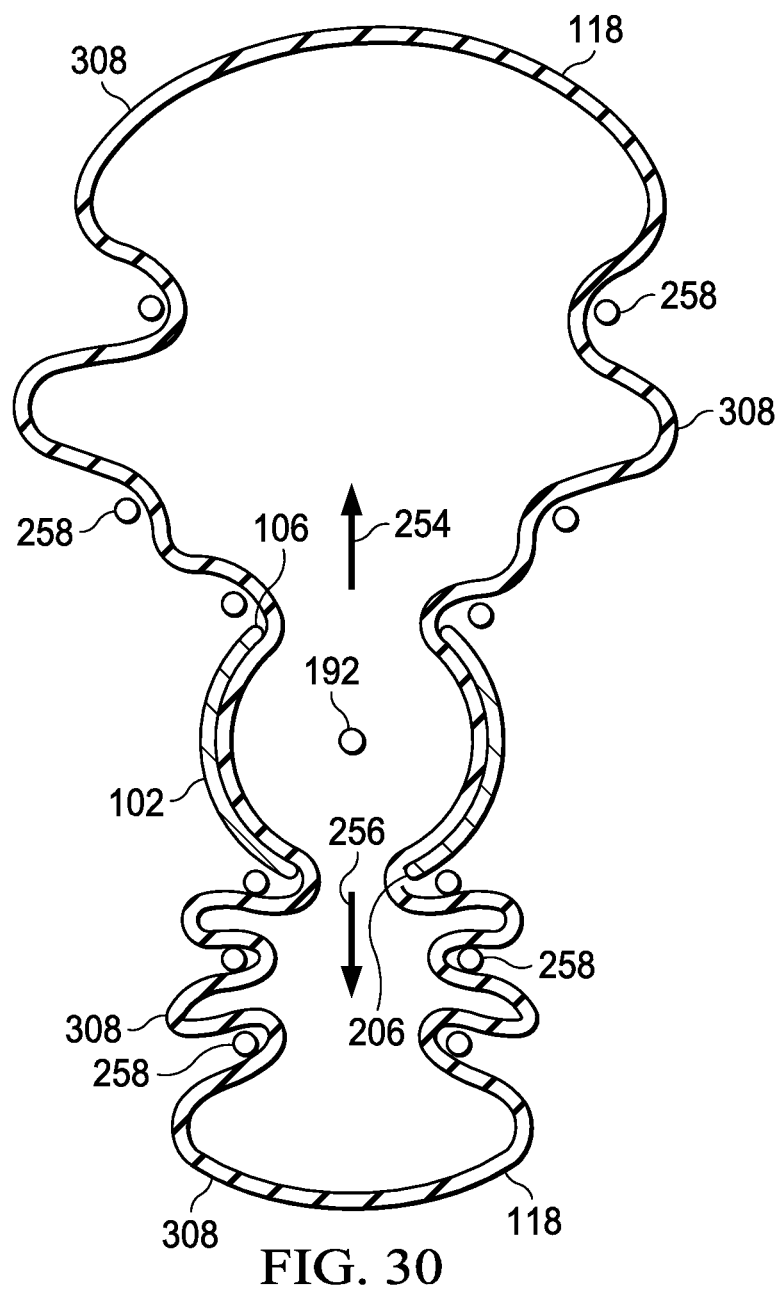
FIG. 30 is an axial cross-sectional view of an intermediate portion of another embodiment of an implantable prosthesis including an inflatable member and an expandable jacket extending out of a housing in two directions.

In some embodiments, when installed in a vertebral body 10, an implant as described herein may be selectively positioned and oriented such that the one or more slots 106 in housing 102 are directed toward one or more specific regions of the vertebral body such that when an inflatable member 118 is expanded by pressurized hardenable fluid material, the inflatable member 118 will expand directionally, and in some instances differentially, into the one or more specific regions of the vertebral body that need to be expanded to correct the particular kyphosis. For example, referring to FIG. 30, an implant is shown in which the housing 102 has two slots 106 and 206 that face in opposite directions 254 and 256, respectively. Such an implant may be used, for example, when a vertebral body needs restoration of lost vertebral volume in each of two regions that lie on opposite sides of the implant when the implant is properly positioned and oriented within the vertebral body. As shown in FIG. 30, in some embodiments, the segments 258 of jacket 250 described above may be configured such that inflatable member 118 will expand differentially to achieve a first amount of expansion in a first direction 254 and a second amount of expansion in a second direction 256. Alternatively, in some embodiments, inflatable member 118 may expand substantially the same amount in both the first direction 254 and the second direction 256. Additionally, in some embodiments, the segments 258 of jacket 250 and inflatable member 118 may be configured such that inflatable member 118 will form a different number, size, position, and shape of bulges 308 in direction 254 than direction 256. Alternatively, in other embodiments, the segments 258 of jacket 250 and inflatable member 118 may be configured such that inflatable member 118 will form substantially the same number, size, position, and shape of bulges 308 in direction 254 as direction 256 (e.g., a mirror image thereof). In some embodiments, inflation of inflatable member 118 may expand it directionally and differentially to assume a substantially larger deployed state in a chosen area of osteoporotic fracture, for example.

Figure 32:
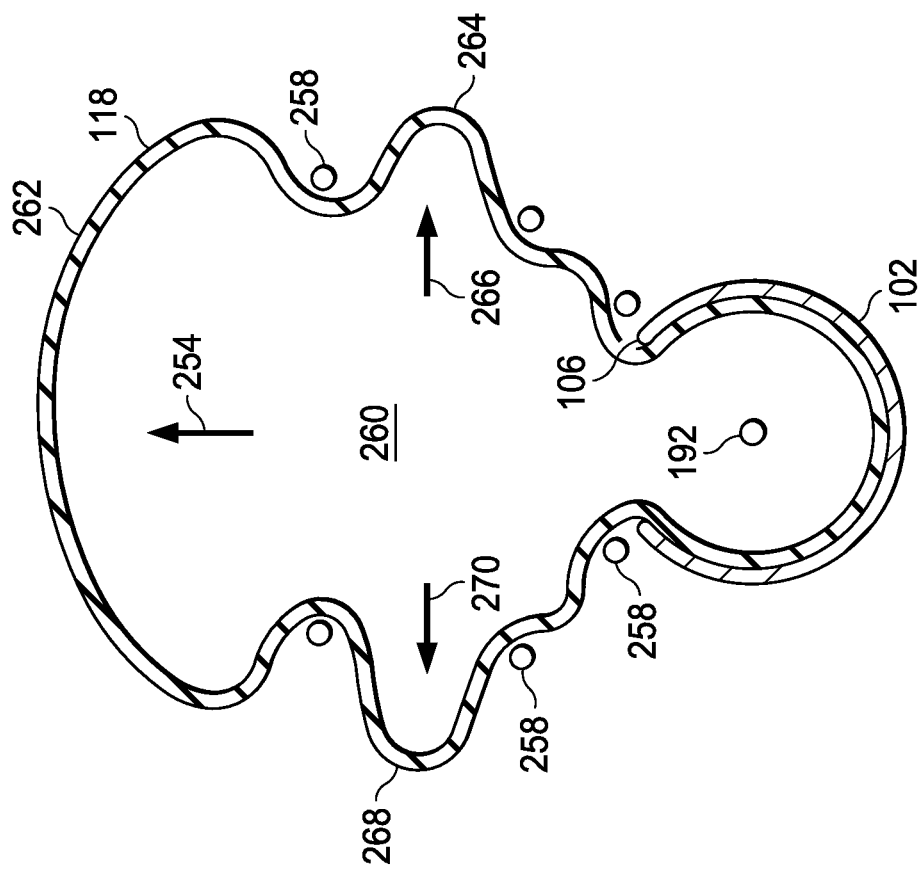
FIG. 32 is an axial cross-sectional view of the implantable prosthesis of FIG. 31 in which the inflatable member and expandable jacket are shown in an expanded configuration extending out of the housing.
Figure 31:
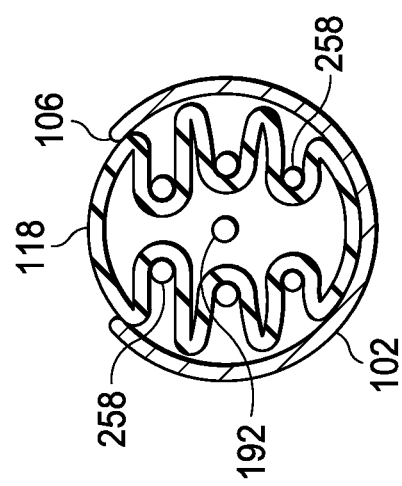
FIG. 31 is an axial cross-sectional view of an intermediate portion of another embodiment of an implantable prosthesis including an inflatable member and an expandable jacket shown in a contracted configuration within a housing.

As another example, FIGS. 31 and 32 illustrate another embodiment of an implant in which the housing 102 has a single slot 106 such that the inflatable member 118 expands primarily in one radial direction 254 with respect to a longitudinal axis of housing 102 (e.g., an axis along which a centerline of internal cannula 192 is disposed). Inflatable member 118 is shown in a collapsed condition in FIG. 31 (which facilitates a compact delivery state within housing 102 until the desired time for expansion) and in an expanded condition in FIG. 32. In an expanded condition, segments 258 of jacket 250 may be configured to cause the expansion chamber 260 of inflatable member 118 to form a plurality of bulges in desired sizes and directions. For example, in some embodiments, the bulges of inflatable member 118 may include a relatively large bulge in an apical portion 262 that is generally directed in a radial direction 254 and relatively smaller bulges in medial portions 264 and 268 that are generally directed in lateral directions 266 and 270, respectively. Of course, any desired arrangement of bulges may be formed by appropriate configuration of jacket 250 and inflatable member 118. In view of the expansion of inflatable member 118 radially outward from the central axis of housing 102, the embodiments illustrated in FIGS. 30-32 (as well as other similar embodiments described herein) may generally be referred to as a radially expandable prosthesis. As described herein, in some embodiments, radial expandability of inflatable member 118 may be limited in certain directions by a constraining means such as jacket 250.

As shown in FIGS. 37A and 37B, a human vertebra typically includes a vertebral body 10 having a fairly thin layer of cortical bone 14 (also known as cortex, which is a relatively hard and dense type of osseous tissue) about its periphery and cancellous bone 12 (also known as trabeculae, which generally has a lower density and hardness compared to cortical bone) in its interior. The architecture of the vertebral body 10 is thus composed of porous trabecular bone and dense, solid cortex. A vertebral arch 16 is formed by two pedicles 18 and laminae 20. Pedicles 18, which are relatively short and strong, extend generally posteriorly from the sides of the vertebral body 10 to help form the vertebral arch 16. Along with a posterior portion of vertebral body 10, vertebral arch 16 defines a spinal canal 22 in which a spinal cord (not shown) is disposed. A transverse process 28 extends generally laterally from each side of vertebral arch 16, and a spinous process 34 extends posteriorly from vertebral arch 16. Vertebral body 10 includes an upper end plate 24 and a lower end plate 26 which respectively form the upper and lower surfaces of the vertebral body 10. The end plates 24, 26 are formed from a thickened layer of cancellous bone, the top layer being dense and relatively strong especially along the outer third of the end plates. Vertebral arch 16 and processes 28, 34 generally have thicker layers of cortical bone. Generally, either a transpedicular route 30 or a parapedicular route 32 may be used to install an implant for kyphoplasty, as described further herein.

In reference to FIGS. 37A and 37B and FIGS. 38-47, an exemplary method of inserting a vertebral implant within a vertebral pedicle or parapedicular cortex will now be described. Although a unipedicular approach may be feasible, where a fractured vertebral body is considered relatively stable, the present method is particularly applicable to severe or unstable fractures whereby a bi-pedicular approach or bi-parapedicular approach is considered more appropriate to adequately stabilize a vertebral implant. The transpedicular approach is the most commonly used; however, small pedicle size, especially in the upper thoracic spine, may preclude the use of large-bore needles (e.g., 10-11 gauge). In some embodiments, reducing needle size to 13 gauge may make the procedure more feasible below the level of T4. In the parapedicular approach, the guide pin passes along the lateral aspect of the pedicle, and the guide pin is angled more towards the center of the vertebral body than does the transpedicular approach. In some embodiments, the parapedicular approach may be riskier than the transpedicular approach due to the higher incidence of pneumothorax or bleeding after needle removal (the flanged collar theoretically may tamponade potential bleeders), for example.

Figure 41:
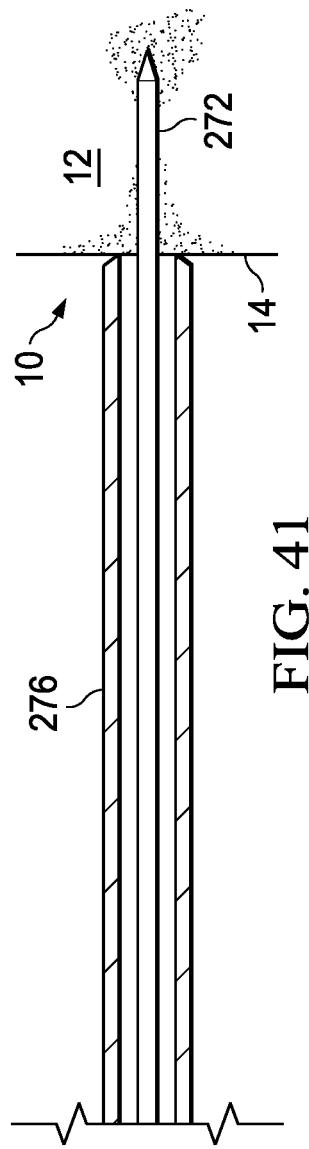
FIG. 41 is a cross-sectional view of the guide pin and second tissue dilator of FIG. 40, the first tissue dilator having been removed.
Figure 42:
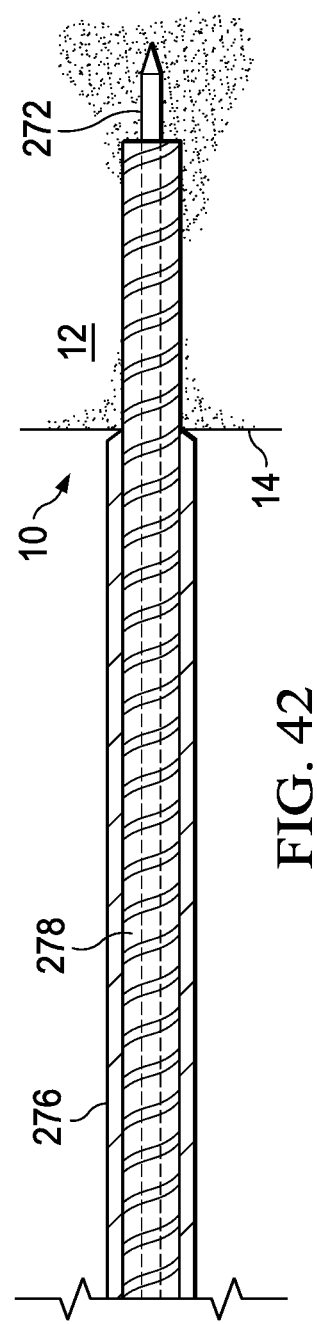
FIG. 42 is a cross-sectional view of the guide pin and second tissue dilator of FIG. 41 and a cannulated drill bit disposed within the second tissue dilator and about the guide pin.
Figure 43:
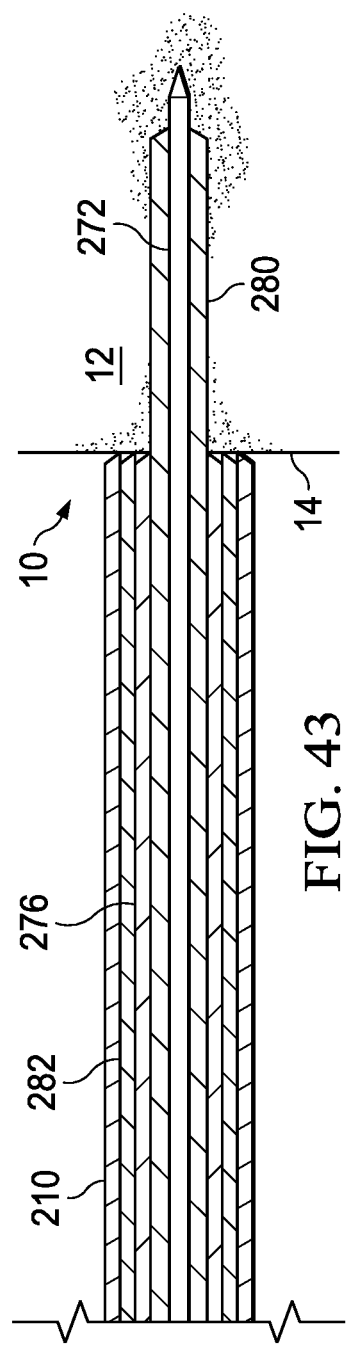
FIG. 43 is a cross-sectional view of the guide pin of FIG. 42, the drill bit having been removed, an obturator in place of the drill bit, an inner cannula disposed about the obturator, an intermediate cannula disposed about the inner cannula, and an access cannula disposed about the intermediate cannula.

Referring again to FIGS. 38-47, this series of figures illustrates a sequence of steps that may be performed to install an implant in a vertebral body 10 as described herein. As shown in FIG. 38, a guide pin 272 may be inserted through the cortical bone 14 and into a portion of the cancellous bone 12 of the vertebral body 10 to serve as a stabilizing and orienting member. Guide pin 272 may enter the pedicle base, as seen on a fluoroscopic image, which arises from the confluence of the pedicle cortical walls joining the vertebral body. The guide pin 272 may be tapped with a mallet into the cortical bone through the pedicular medullary canal and into the vertebral body 10. In some embodiments, the guide pin 272 may penetrate to a depth in the range of about 60%-70% across the vertebral body 10. The location and orientation of guide pin 272 may be selected to achieve a desired placement and orientation of the implant as described further below. As shown in FIG. 39, a tissue dilator 274 may be installed about guide pin 272 to begin to expand a path for other surgical components as described further below. Tissue dilator 274 may include a sharp tip to help hold tissue dilator 274 in place on the cortical bone 14 until the surgeon desires to remove tissue dilator 274. As shown in FIG. 40, an inner cannula 276 may be installed about tissue dilator 274, which may further expand the surgical path. Inner cannula 276 may also include a sharp tip to help hold inner cannula 276 in place on the cortical bone 14 until the surgeon desires to remove inner cannula 276. As shown in FIG. 41, after inner cannula 276 is in place, tissue dilator 274 may be removed, thus leaving an annular space in which a cannulated drill bit 278 may be inserted about guide pin 272 as shown in FIG. 42. Drill bit 278 may be used to form an implant insertion path 284 in vertebral body 10 as shown in FIGS. 45 and 47. The drill bit 278 may be of substantially the same outer diameter as the tissue dilator 274 and dimensioned to slide smoothly within the inner cannula 276. The drill bit 278 may be rotated and advanced through the pedicular medullary canal and into the vertebral body 10 forming an implant insertion path 284. The drilling depth may be monitored by fluoroscopy to the tip of the guide pin 272. The cannulated drill bit 278 may be withdrawn and replaced with a blunt tip obturator 280, which may be of substantially the same dimension as the cannulated drill bit 278 and may fit within the inner cannula 276. As shown in FIG. 43, after drill bit 278 is removed, obturator 280 may be inserted within inner cannula 276 and into the implant insertion path 284 of the vertebral body 10. Still referring to FIG. 43, an intermediate cannula 282 may be installed about inner cannula 276, and an access cannula 210 may be installed about intermediate cannula 282. Each of intermediate cannula 282 and access cannula 210 may likewise include a sharp tip to help hold them in place on the cortical bone 14 until the surgeon desires to remove them. Intermediate cannula 282 and access cannula 210 serve to further expand the patient's tissue to facilitate formation of a path of sufficient diameter to permit insertion of an implant as described herein. As shown in FIG. 44, with the guide pin 272, obturator 280, and access cannula 210 held firmly in position, inner cannula 276 and intermediate cannula 282 may be removed, thus leaving an annular space between obturator 280 and access cannula 210 sufficient to permit insertion of an external fastener 126 using an insertion tool 200 as shown in FIGS. 45 and 46. As shown in FIG. 47, insertion tool 200 may also be used to insert implant 100 through access cannula 210 and external fastener 126 and into implant insertion path 284 in vertebral body 10. Implant 100 (or another implant as described herein) may be inserted into vertebral body 10 until its flange 104 abuts collar 128 of external fastener 126 (if such an external fastener is used) or an exterior surface of vertebral body 10. Once the implant is in place within vertebral body 10, the surgeon may use insertion tool 200 to rotate the implant about its longitudinal axis to orient the one or more slots 106 so that the inflatable member 118 will expand into the desired one or more regions of vertebral body 10 (e.g., one or more regions of osteoporotic fracture) when the hardenable fluid material is injected into inflatable member 118 through inflation cannula 220 as described herein.

An aspect of some embodiments of the invention described herein is controlled, directional expansion of the inflatable member 118 as it evaginates out of the slot 106 formed in the housing 102. In some embodiments, inflatable member 118 may be a medical balloon having a wall of varying thickness providing a varying resistance to expansion: thinner material providing lesser resistance to expansion, and thicker material providing greater resistance to expansion, for example. In some embodiments, a multi-layer construction of the inflatable member 118 (e.g., two or more layers) may allow for a relatively compact state within the housing 102 prior to expansion and differential, targeted expansion of inflatable member 118 when hardenable fluid material is injected therein under pressure.

Simultaneous expansion of bilateral implant devices under fluoroscopic observation may be done by slowly increasing the volume and pressure in the connected inflation systems. Initial unfolding of the inflatable members 118 may start at approximately 10 atm. and may increase gradually to about 30 atm. (about 400 psi), depending upon material viscosity, balloon strength, and other design considerations. However, in some embodiments, adequate reduction may be achieved at lower pressures, especially if the pressure increase is done slowly, allowing time for the achieved pressure to decay as it is being monitored by the pressure gauges.

For non-compliant, high strength balloons, the maximal volume of hardenable material delivered to each balloon may depend on the size of the balloon selected for the particular application. In some embodiments, 4.0 ml, 4.5 ml and 5.0 ml balloon volumes are typically chosen. The overall lengths and diameters of the inflatable balloons can be varied, depending on the particular treatment and access site. Typically, the balloon height or diameter may be about 20 mm-30 mm, and its length about 20 mm-40 mm, for example. Of course, any suitable sizing may be employed, depending on the particular application.

The pressure generated initially while inflating the balloons reflects resistance to expansion by the trabecular bone 12. As the balloons reach resistance from the end plates 24, 26, some increase in pressure may be encountered, as the process is being monitored fluoroscopically. However, pressure decay is expected as the depressed end plates are flattened and elevated. At this point, in some embodiments, there may be no need to achieve maximum balloon inflation or further increase in balloon pressure.

In order to achieve simultaneous inflation of bilateral balloons, a 3-way connector may be used to deliver the hardenable material from one common source to both inflatable implant devices. However, bilateral material sources may be chosen. Each inflation device (e.g., inflatable member 118) may be securely connected to a Luer connector and to a separate pressure monitor. Prior to balloon inflation, negative pressure may be applied to each balloon to ensure that it is completely collapsed and to extract any gas from the system. In some embodiments, it may be desired to render the hardenable material radiopaque and to monitor balloon inflation by biplane x-ray control, for example. A 3-way connector may be used to switch hardenable fluid flow back and forth between the two balloons as needed.

Of course, different size connector elements may be provided for transpedicular vs. parapedicular approaches. Furthermore, it will be appreciated that the dimensions of the pedicles, the vertebral level, and degree of osteoporosis should be taken into consideration for appropriate choice of implant dimensions. One of skill in the art will know and select the appropriate dimensions of the implant components and degree of inflation of the expandable balloon appropriate for the different vertebrae and the condition being treated.

Figure 34:
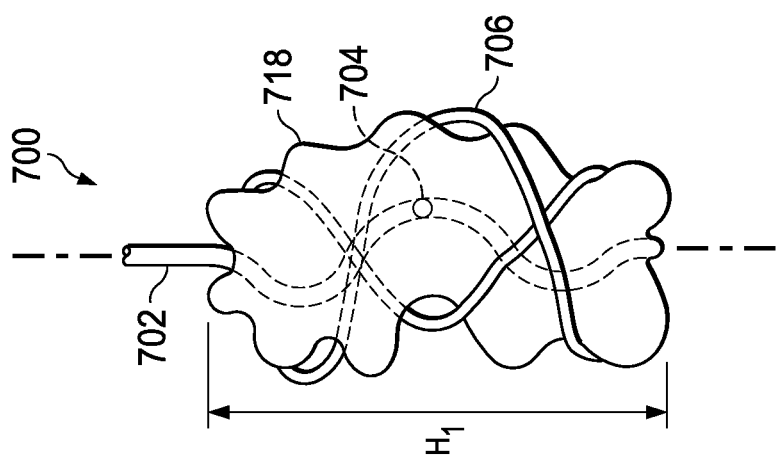
FIG. 34 is a side elevational view of the prosthesis of FIG. 33 shown in a partially expanded state.
Figure 33:
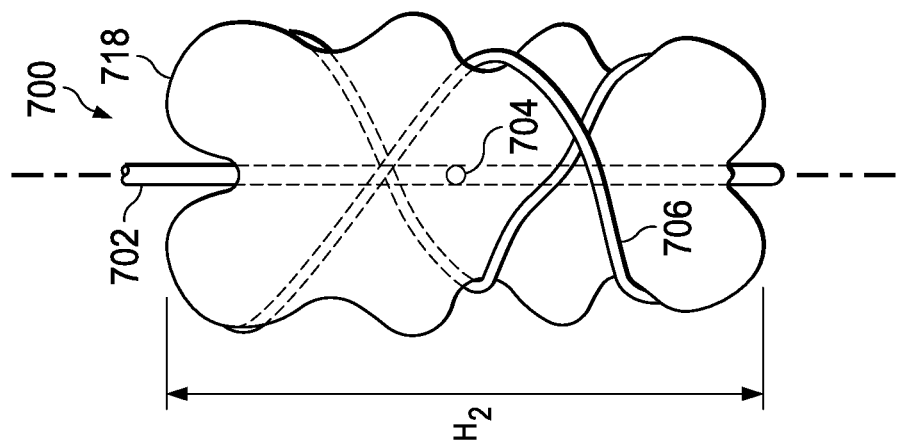
FIG. 33 is a side elevational view of an exemplary embodiment of an inflatable kyphoplasty prosthesis shown in an expanded state.

Referring to FIGS. 33-34, another embodiment of an implant 700 is shown having an inflatable member 718 disposed about a tube 702 to which inflatable member 718 is sealingly connected. A support 706 may be disposed about the inflatable member 718 in a manner designed to control the direction and extent of expansion of the inflatable member 718 as hardenable fluid is injected into inflatable member 718 under pressure through an orifice 704 in tube 702. As described further below, implant 700 may be implanted percutaneously into two adjacent vertebral bodies, crossing the intervertebral disc therebetween to simultaneously treat at least two adjacent osteoporotic fractures. In FIG. 34, implant 700 is only partially inflated with fluid and has a height $H_1$. In FIG. 33, implant 700 is further inflated and has a height H2, which is greater than $H_1$. Implant 700 may be capable of variable expansion, which may be determined by the operator during the implantation procedure. Implant 700 may also be contracted into a minimal profile and loaded into a delivery cannula as explained below.

Figure 35:
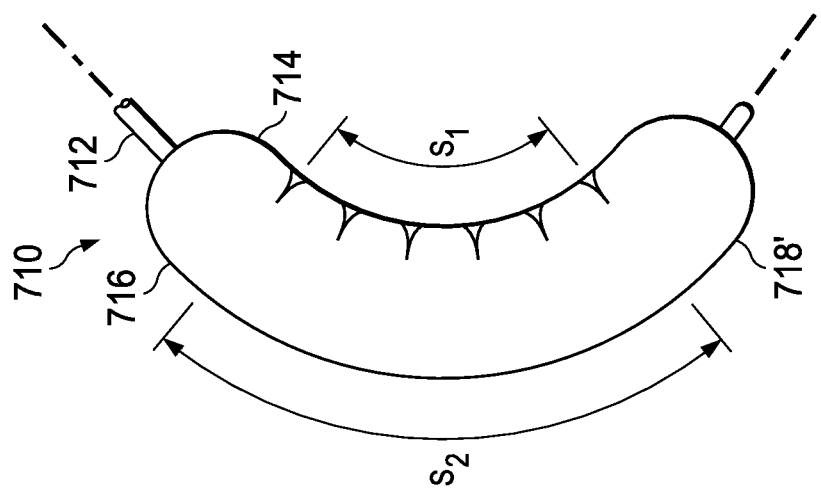
FIG. 35 is a side elevational view of another embodiment of an inflated kyphoplasty prosthesis shown in a curved condition.

Referring to FIG. 35, an alternative embodiment of an implant 710 may include an inflatable member 718' disposed about a tube 712. Inflatable member 718' may be configured to expand in a curved configuration such that an inner surface 714 may have a curved length S 1, and an outer surface 716 may have a curved length $S_2$ that is greater than $S_1$. Such embodiments may facilitate differential expansion of the implant in desired directions to correct spinal deformities.

Referring again to FIGS. 33 and 34, in some embodiments, implant 700 may include an inflatable member 718 with at least two segments positioned upon the inner tube 702 and a support 706 secured to inner tube 702 and/or inflatable member 718 over or along the inner tube 702 at one or more locations, e.g., at a first location proximal to a proximal segment of the inflatable member 718, at a second location between the two segments, and at a third location distal to the distal segment of the inflatable member 718, such that inflation of the inflatable member 718 reconfigures the support 706 to bias the implant 700 to directionally and differentially expand generally by longitudinal elongation of the inflatable member 718 relative to the inner tube 702. In some embodiments, support 706 may be formed from one or more segments of wire, cord, filament, or similar material that is substantially inelastic in a longitudinal direction (that is, substantially resistant to stretching along a length thereof) but is bendable, such as substantially inelastic polymeric material (e.g., nylon, Kevlar™ (DuPont de Nemours, Inc., Wilmington, DE), Spectra, Dacron, Dyneema, Polyimide (PIM), ultra-high molecular weight polyethylene, Zylon™ (PBO) (Toyobo Co. Ltd., Osaka, Japan), and the like, or a combination thereof). Metals such as Nitinol or stainless steel may also be used, for example, or a combination of metal and polymeric material. The material of support 706 may be suitably flexible to be shaped into a low-profile configuration when the balloon (inflatable member 718) is deflated, e.g., for implant loading in a delivery cannula. During balloon expansion, the increasing balloon diameter may urge the fibers, wires, or other elements of the support 706 to deviate away from the most direct path between the first, second, or third locations, or other balloon attachments. Since the fibers of the support 706 have little capacity for stretching, differential expansion of the implant 700 will occur along the path of least resistance, thus achieving the longitudinal lengthening desired to restore vertebral height, for example, primarily directed toward distraction of vertebral end-plates and limiting transverse expansion that may lead to inadvertent retropulsion into the spinal canal. In some embodiments, the support 706 may be separate from the balloon and freely movable relative to the external balloon surface, at least prior to inflation of the balloon. In some embodiments, support 706 may be composed of several helically wound fibers configured into a knit pattern, braid, warp, mesh, or the like, or a combination thereof.

Figure 36:
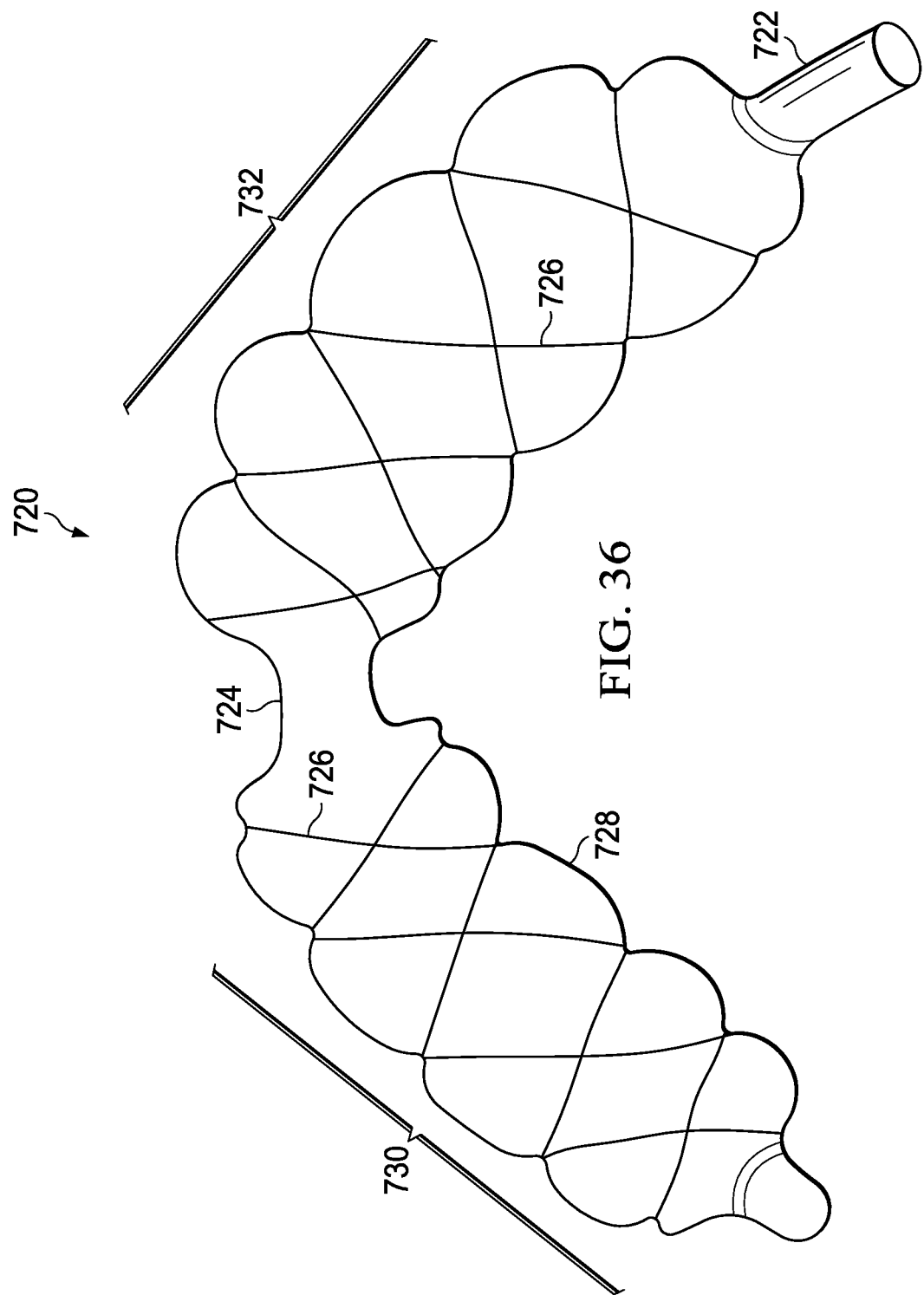
FIG. 36 is a side elevational view of still another embodiment of an inflatable member of a kyphoplasty prosthesis shown in a segmented and curved orientation.

In some embodiments, such as shown in FIG. 36, an inflatable vertebral implant such as implant 720 may be configured to include a supporting structure 726 such as a mesh, braid, warp, or the like, which is carried by a segmented balloon 728 that is disposed about a tube 722. The segmented balloon(s) 728 may take a variety of forms depending on the degree and configuration of segmentation. For example, in some embodiments, balloons 728 may include adjacent segments 730 and 732 that are separated by one or more grooves 724 in an otherwise continuous balloon. The grooves 724 may serve as localized "hinge-points" that act in the manner of bellows imparting differential flexibility to the balloon(s) 728.

In other embodiments, balloons may have deep grooves that separate bulges in the balloon profile, while maintaining modest flexibility to the balloon structure. Other embodiments may include helical balloons to provide a bending or twisting bias in the longitudinal plane, while maintaining flexibility. In other embodiments, balloons may be corrugated whereby adjacent segments on the outer aspect of the bend in the balloon can separate while those on the inner aspect remain in close opposition. The resulting potential for differential lengthening may provide the desired "hoop strength" to correct deformity in patients with severe osteoporotic fractures and significant deformity, and/or angulation.

In some embodiments, balloons useful for vertebral implants as described herein may be constructed of low-compliance materials that tolerate high inflation pressures and attain predictable diameters and configurations in-vivo. Conventional angioplasty and kyphoplasty balloons are typically of uniform cylindrical shape and are of uniform diameter between conical ends and have a central catheter extending along the longitudinal axis of the balloon. When inflated at high pressures, the walls of the balloon are placed into tension and the balloon generally loses its capacity for differential lengthening and hence becomes stiff and biased into a straightened configuration. Such balloons impose this straightened cylindrical configuration on any overlying supporting structure or when implanted into body tissues or organs.

In some embodiments, a supporting structure may be wrapped around or otherwise positioned externally of the balloon. The supporting structure may allow the balloon to retain increased flexibility when deflated and be reduced to a minimal profile for loading into a delivery cannula. To a certain degree, flexibility of the vertebral implant may be maintained at initial stages of inflation and expansion. At higher pressures, the overlying structure may be configured to bias the expandable implant in certain predictable directions in order to achieve deformity correction in a particular clinical setting.

EXAMPLES

The specific examples included below are for illustrative and explanatory purposes and are not to be considered as limiting to this disclosure. Treatment of various vertebral fractures may entail installation of one or more implants (e.g., such as implant 1030, 100, or 230 described above) in a vertebral body 10. For the sake of simplicity, in these examples the implants are generally designated as 100, with the understanding that any suitable implant as described herein may be used, depending on the specific needs of the particular kyphosis being treated.

Example 1

Figure 48:
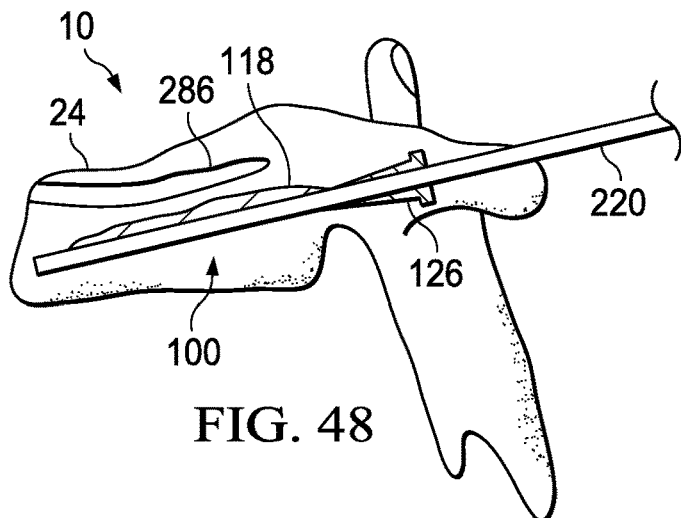
FIG. 48 is a schematic sagittal view of a vertebra having a wedge-shaped compression fracture involving the superior end plate, a horizontal cleft along the inferior margin of the fracture, and a prosthesis and external fastener inserted into the vertebra by a transpedicular approach.
Figure 49:
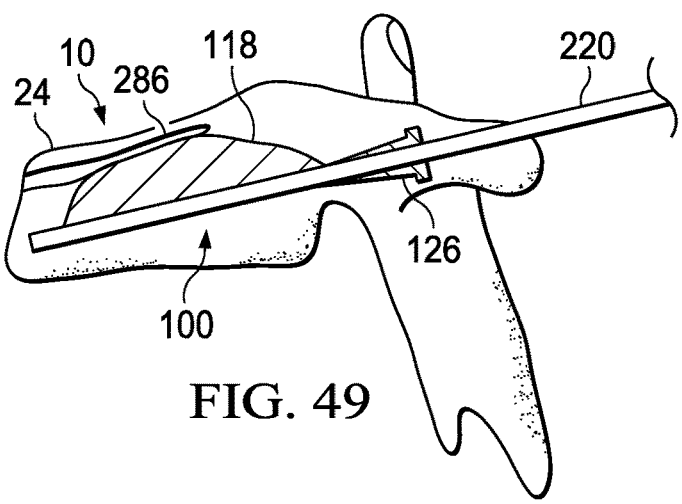
FIG. 49 is a schematic sagittal view of the vertebra, fastener, and prosthesis of FIG. 48 showing partial inflation of a superiorly directed inflatable member with differential expansion towards the superior end plate and flattening and compaction of the horizontal cleft.
Figure 50:
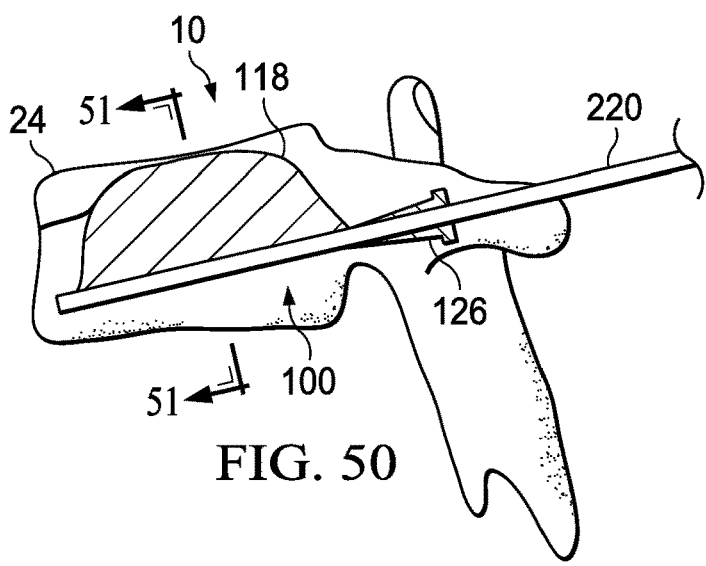
FIG. 50 is a schematic sagittal view of the vertebra, fastener, and prosthesis of FIG. 48 showing elevation of the fractured superior end plate by the inflatable member.
Figure 51:
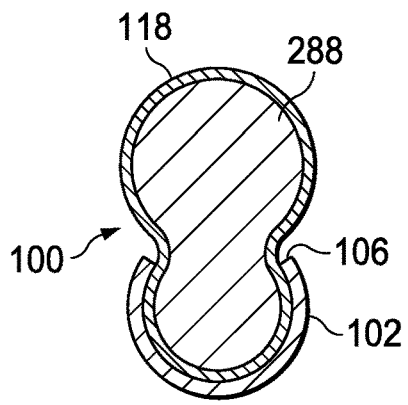
FIG. 51 is a cross-sectional view of section 51-51 of the prosthesis shown in FIG. 50 illustrating a superiorly directed slot and a directionally expanded inflatable member.

Referring to FIGS. 48-51, a first example of a kyphoplasty implant procedure is illustrated. In this example, as shown in FIG. 48, an osteoporotic vertebral compression fracture (VCF) of an upper lumbar vertebral body 10 is shown which involves the superior end plate 24 with around 50% loss of height and anterior wedging. There is depression of the superior end plate 24 and an underlying horizontal cleft 286. The fracture may be dynamically mobile on standing lateral radiography when compared with supine cross-table radiography. The radiographic characteristics of clefts typically evolve over time and sometimes can be indistinguishable from Kummell's disease in severe, persistently mobile, defied osteoporotic VCFs. Guided by magnetic resonance imaging (MRI), for example, or another imaging technique, the VCF may be substantially corrected using an expandable implant 100 as described herein. Treatment may entail installation of an implant 100 in the vertebral body 10 as described above using a bilateral transpedicular or parapedicular approach. In this example, implant 100 is positioned within vertebral body 10 such that a slot 106 in housing 102 is oriented generally upward such that inflatable member 118 may be directed substantially upward from housing 102 toward cleft 286 and superior end plate 24 upon expansion of inflatable member 118 with a hardenable fluid material 288 injected into inflatable member 118 through inflation cannula 220. FIG. 49 demonstrates partial lifting of the superior end plate 24 and appreciable restoration of anterior vertebral height. FIG. 50 demonstrates sufficient expansion of inflatable member 118 to achieve flattening and substantial obliteration of the cleft 286 by the inflatable member 118 such that superior end plate 24 is substantially restored to its normal position and vertebral height of body 10 is substantially restored. In this example, an external fastener 126 has been used to help anchor implant 100 in the desired position in vertebral body 10.

Example 2

Figure 52:
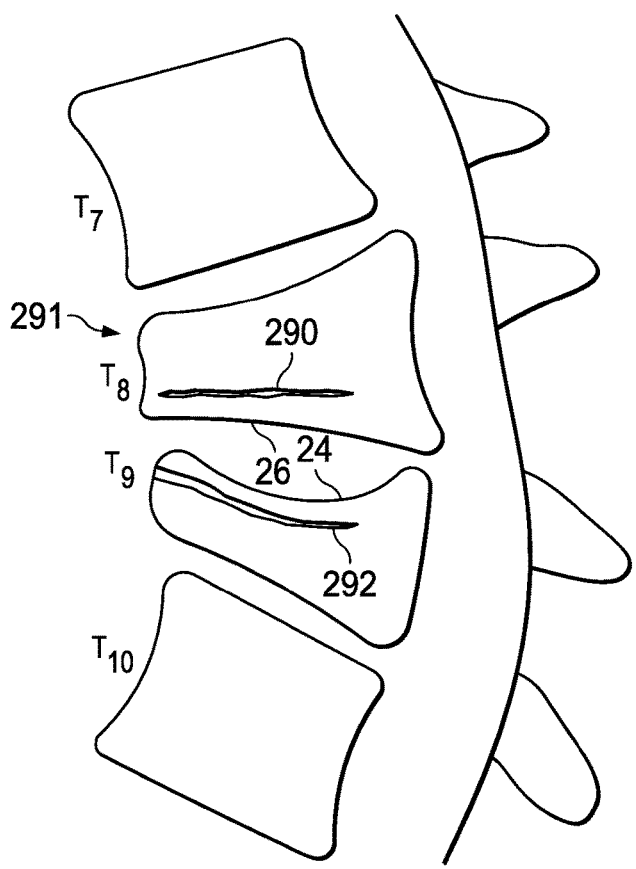
FIG. 52 is a schematic sagittal view of vertebrae T7-T10 showing a wedge-shaped compression fracture of the inferior end plate of T8 and the superior end plate of T9 and kyphotic deformity.
Figure 53:
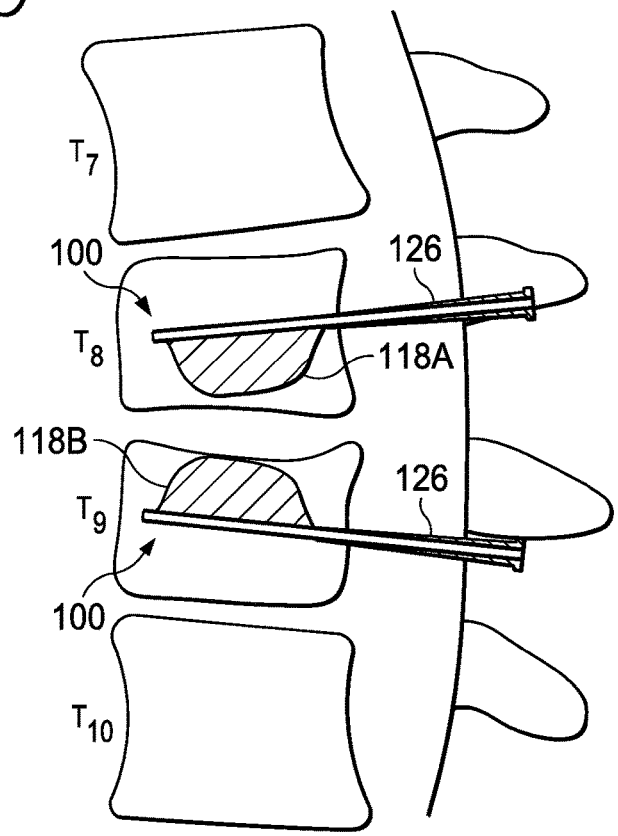
FIG. 53 is a schematic sagittal partially cross-sectional view of the vertebrae of FIG. 52 showing an inferiorly directed inflatable member at T8 and a superiorly directed inflatable member at T9 for correction of the kyphotic deformity.

Referring to FIGS. 52-53, another example is shown involving two contiguous fractures of the mid-thoracic spine, namely, a wedge compression fracture 290 involving the inferior end plate 26 of T8 and a wedge compression fracture 292 involving the superior end plate 24 of T9. There is an associated element of angular deformity and a step-off fracture 291 of the anterior cortex at each level. The distinct fracture lines shown in these figures are usually not visible on lateral radiography; however, they are often visible on computed tomography (CT) scan sagittal reformatted images. Marrow edema is usually visible on MRI images in the acute phase.

According to some embodiments of the present invention, percutaneous therapy may include insertion of stabilizing intravertebral prosthetic implants 100 through bilateral transpedicular approaches. However, in situations whereby the pedicles are too small or are difficult to identify well in fluoroscopy, especially in the upper thoracic spine, a bilateral parapedicular approach may be considered. In this particular case, bilateral prosthetic implants 100 may be inserted at T8 and T9 as shown, and the respective inflatable members 118A and 118B may be expanded generally downward and upward, respectively, to correct the kyphosis. FIG. 53 demonstrates the expected appearance of the expanded prosthetic implants 100. As shown, the inferiorly directed inflatable member 118A at T8 and the superiorly directed inflatable member 118B at T9 have substantially reduced the vertebral end plate compression fractures 290 and 292 and have, at least partially, corrected the angular kyphosis. External fasteners 126 are shown anchoring the implants 100 to the pedicles.

Example 3

Figure 54A:
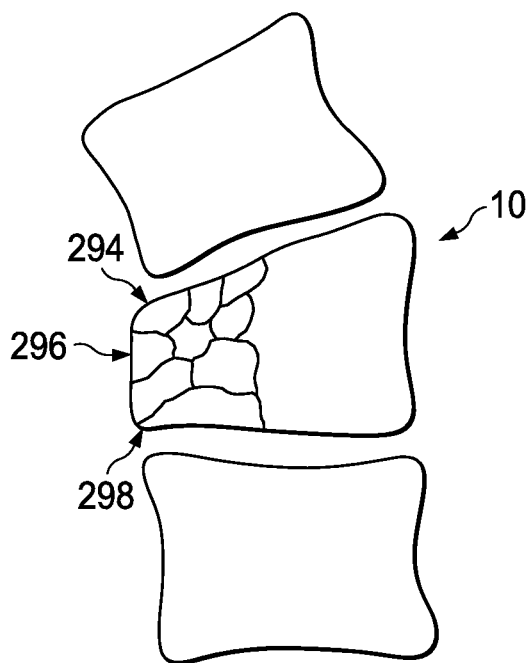
FIG. 54A is a schematic coronal view of a right lateral compression fracture of a thoracic vertebra prior to treatment with an inflatable member as described herein.

FIGS. 54A, 54B, 55A, and 55B illustrate another example involving a right lateral compression fracture, including end plate injuries 294 and 298 and step-off irregular right lateral cortical fractures 296. On the sagittal image shown in FIG. 54B, cup-like superior end plate depression 300 is shown. The coronal image of FIG. 54A shows the presence of lateral angular deformity. This type of fracture may be related to mild trauma, with asymmetric axial load, in a patient with underlying osteoporosis, for example.

Figure 54B:
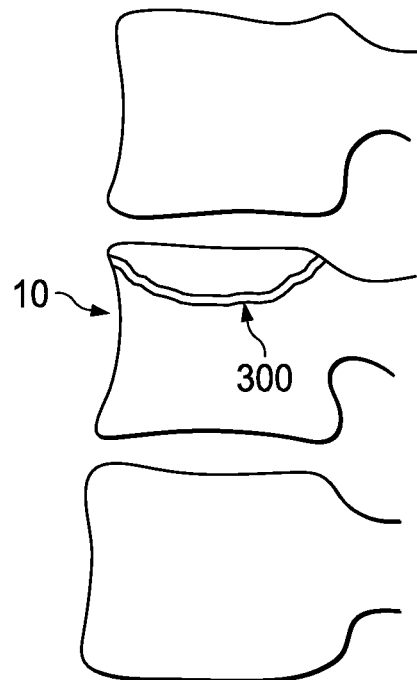
FIG. 54B is a schematic sagittal view of the vertebrae of FIG. 54A.
Figure 55A:
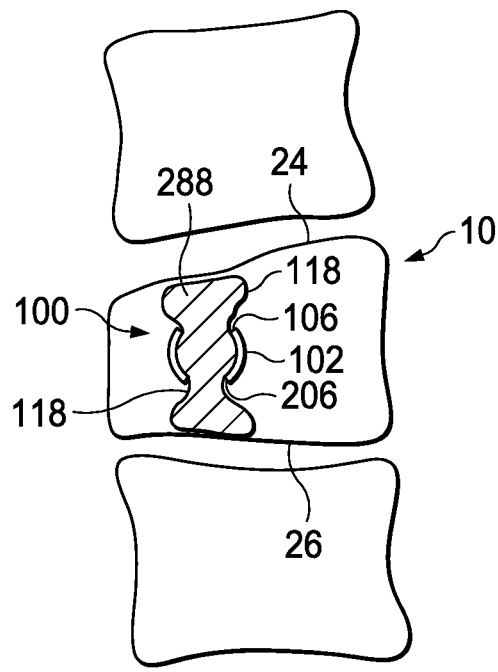
FIG. 55A is a schematic coronal view of the vertebrae of FIG. 54A following insertion and expansion of an inflatable member as described herein, illustrating improvement in vertebral height, correction of deformity, and stabilization of the fracture.
Figure 55B:
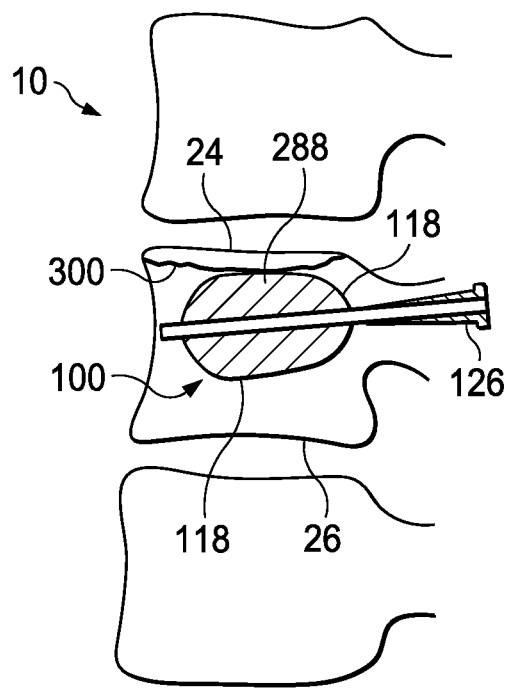
FIG. 55B is a schematic sagittal view of the vertebrae and inflatable member of FIG. 55A.

As shown in FIGS. 54A and 54B, this patient may be treated using a unilateral transpedicular or parapedicular approach with insertion of an implant 100 having superior and inferior slots 106 and 206, respectively, in housing 102. Inflation of inflatable member 118 with isoelastic hardenable material 288 directs the inflatable member 118 through slots 106 and 206 of housing 102 towards the superior and inferior end plates, respectively, of the vertebral body 10. As shown in the coronal image of FIG. 55A, the compressed end plates have been distracted, some degree of height restoration has been achieved, and the angular deformity has been partially corrected. As shown in the sagittal image of FIG. 55B, the cup-like superior end plate depression 300 has been substantially flattened. Most significantly, the prosthetic implant 100 serves to stabilize the fracture and secure the intravertebral prosthetic implant 100 to the relatively stronger pedicles and/or parapedicular cortex. Furthermore, despite the presence of end plate fractures, which in conventional kyphoplasty is likely to be associated with cement leakage (i.e., leakage of hardenable fluid material 288 out of the vertebral body 10), implant 100 may prevent such leakage because a one-way valve (e.g., valve 1059, valve 124, or valve 148 described above) will not allow hardenable fluid material 288 to flow back out of implant 100.

Example 4

Figure 56B:
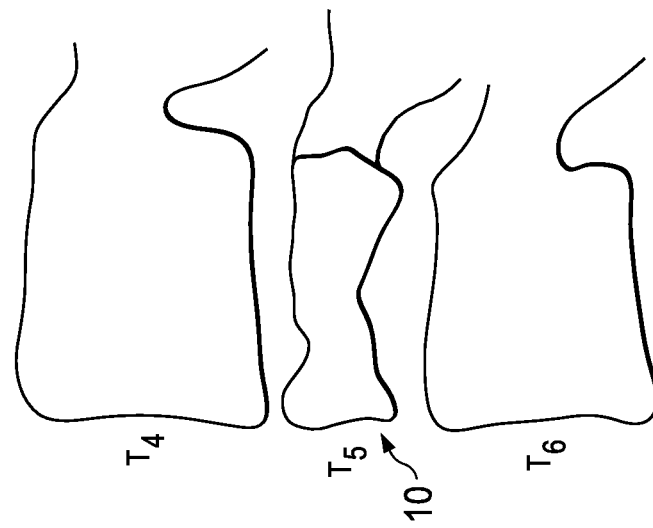
FIG. 56B is a schematic sagittal view of the vertebrae of FIG. 56A shown with the patient lying prone and showing spontaneous increase in vertebral height indicating the presence of abnormal mobility and instability of the fracture.
Figure 56A:
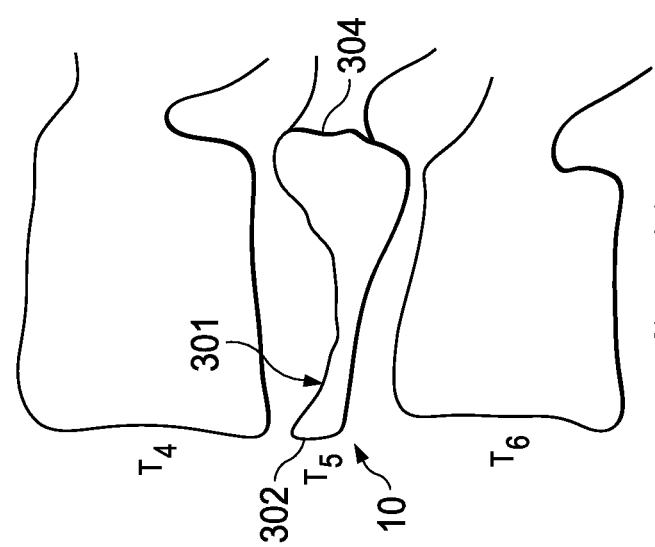
FIG. 56A is a schematic sagittal view of a severely fractured T5 vertebral body shown with the patient standing up.
Figure 56E:
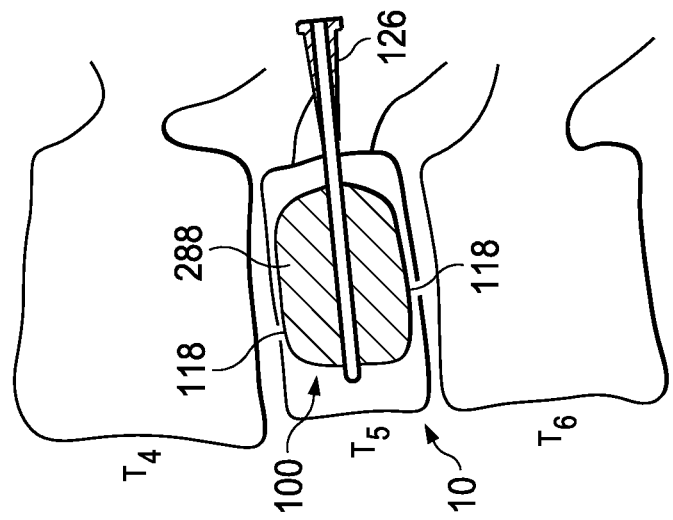
FIG. 56E is a schematic sagittal view of the vertebrae and implants of FIG. 56D with the inflatable members in a further expanded condition and showing flattening of the end plates, vertebral height restoration, and stabilization of the fracture by anchoring the implanted cartridges to the vertebral pedicles.
Figure 56D:
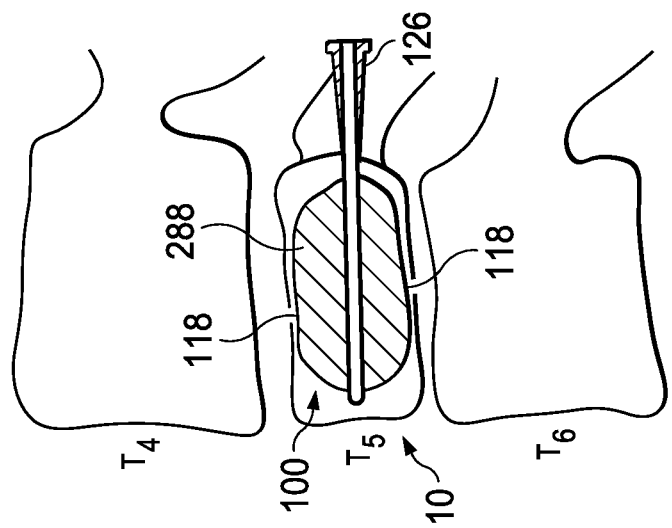
FIG. 56D is a schematic sagittal view of the vertebrae and implants of FIG. 56C with the inflatable members in an expanded condition and showing differentially directed expansion towards the superior and inferior end plates of the T5 vertebral body.
Figure 56C:
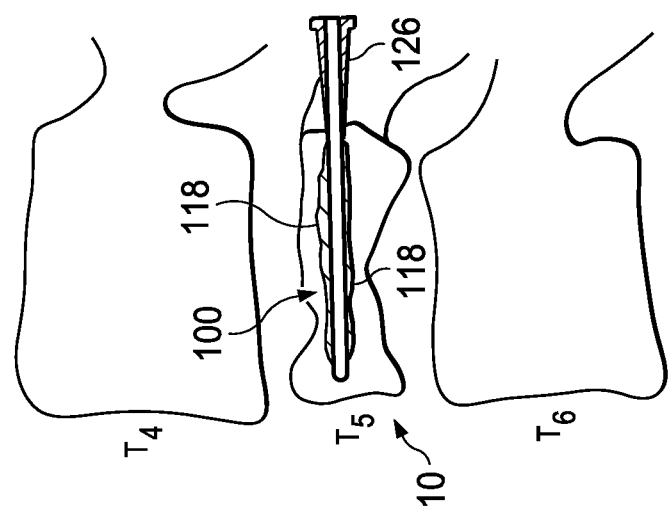
FIG. 56C is a schematic sagittal view of the vertebrae of FIG. 56A showing insertion of bilateral implants with inflatable members in an unexpanded condition.
Figure 56G:
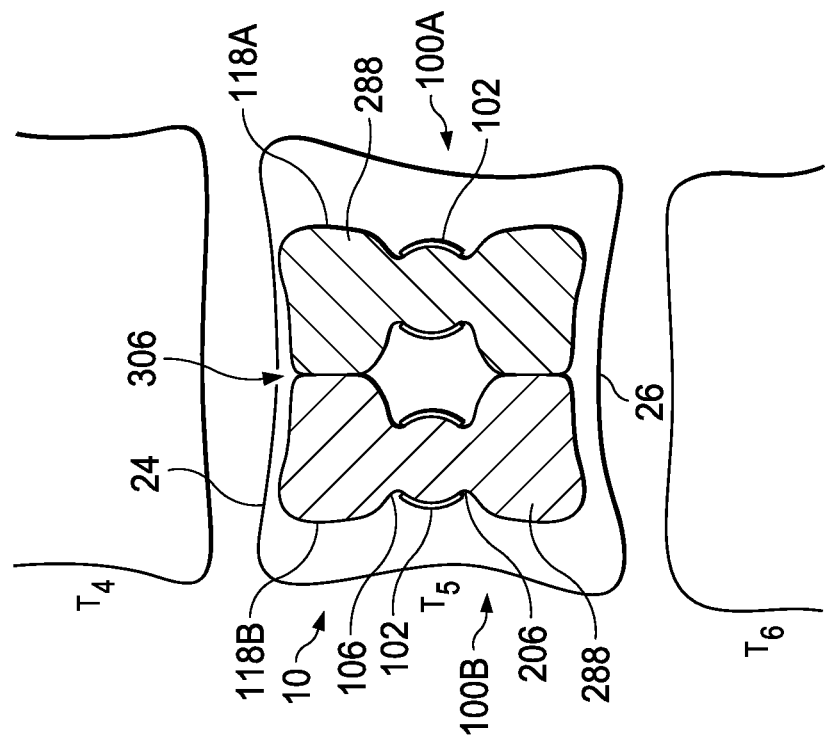
FIG. 56G is a schematic coronal view of the T5 vertebral body and implants of FIG. 56F showing the bilateral implants each having superior and inferior slots, demonstrating differential expansion of the inflatable members toward the superior and inferior end plates.
Figure 56F:
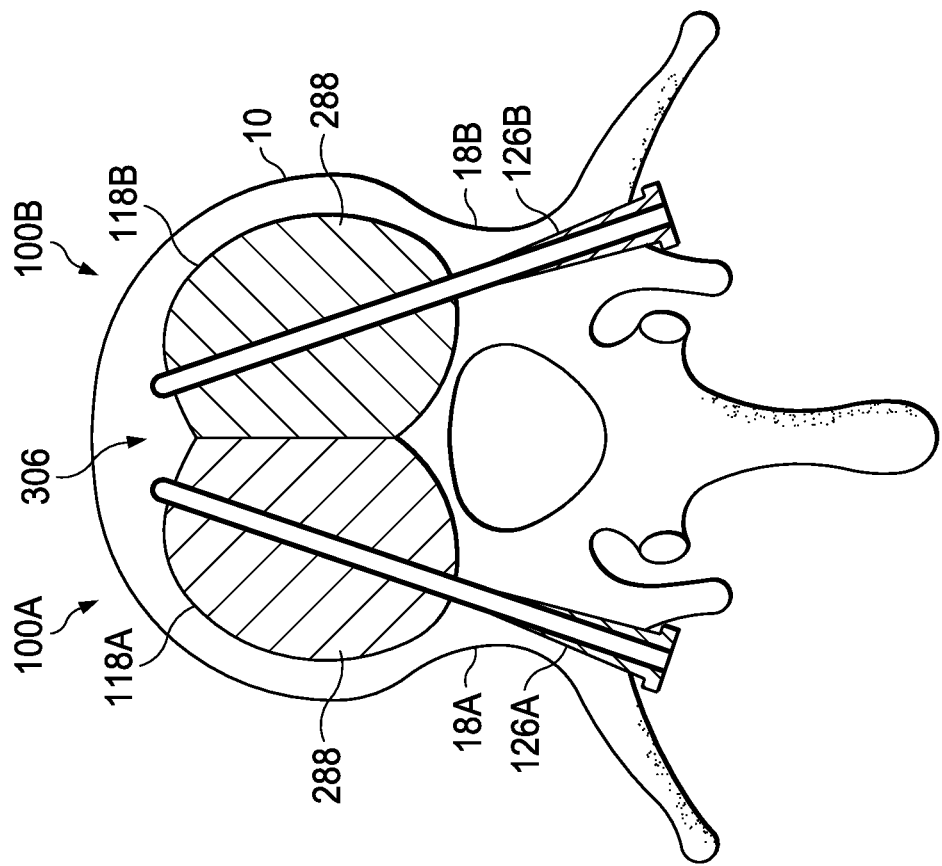
FIG. 56F is a schematic axial view of the T5 vertebral body and implants of FIG. 56E showing the bilateral transpedicular implant insertion and engagement of the inflatable members with each other, which further contributes to implant stabilization.

Referring to FIGS. 56A-56G, another example is shown in which the patient has a severe osteoporotic fracture of the vertebral body 10 of T5 in the upper thoracic spine. As shown in FIG. 56A, there is cup-shaped depression 301 of the superior vertebral cortex with some element of retropulsion 304 of the posterior cortex. There is around 90% loss of height, mostly anteriorly. Because of normal thoracic kyphosis, traumatic injuries with axial load typically affect the anterior portion of the vertebral body 10 more than the posterior portion. FIG. 56B, which is a lateral view taken with the patient lying down, shows improvement in the degree of depression of the fracture. Fluoroscopic observation may confirm the presence of significant dynamic mobility indicating an unstable fracture. Dynamic fracture mobility occurs frequently in patients presenting for treatment of this type of fracture.

Conventional vertebroplasty or kyphoplasty are the current modalities of choice for non-surgical treatment of this type of fracture. However, there is a persistent risk of cement leakage, especially when there is an attempt at achieving some restoration of vertebral height or correction of angulation. There is often success at initial reduction of back pain. However, long term, there is a chance of persistent dynamic mobility and the formation of pseudarthrosis around the injected cement.

The therapeutic choice offered by the present disclosure includes a bilateral transpedicular or parapedicular approach and insertion of bilateral prosthetic implants as described herein with anchoring of the implants to the pedicular or parapedicular cortex. Progressive inflation of the inflatable members with hardenable fluid material, having a durometer close to the durometer of the adjacent vertebrae, for example, is expected to achieve appreciable restoration of vertebral height and, more importantly, stabilization of the vertebral segment. Of course, control of pain, the slowing down of the cascade of progressive instability of the rest of the osteoporotic spine, and reducing the possibility of additional adjacent osteoporotic fractures are also expected.

Referring to FIGS. 56C-56G, an implant 100A and 100B may be inserted into each pedicle 18A and 18B, respectively, of the fractured vertebral body 10. In this example, each implant 100A and 100B has two opposing slots 106, 206 in its housing 102 which allow the respective inflatable member 118A and 118B to expand both superiorly toward upper end plate 24 and inferiorly toward lower end plate 26 upon injection of a hardenable fluid material 288 as shown. External fasteners 126A, 126B may help to anchor implants 100A, 100B to the vertebral body 10. Additionally, in this example, the inflatable members 118A and 118B may also expand laterally until they engage each other along an interface 306, which may further help to stabilize implants 100A, 100B within the vertebral body 10. As illustrated, after inflation of inflatable members 118A and 118B with hardenable fluid material 288, the fractured vertebral body 10 may be substantially restored to its proper height and volume.

Example 5

FIGS. 57A-57H illustrate a severe osteoporotic fracture involving a T8 vertebral body 10, namely, a relatively uncommon centrally oriented fracture involving the superior and inferior end plates 24, 26 with severe central loss of height. A CT scan (not shown) showed gas within the collapsed vertebral body 10, with the gas extending to an adjacent disc space through a disrupted end plate. Clinically, Kummell disease was suspected, which is thought to represent post-traumatic avascular necrosis. However, recent studies have shown that interruption of an end plate with or without intervertebral clefts in these types of patients is rather common, and probably represents fracture non-union. Imaging generally is not sensitive in detecting these clefts before vertebroplasty. These types of cases are very difficult to manage with conventional kyphoplasty because of the unpredictable risk of cement leakage. Also, reduction of the severe central fracture with conventional kyphoplasty is elusive, and the deformity is likely to recur after deflation of the kyphoplasty balloon and after creation of the cavity before injection of the hardenable fluid.

An implant as described herein may provide a superior alternative for improved management of these difficult cases. In some instances, one of the difficulties posed by this type of case is the presence of the severely depressed central end plates 24, 26 that pose the danger of crossing or penetrating the end plates with the introduction needle or guide pin. Another difficulty or risk factor is the presence of disruption of one or both end plates that would result in cement leakage.

Figure 57B:
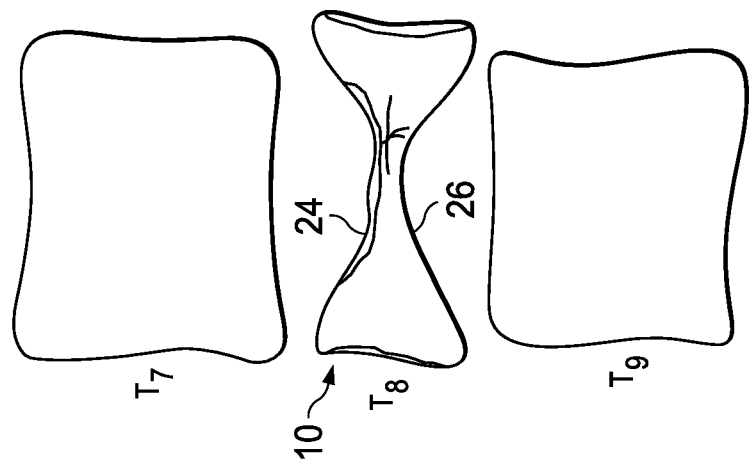
FIG. 57B is a schematic coronal view of the vertebrae of FIG. 57A.
Figure 57A:
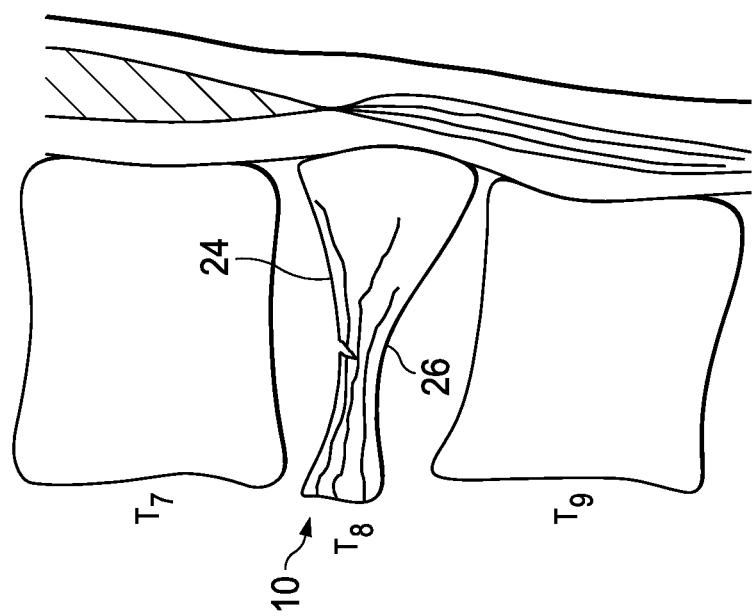
FIG. 57A is a schematic sagittal view of T7-T9 vertebrae wherein T8 has a central osteoporotic fracture with severe depression of both end plates, anterior wedging, retropulsion, and end plate disruption (butterfly fracture) prior to treatment with an implant as described herein.
Figure 57E:
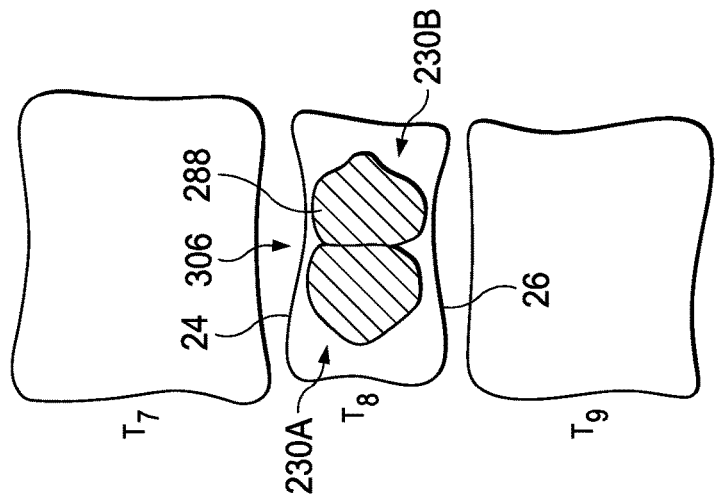
FIG. 57E is a schematic coronal view of the vertebrae and implants of FIG. 57D showing further inflation of the inflatable members such that the inflatable members are engaged with each other, further distraction of the vertebral end plates of T8, and further gain in vertebral height of T8.
Figure 57D:
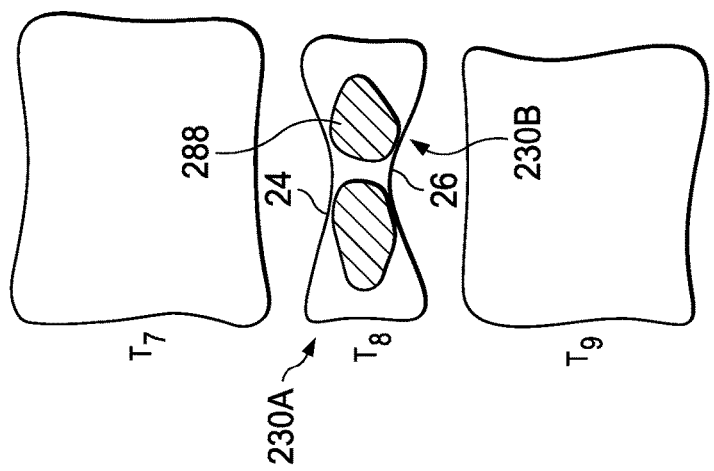
FIG. 57D is a schematic coronal view of the vertebrae and implants of FIG. 57C showing partial inflation of the inflatable members and distraction of the end plates of T8.
Figure 57C:
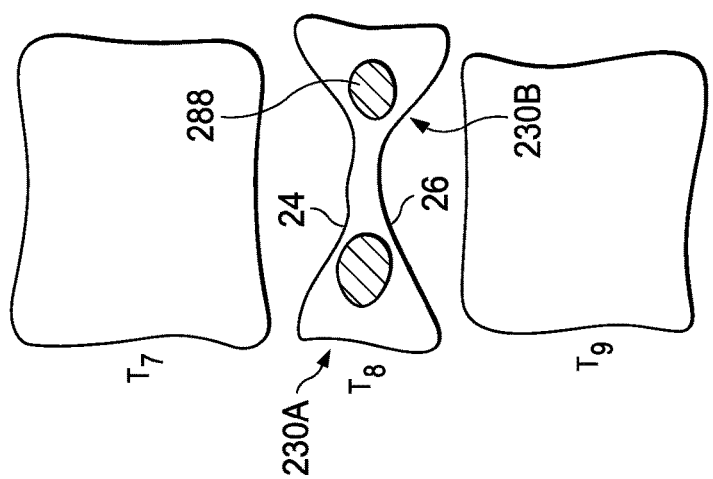
FIG. 57C is a schematic coronal view of the vertebrae of FIG. 57B showing insertion of bilateral prosthetic implants in T8 wherein the implants have slots to facilitate expansion of inflatable members directed medially.
Figure 57F:
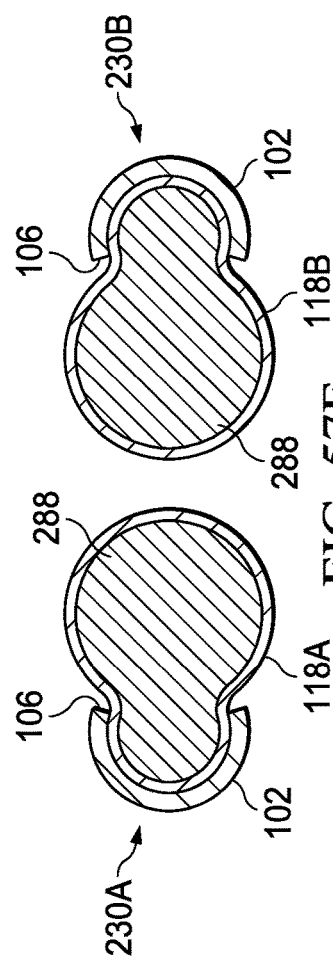
FIG. 57F is an enlarged, schematic, coronal, exploded cross-sectional view of the bilateral prosthetic implants of FIG. 57E showing medially oriented housing slots and medially directed inflatable members differentially expanding towards each other.
Figure 57H:
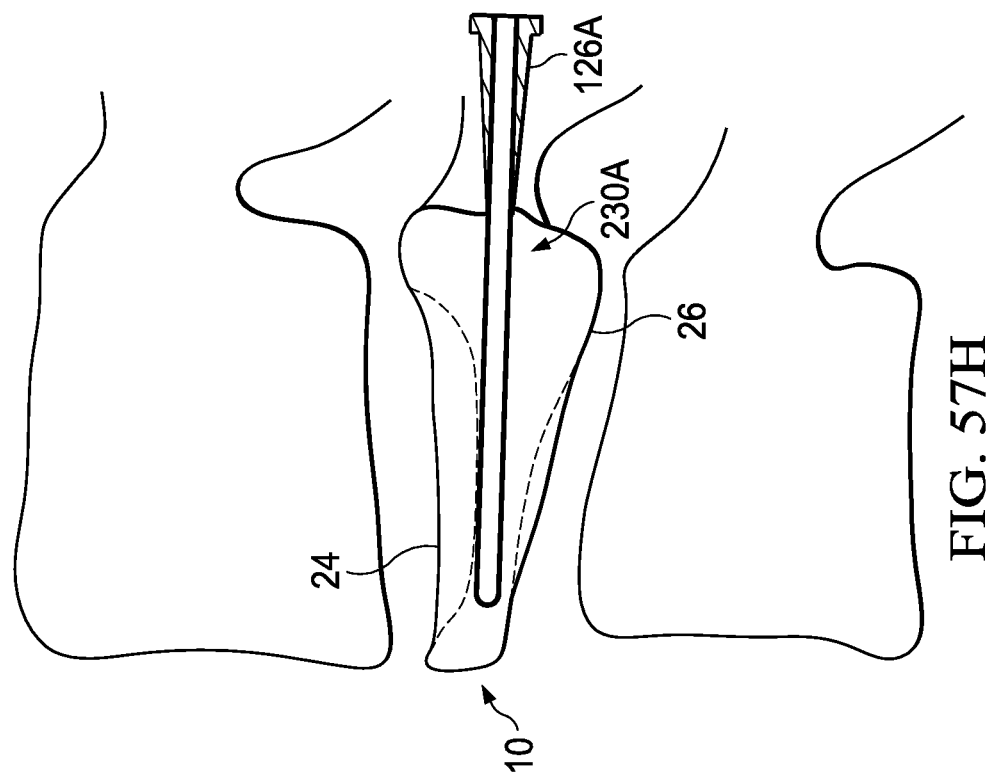
FIG. 57H is a schematic oblique parasagittal view of the vertebra and implants of FIG. 57C taken in the direction of section 57H-57H in FIG. 57G showing appropriate location of the implant insertion to avoid end plate penetration.
Figure 57G:
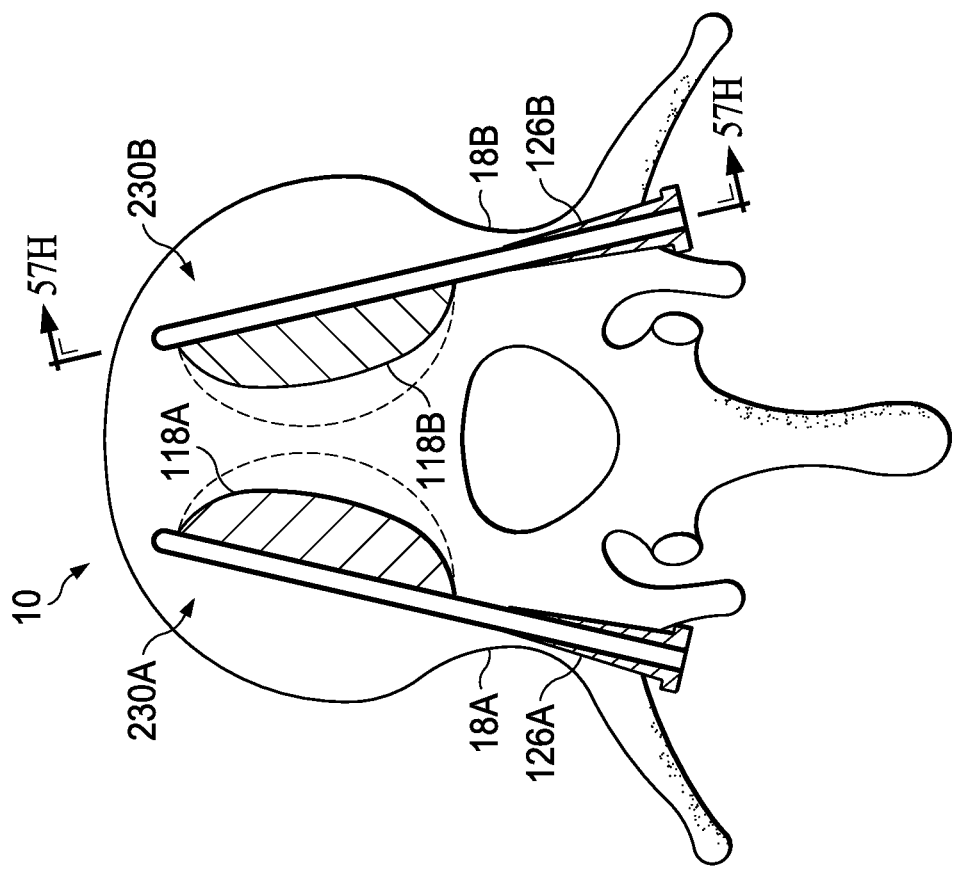
FIG. 57G is a schematic axial view of the T8 vertebra of FIG. 57F showing bilateral transpedicular implant insertion, including a relatively lateral orientation of the implant insertion in order to avoid penetrating the centrally depressed end plates.

With reference to FIG. 57G, the corrective kyphoplasty procedure may be performed with a bilateral transpedicular or parapedicular approach. In this type of case, the entry needle orientation may be almost straight in the anteroposterior plane in order to avoid directing the needles medially towards the depressed end plates 24, 26. Biplane fluoroscopic assessment may be used to ensure proper placement of the entry needles. The user should also take care to avoid penetrating the lateral vertebral cortex as there is a tendency to misjudge the true position of the needle with respect to the lateral and/or anterior cortical margin on fluoroscopy.

In this example, implants 230A, 230B are chosen having elongated apertures 106 on one side only of the respective housing 102 (see FIG. 57F), and these are directed medially with the two inflatable members 118A, 118B facing each other as they are progressively inflated with isoelastic hardenable fluid material 288. As such inflation occurs, the centrally depressed end plates 24, 26 are flattened and vertebral height is restored. Differential expansion of inflatable members 118A, 118B initially may be from lateral to medial, as shown in FIGS. 57C and 57D. As shown in FIG. 57E, after inflatable members 118A, 118B expand medially enough to engage each other along interface 306, they may then tend to expand axially toward end plates 24, 26. The risk of cement leakage (i.e., leakage of hardenable fluid material 288) is eliminated due to the self-sealing action of a one-way valve as described above. Careful fluoroscopic biplane monitoring, careful control of the volumes of hardenable fluid material 288 injected, and monitoring of the inflation pressure throughout the procedure is expected to achieve a safe outcome. Furthermore, there is expected pain control, satisfactory augmentation, stabilization, and restoration of isoelasticity of the treated vertebra with respect to the adjacent vertebrae.

Example 6

Implantable Multilevel CFD-KI Device

Figure 58:
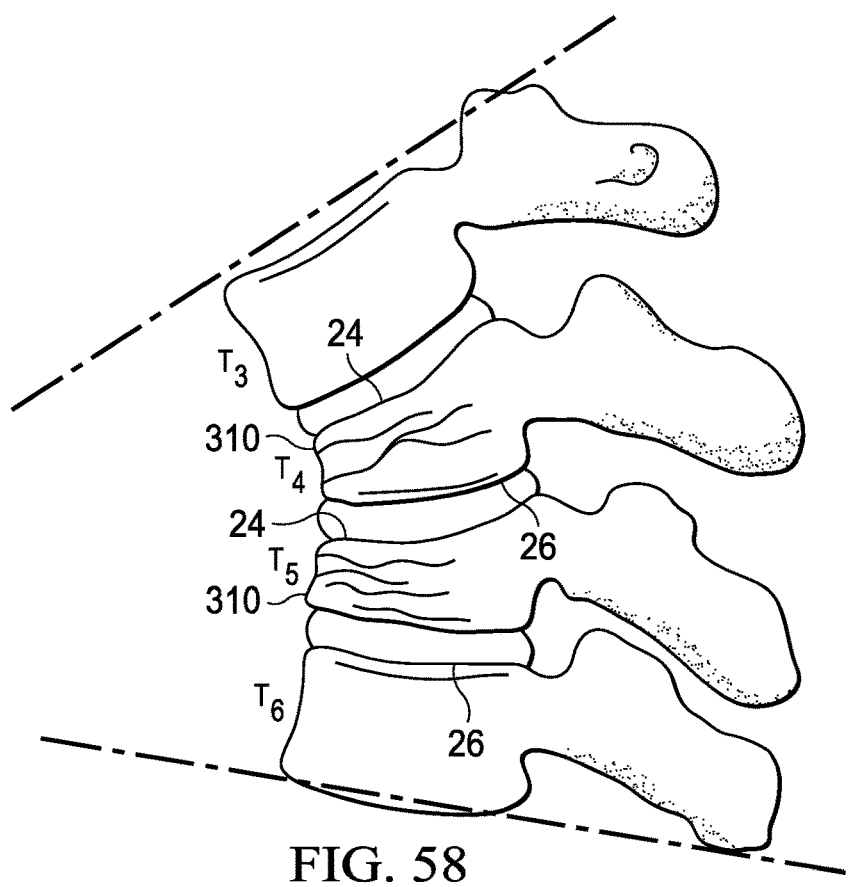
FIG. 58 is a schematic sagittal view of the mid-thoracic spine showing wedge-shaped osteoporotic fractures of the T4 and T5 vertebral bodies associated with a moderate degree of kyphotic deformity.

Referring to FIG. 58, a sagittal graphic shows two contiguous compression fractures involving the T4 and T5 vertebral bodies. At both levels, the superior and inferior end plates 24, 26 are involved, and there is anterior wedging 310 resulting in significant kyphotic deformity. Such fractures are difficult to see on radiographs and on fluoroscopy due to osteoporosis and due to overlap from the patients' shoulders. Such fractures often progress to severe and debilitating kyphotic deformity, and they may present as vertebral planae. These types of upper thoracic fractures are quite challenging even for the experienced practitioner, and they are very difficult to manage with conventional vertebroplasty or kyphoplasty. Access to T4 is especially problematic because of the relatively small size of the pedicles at this level.

Figure 59:
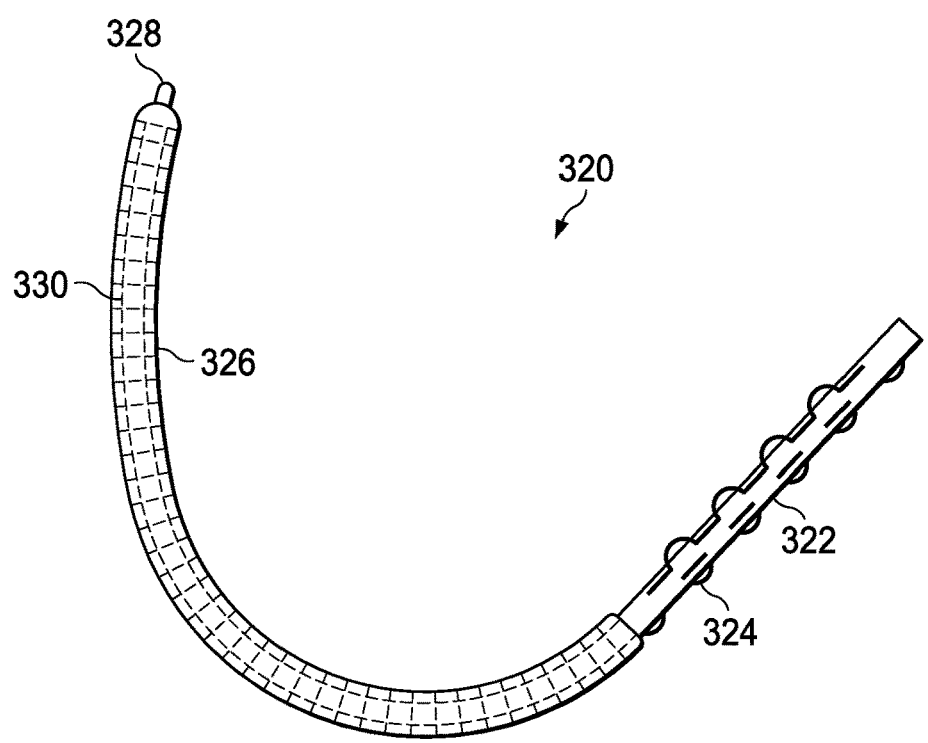
FIG. 59 is a schematic side elevational view of an embodiment of a CFD-KI device suitable for multi-level percutaneous implantation.

FIG. 59 is a frontal view of an embodiment of a kyphoplasty prosthesis 320, which can be implanted percutaneously into two adjacent vertebral bodies, via a transpedicular or parapedicular approach (usually bilaterally), crossing the intervertebral disc therebetween to simultaneously treat the two adjacent vertebral fractures. Because access to the lower thoracic vertebrae is considered relatively technically more feasible and safer, a bilateral parapedicular or transpedicular approach may be elected at the T5 level with percutaneous access in the usual fashion. Prosthesis 320 may include a CFD 322 having a plurality of anchors 324 configured for anchoring prosthesis 320 to the vertebral bone once the delivery cannula is withdrawn as described above for other embodiments. A tube 328 and a segmented balloon 326 may extend distally from CFD 322, and a jacket 330 may be disposed about balloon 326 similar to support 706 and inflatable member 718 described above. Internal passages in tube 328 and CFD 322 may be in fluid communication with a source of hardenable fluid 288, and tube 328 may have an internal orifice to allow hardenable fluid 288 to inflate balloon 326 similar to other embodiments described herein. A one-way valve (not shown) may be provided in CFD 322 or tube 328 to prevent hardenable fluid 288 from escaping prosthesis 320 after injection, similar to other embodiments described herein.

Figure 60A:
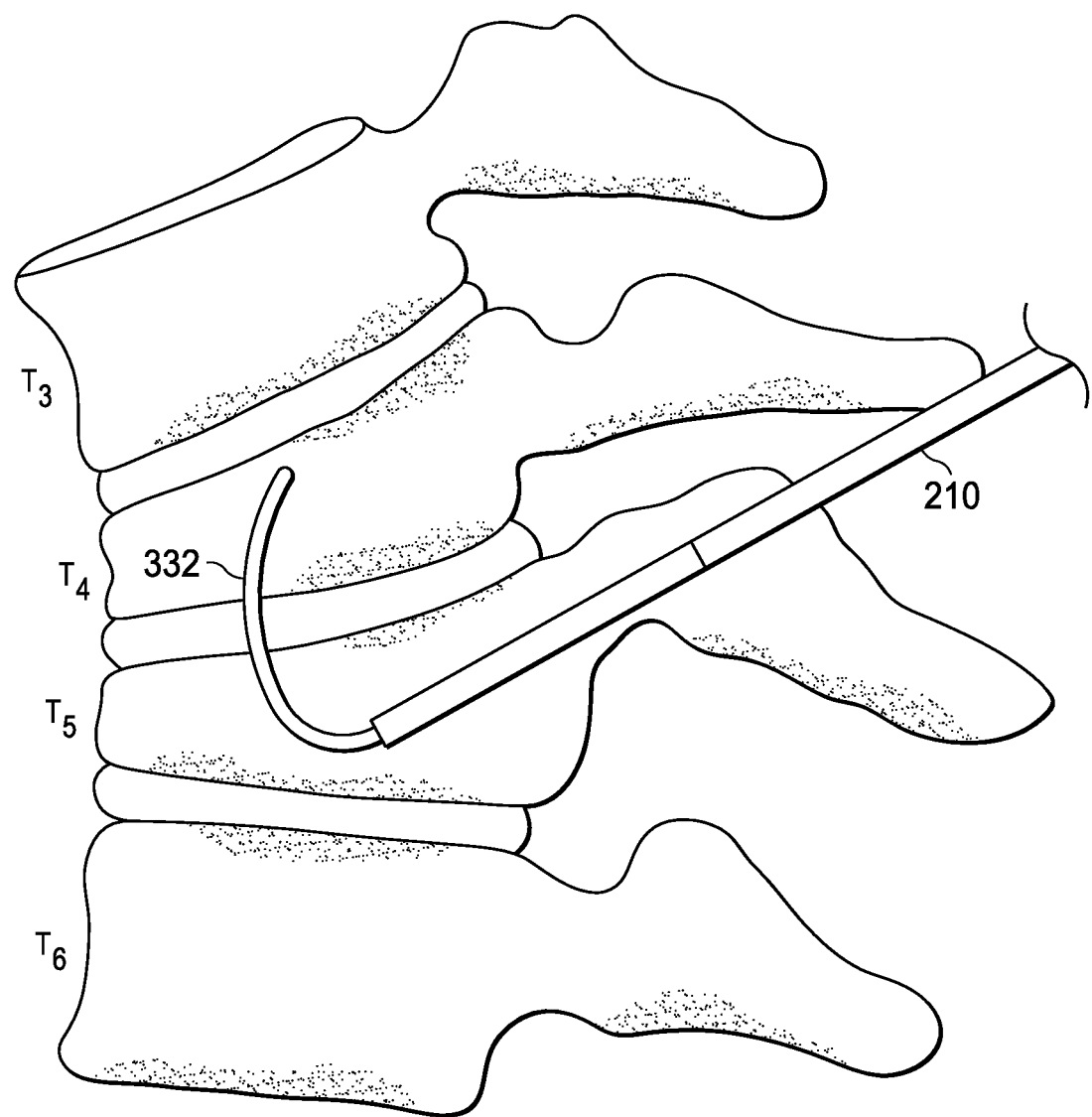
FIG. 60A is a schematic sagittal view similar to FIG. 58 showing percutaneous placement of an access cannula and curved guide-pin into the T5 vertebrae by a transpedicular approach and showing the curved guide pin has been directed cephalad into the adjacent T4 vertebral body, crossing the T4-T5 disc.

FIG. 60A depicts an access cannula 210 disposed about a curved guide pin 332, which has been directed cephalad towards the T4 vertebral body, crossing the T4-T5 intervertebral disc.

Figure 60B:
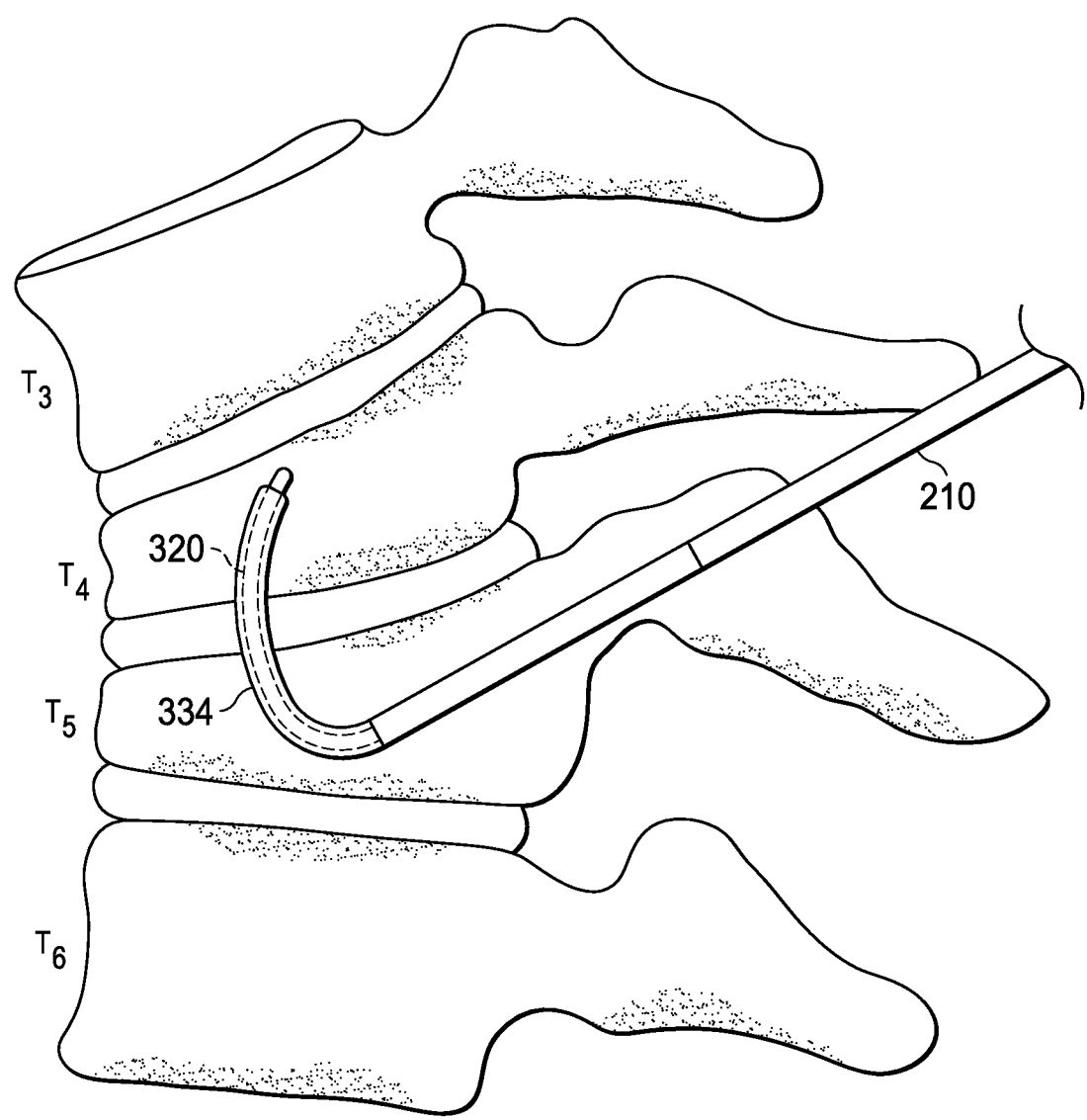
FIG. 60B is a schematic sagittal view similar to FIG. 60A showing that a curved guide pin has been removed from the lumen of the access cannula, and has been replaced by a delivery cannula, which is seen extending in the lumen of the access cannula. The uninflated multilevel CFD-KI device has been advanced into the access path.

In FIG. 60B, the guide pin 332 has been removed and replaced with a curved delivery cannula 334 inserted into the lumen of the access cannula 210. A multilevel CFD-KI prosthesis 320 may be thus delivered into the access path through curved delivery cannula 334.

Figure 60C:
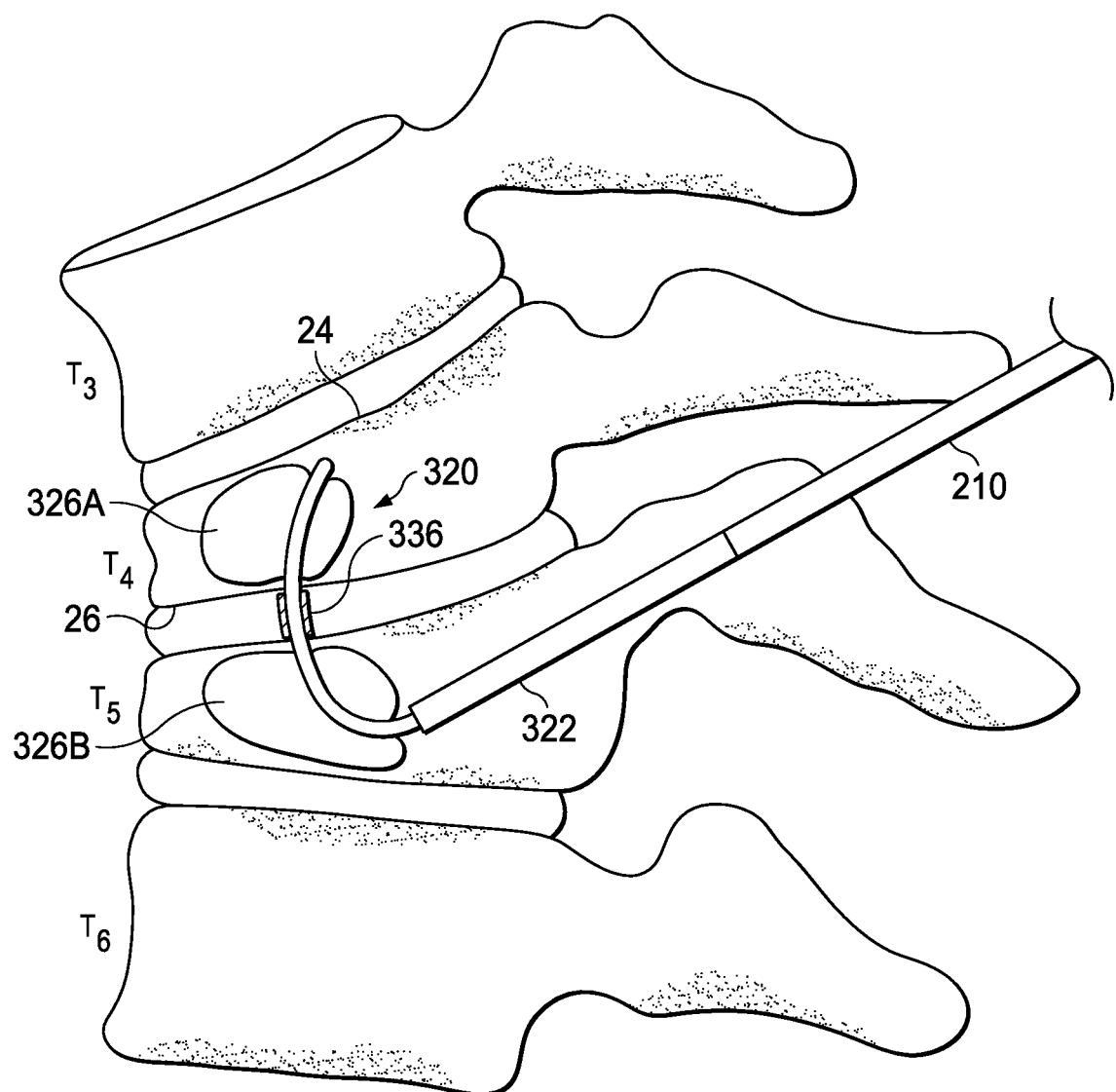
FIG. 60C is a schematic sagittal view similar to FIG. 60B, showing partial inflation of the segmented balloons in the T4 and T5 vertebral bodies and a marker at the T4-T5 disc level.

In FIG. 60C, segments 326A and 326B of balloon 326 are partially expanded with hardenable media 288, with initial flattening of the end plates 24, 26 at the two vertebral levels. A tubular radiopaque marker 336 may be placed around the inner tube 328 to serve as a fluoroscopic guide for the operator marking the intervertebral disc and ensuring that segment 326A is located within T4 and segment 326B is located within T5.

Figure 60D:
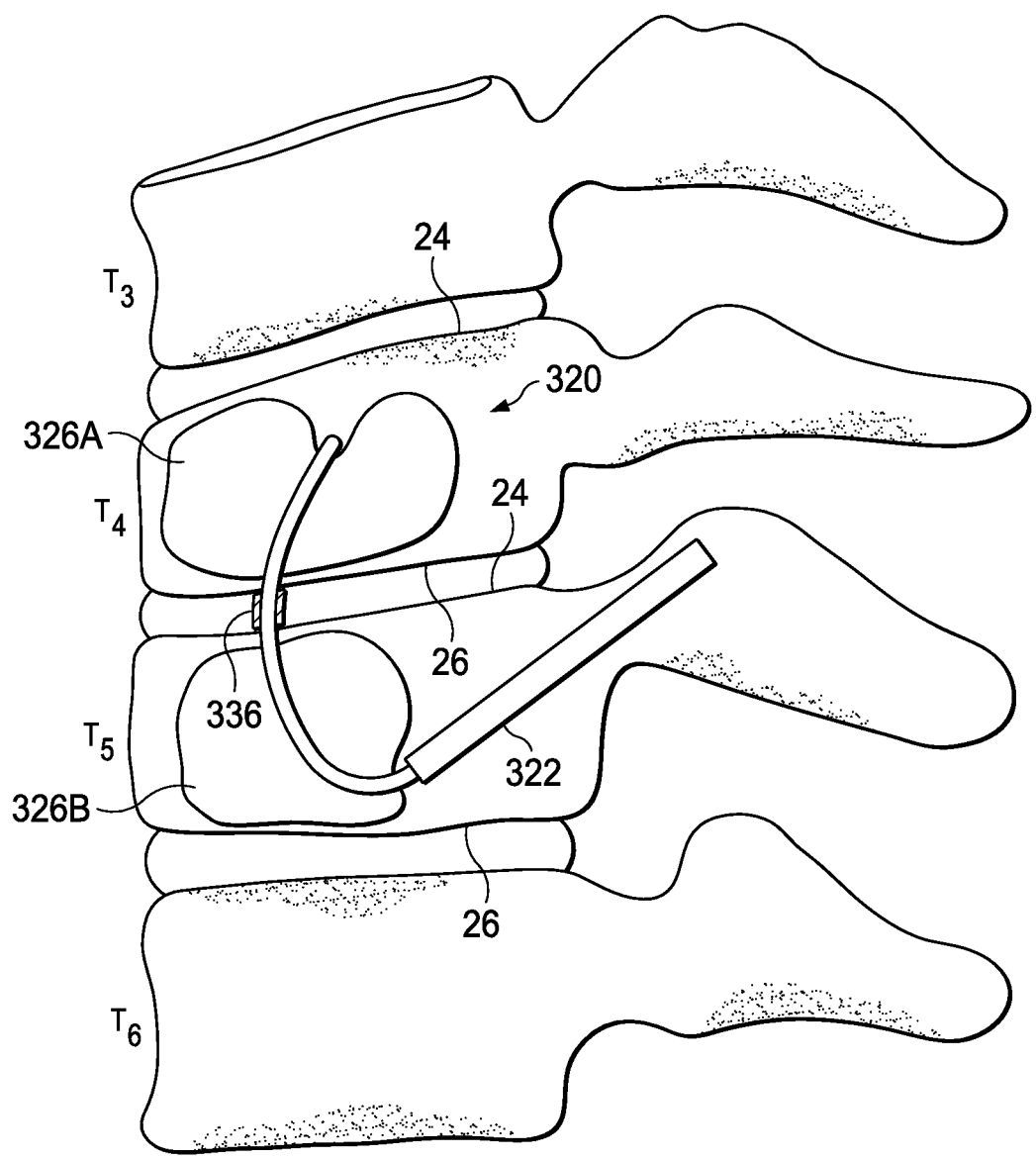
FIG. 60D is a schematic sagittal view similar to FIG. 60C showing further expansion of the segmented balloons and directional expansion of the T4 and T5 vertebral bodies with substantial correction of the kyphosis.

With further balloon inflation shown in FIG. 60D, there is expansion of the anterior portion of the T4 and T5 vertebral bodies thus resulting in kyphosis deformity correction and stabilization of the T4-T5 vertebral segment. The CFD 322 is shown in position within the T5 vertebral body and extending into the T5 pedicle, which contributes significantly to preventing undue motion of the prosthesis 320 and to the stabilization of the vertebral segment.

Figure 61:
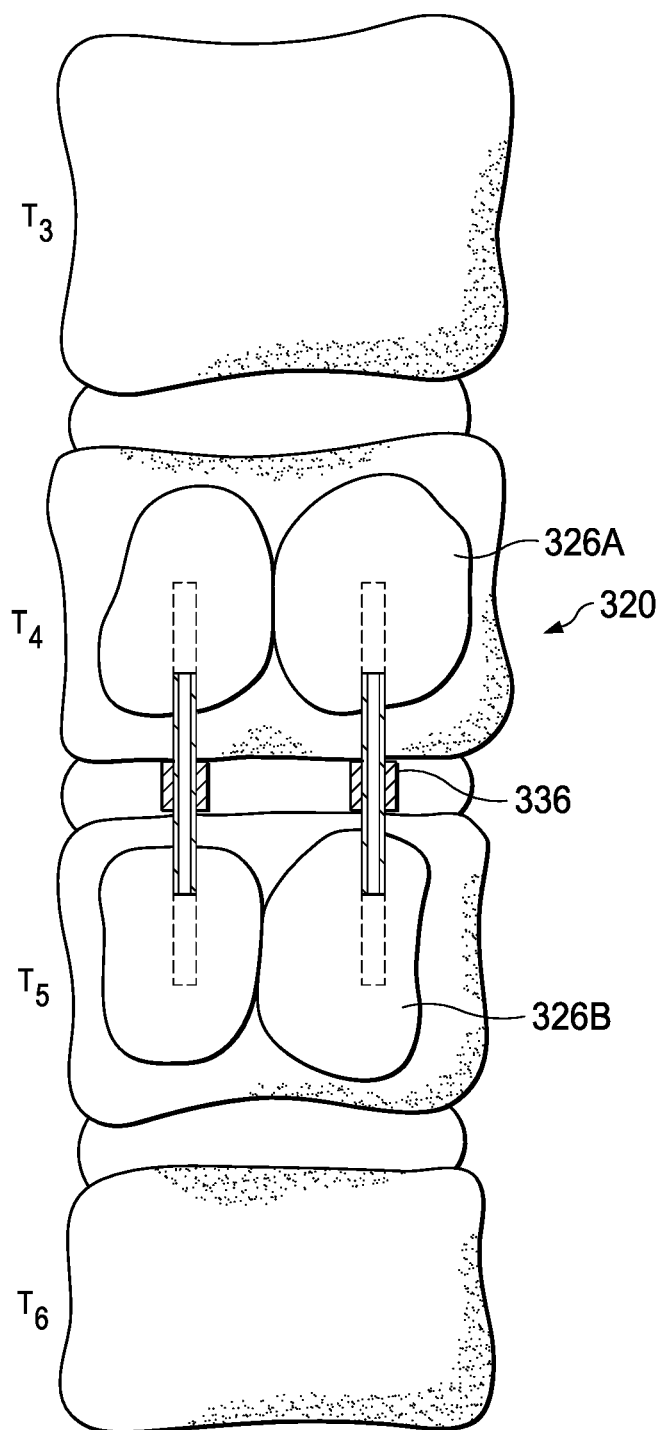
FIG. 61 is a schematic coronal view of the implant of FIG. 60D showing bilateral implantation of the multilevel prostheses and correction of the fracture deformity.

FIG. 61 demonstrates advantageous placement of the bilateral multilevel prosthesis 320. Note the bilateral markers 336 within the T4-T5 disc.

FIGS. 62 and 63 illustrate an alternative multilevel CFD-KI prosthesis 340 whereby segments 346A and 346B of balloon 346 provide multiple protrusions 348 that evaginate into the vertebral bodies and interdigitate between the trabeculae, further augmenting fixation and stabilization of the prosthesis 340 within the vertebral segments.

Example 7

FIG. 64 is a schematic lateral view of the T8-T9 level showing two contiguous osteoporotic vertebral body compression fractures 750 and 752. The T9 fracture 752 is especially technically problematic because the superior end plate 24 is cup-shaped showing significant central depression, risking inadvertent needle penetration during conventional kyphoplasty. As sown in FIG. 65, a multilevel CFD-KI prosthesis procedure may be performed in this case, with implantation of an alternative embodiment prosthesis 700 comprising a single lobulated inflatable member 718 that encompasses the T8 and T9 vertebral bodies including the T8-T9 disc space 740. A fastening element 744 is seen at a pedicular or parapedicular location of T8. Prosthesis 700 may include a tube 702 extending through inflatable member 718 and having an orifice 704 through which hardenable fluid 288 may be injected into inflatable member 718. Prosthesis 700 may be implanted into an insertion path formed in T8 and T9 using a pre-curved access cannula 766 as shown in FIG. 66.

Referring to FIGS. 67-69, a vertebral prosthesis deployment tool 760 may be used to deploy an expandable vertebral implant as described herein, such as implant 700, 710, or 720 described above, into two or more adjacent vertebrae. Deployment tool 760 may include a handle 761 and a guide cannula 762 depending from handle 761. Once an implant path has been created in the bone or other tissue to be repaired, a pre-curved access cannula 766 may be inserted into a lumen of the guide cannula 762, and a pre-curved guide pin 764 may be inserted through a lumen of the access cannula 766. The guide pin 764 may be used to facilitate installation of a fastening element 744 into a vertebral bone, for example, as shown in FIG. 65. Fastening element 744 may include a female luer connector, for example, that is configured for removable connection to a male luer connector of an inflation cannula (not shown) similar to inflation cannula 1019 or 220 described above, for example, to facilitate inflation of the expandable implant with hardenable fluid as described above after the expandable implant has been deployed. After fastening element 744 is installed, the guide pin 764 may be removed from the access cannula 766, and a pre-curved delivery cannula 768 may be inserted into the access cannula 766 as shown in FIG. 69. The curvature of access cannula 766 and delivery cannula 768 may be designed to be compatible with a curved insertion path as illustrated in FIG. 66. The delivery cannula 768 may be used to deploy the expandable implant into the desired position within the patient's body. For example, an implant 700 may be installed such that it spans at least a portion of two adjacent vertebrae T8 and T9 and traverses an intervertebral disc (not shown for the sake of clarity) disposed in space 740 between the two vertebrae as shown in FIG. 65. In such embodiments, implant 700 may be beneficially used to correct kyphosis caused by fractures 750 and 752 in vertebrae T8 and T9, respectively, as illustrated in FIG. 64, including restoration of vertebral height and correction of the deformity of end plates 24 and 26. In some embodiments, two expandable implants may be inserted through the same vertebral body using a transpedicular approach. Each implant may include a tube 746 that extends from the fastening element 744, and a one-way valve (not shown) may be provided in tube 746 to allow hardenable fluid 288 to be inserted through tube 746 and tube 702 and orifice 704 to expand inflatable member 718, and the valve may prevent fluid from flowing back out of the implant 700. In some embodiments, tube 746 and tube 702 may be a single tube.

Referring to FIGS. 70 and 71, another embodiment of an inflatable implant 1130 is shown. In this embodiment, inflatable implant 1130 may include a first balloon 1132 and a second balloon 1134 disposed about a shaft 1136. Shaft 1136 may include a first lumen 1140 in fluid communication with first balloon 1132 via an opening 1144. Similarly, shaft 1136 may include a second lumen 1138 in fluid communication with second balloon 1134 via an opening 1142. Lumens 1138 and 1140 may be in fluid communication with a source of hardenable fluid for inflating balloons 1132 and 1134, respectively, within two adjacent vertebral bodies. Thus, in some embodiments, the implant 1130 may comprise a double-balloon implantable catheter comprising a proximal balloon 1132 and a distal balloon 1134, wherein each balloon is respectively insertable into an adjacent vertebral body, similar to that shown in FIGS. 60C, 60D, 61, 62, 63, and 65, for example. In some embodiments, the balloons 1132 and 1134 may be inflated sequentially, and in other embodiments balloons 1132 and 1134 may be inflated simultaneously. In some embodiments, the balloons 1132 and 1134 may be of different volumes, corresponding to the size of the respective vertebral body. In some embodiments, only a single lumen may be provided in shaft 1136 to supply hardenable fluid to both balloons 1132 and 1134. In other embodiments, a first lumen 1140 and a second lumen 1138 may extend through the catheter and supply the balloons 1132 and 1134 independently, whereby both balloons 1132 and 1134 are independently expandable and adjustable in inflation size, shape, and differential expansion capability to correct osteoporotic vertebral fracture deformity and to stabilize the vertebral segment. In some embodiments, each of the balloons 1132 and 1134 may have an overlying support structure as described above and may be longitudinally expandable or inflatable, and each of the balloons 1132 and 1134 may be independently adjustable.

It should be noted that although some embodiments of inflatable implants described herein include a one-way valve configured for allowing hardenable fluid to pass through the one-way valve into one or more inflatable members and preventing the hardenable fluid from escaping back out of the one or more inflatable members, some embodiments may not include such a one-way valve. For example, in some embodiments, following inflation of the one or more inflatable members with hardenable fluid, the inflation cannula may remain engaged with the fluid coupler of the implant for a time sufficient to allow the hardenable fluid to cure within the implant, and then the inflation cannula may be disengaged from the fluid coupler. Since the hardenable fluid has been cured, it cannot escape back out of the one or more inflatable members. Thus, a one-way valve may not be needed in some embodiments.

In some embodiments, during balloon expansion, the increasing balloon diameter may urge the fibers, wires, or other elements of the supporting structure or jacket to deviate away from the most direct path between the first, second, or third attachment locations, or other balloon attachments. Since the fibers of the supporting structure have little capacity for stretching, differential expansion of the implant will occur along the path of least resistance, thus achieving the longitudinal lengthening desired to restore vertebral height, primarily directed toward distraction of vertebral end-plates and limiting transverse expansion that may lead to inadvertent retropulsion into the spinal canal.

In an exemplary embodiment, the supporting structure or jacket may be separate from the balloon membrane and freely movable relative to the external balloon surface. In some embodiments, several helically wound fibers may be used and configured into a knit pattern braid, warp, mesh, or the like.

In some embodiments, the supporting structure or jacket may be formed from substantially inelastic polymeric material (e.g., nylon, Kevlar™, Spectra, Dacron, Dyneema, Polyimide (PIM), ultra-high molecular weight polyethylene, Zylon™ (PBO), and the like, or a combination thereof). Metals such as Nitinol may also be used. The fibers are suitably flexible to be shaped into a low-profile configuration when the balloon is deflated, e.g., for implant loading in a delivery cannula.

In an exemplary embodiment, an inflatable kyphoplasty implant may be configured to include a supporting structure such as a mesh, braid, warp, and the like, which is carried by a segmented balloon membrane. The segmented balloon(s) may take a variety of forms depending on the degree and configuration of segmentation. Other exemplary balloons may include adjacent segments that are separated by grooves in an otherwise continuous balloon. These localized "hinge-points" act in the manner of "bellows" imparting differential flexibility to the balloon membrane. Other balloons may have deep grooves that separate bulges in the balloon profile, while maintaining modest flexibility to the balloon structure.

Other exemplary balloons may include helical balloons to provide a bending or twisting bias in the longitudinal plane, while maintaining flexibility.

Other exemplary balloons may be corrugated whereby adjacent segments on the outer aspect of the bend in the balloon can separate while those on the inner aspect remain in close opposition. The resulting potential for differential lengthening may provide the desired "hoop strength" to correct deformity in patients with severe osteoporotic fractures and significant deformity, and/or angulation.

In some embodiments, balloons useful for kyphoplasty implants may be constructed of low-compliance materials that tolerate high inflation pressures and attain predictable diameters and configurations in-vivo.

Conventional angioplasty and kyphoplasty balloons are typically of uniform cylindrical shape and are of uniform diameter between conical ends and have a central catheter extending along the longitudinal axis of the balloon. When inflated at high pressures, the walls of the balloon are placed into tension and the balloon generally loses its capacity for differential lengthening and hence becomes stiff and biased into a straightened configuration. Such balloons impose this straightened cylindrical configuration on any overlying supporting structure or when implanted into body tissues or organs.

In an exemplary embodiment, a supporting structure is wrapped around or otherwise positioned externally of the balloon membrane. The supporting structure may allow the balloon to retain increased flexibility when deflated and reduced to a minimal profile for loading into a delivery cannula. To a certain degree, flexibility of the kyphoplasty implant is maintained at initial stages of inflation and expansion. At higher pressures, the overlying structure may be configured to bias the implant in certain predictable directions in order to achieve deformity correction in a particular clinical setting.

In some embodiments, one advantage of the in-situ prosthesis formation described herein over conventional kyphoplasty procedures, wherein hardenable media is injected into an uncontained cavity or space, is that the possibility of fluid material leakage is minimized or eliminated. Further, higher inflation pressures may be achieved, and the direction of expansion may be controlled, resulting in more consistent deformity correction, while enabling the use of a smaller amount of hardenable fluid media. This allows procedure morbidity to be minimized. In addition, the in-situ formation in accordance with certain embodiments described herein may allow tailored design and formation of a variety of implantable prostheses of different shapes and sizes. Further, the operator may have better control on the direction of expansion of the prosthesis in real-time under imaging guidance.

All patents and published patent applications referenced in this disclosure are incorporated herein by reference.

The embodiments described herein are some examples of the current invention. It will be appreciated by those skilled in the art that changes could be made to the embodiments and features described above without departing from the broad inventive concept thereof. It is understood, therefore, that this invention is not limited to the particular embodiments disclosed, but it is intended to cover modifications within the spirit and scope of the present invention. Among other things, any feature described for one embodiment may be used in any other embodiment. Also, unless the context indicates otherwise, it should be understood that when a component is described herein as being mounted or connected to another component, such mounting or connection may be direct with no intermediate components or indirect with one or more intermediate components. The scope of the invention is defined by the attached claims and other claims that may be drawn to this invention, considering the doctrine of equivalents, and is not limited to the specific examples described herein.

What is claimed is:

1. A spinal implant comprising:
   a housing comprising a wall having at least one opening therein;
   an inflatable member disposed in said housing;
   a fluid coupler connected to said housing; and
   a one-way valve disposed in said housing and configured to permit a hardenable fluid to flow in a distal direction from said fluid coupler into said inflatable member and to prevent the hardenable fluid from flowing back in a proximal direction from said inflatable member into said fluid coupler;
   wherein at least a portion of said inflatable member is configured to expand through said at least one opening of said housing upon inflation of said inflatable member by the hardenable fluid.

2. The spinal implant of claim 1 wherein said housing comprises a proximal flange having a proximal face configured for removable engagement with an insertion tool and a distal face configured for abutting engagement with a flange of an external fastener.

3. The spinal implant of claim 1 further comprising an expandable jacket disposed about said inflatable member.

4. The spinal implant of claim 3 wherein said expandable jacket comprises a plurality of jacket openings defined by a plurality of segments, and wherein said inflatable member is configured to form a plurality of bulges by expansion of said inflatable member through said plurality of jacket openings.

5. The spinal implant of claim 4 wherein said plurality of jacket openings are configured to direct said plurality of bulges in a plurality of pre-determined directions with respect to said housing.

6. The spinal implant of claim 1 further comprising an end cap at a distal end of said housing and an internal cannula extending through said housing from said fluid coupler to said end cap;
   wherein said internal cannula comprises an orifice configured to direct the hardenable fluid into said inflatable member.

7. The spinal implant of claim 1 wherein the fluid coupler comprises a threaded female socket configured for connection to an inflation cannula having a threaded male nozzle.

8. The spinal implant of claim 1 wherein the fluid coupler comprises a female luer connector.

9. The spinal implant of claim 1 wherein the fluid coupler is configured for threaded connection to an inflation cannula and further comprises one or more recesses configured for engagement with one or more protrusions of an anti-rotation device.

10. An apparatus comprising:
    a spinal implant comprising an inflatable member, a one-way valve configured to permit inflation of said inflatable member and to prevent deflation of said inflatable member, and a fluid coupler;
    an inflation cannula configured for removable connection to said fluid coupler and a pressurized source of hardenable fluid;
    an insertion tool configured for removable engagement with said implant; and
    a delivery cannula configured to removably receive said implant, said inflation cannula, and said insertion tool;
    wherein said inflation cannula is configured to inject the hardenable fluid through said one-way valve into said inflatable member to cause expansion of said inflatable member.

11. The apparatus of claim 10 further comprising the pressurized source of hardenable fluid and a conduit configured for fluid communication between said pressurized source of hardenable fluid and said inflation cannula.

12. The apparatus of claim 10 further comprising a handle configured for manual manipulation of said inflation cannula, said insertion tool, and said delivery cannula.

13. The apparatus of claim 10 further comprising an access cannula configured to removably receive said delivery cannula.

14. The apparatus of claim 13 wherein said access cannula and said delivery cannula comprise a pre-curved portion.

15. The apparatus of claim 10 wherein said insertion tool comprises a protrusion configured for removable engagement with a recess in said implant to prevent rotation of said implant during connection and disconnection of said inflation cannula with said fluid coupler.

16. A method of treating a vertebra comprising:
    creating an insertion path in the vertebra;
    inserting an implant into the insertion path, said implant comprising an inflatable member, a one-way valve configured to permit inflation of said inflatable member and to prevent deflation of said inflatable member, and a fluid coupler;
    connecting an inflation cannula to said fluid coupler;
    injecting a hardenable fluid through said inflation cannula, said fluid coupler, and said one-way valve into said inflatable member to expand said inflatable member within the vertebra;
    disconnecting said inflation cannula from said fluid coupler;
    engaging an insertion tool with said implant to prevent rotation of said implant during said connecting and said disconnecting; and
    disengaging said insertion tool from said implant after said disconnecting.

17. The method of claim 16 wherein said implant comprises a housing comprising a wall having at least one opening therein, and wherein said inflatable member is disposed within said housing prior to said injecting, said method further comprising:
    expanding said inflatable member through said at least one opening of said housing.

18. The method of claim 17 further comprising:
    positioning said implant in a desired orientation within the insertion path using said insertion tool;
    wherein said expanding comprises expanding said inflatable member in a selected direction within the vertebra.

19. The method of claim 18 wherein said wall comprises a plurality of openings, and wherein said expanding comprises expanding said inflatable member in a plurality of selected directions within the vertebra.

20. The method of claim 19 wherein said expanding comprises differentially expanding said inflatable member in at least two of said plurality of selected directions.

21. The method of claim 20 wherein said implant further comprises an expandable jacket disposed about said inflatable member, and wherein said differentially expanding said inflatable member is facilitated at least in part by said expandable jacket.

22. The method of claim 16 wherein said implant comprises a housing comprising a proximal housing segment, an intermediate housing segment, and a distal housing segment; said inflatable member being connected to said distal housing segment; said proximal housing segment comprising said fluid coupler; said proximal housing segment having a maximum outer dimension; said intermediate housing segment comprising at least one resilient member; said at least one resilient member being configurable in a compressed condition in which said at least one resilient member does not extend beyond said maximum outer dimension, and said at least one resilient member being biased toward an expanded condition in which said at least one resilient member extends beyond said maximum outer dimension; an inflation tube disposed within said housing and extending from said fluid coupler into said inflatable member; said one-way valve being disposed in said inflation tube; said method further comprising:

placing said implant into a delivery cannula such that said at least one resilient member is in said compressed condition within the delivery cannula; and once said implant is positioned within the insertion path, retracting the delivery cannula to allow said at least one resilient member to move into said expanded condition to secure said implant to the vertebra.

\* \* \* \* \*